(12) United States Patent
Wagner et al.

(10) Patent No.: US 9,675,358 B2
(45) Date of Patent: Jun. 13, 2017

(54) CONDUIT FOR PERIPHERAL NERVE REPLACEMENT

(71) Applicant: WAKE FOREST UNIVERSITY HEALTH SCIENCES, Winston-Salem, NC (US)

(72) Inventors: William D. Wagner, Clemmons, NC (US); Nicole Levi, Winston-Salem, NC (US); Tabitha Rosenbalm, Winston-Salem, NC (US); Louis C. Argenta, Winston-Salem, NC (US); Michael J. Morykwas, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 199 days.

(21) Appl. No.: 14/391,346

(22) PCT Filed: Mar. 15, 2013

(86) PCT No.: PCT/US2013/032520
§ 371 (c)(1),
(2) Date: Oct. 8, 2014

(87) PCT Pub. No.: WO2013/154780
PCT Pub. Date: Oct. 17, 2013

(65) Prior Publication Data
US 2015/0032137 A1 Jan. 29, 2015

Related U.S. Application Data

(60) Provisional application No. 61/623,528, filed on Apr. 12, 2012.

(51) Int. Cl.
*A61B 17/11* (2006.01)
*A61L 27/18* (2006.01)
(Continued)

(52) U.S. Cl.
CPC ........ *A61B 17/1128* (2013.01); *A61F 2/0077* (2013.01); *A61L 27/18* (2013.01);
(Continued)

(58) Field of Classification Search
CPC ........ A61B 17/1128; A61B 2017/1132; A61B 2017/00991; A61B 2017/00831;
(Continued)

(56) References Cited

U.S. PATENT DOCUMENTS 4,187,852 A 2/1980 Urry
4,661,530 A 4/1987 Gogolewski
(Continued)

FOREIGN PATENT DOCUMENTS

DE 4439240 5/1996
GB 712939 8/1954
(Continued)

OTHER PUBLICATIONS

International Preliminary Report on Patentability from International Application No. PCT/US2013/032520 dated Oct. 14, 2014.
(Continued)

*Primary Examiner* — Julian W Woo
(74) *Attorney, Agent, or Firm* — Niels Haun; Dann, Dorfman, Herrell and Skillman, P.C.

(57) ABSTRACT

A biphasic material and devices comprising the same are provided for the development of conductive conduits that may be used for the treatment of peripheral nerve injury. These devices or conduits are designed such that repeated electric field gradients can be initiated to promote neurite and axonal outgrowth. Conducting conduits using doped synthetic and/or natural polymers create specifically patterned high and low conducting segmented materials, which are mechanically used to produce the electrical properties needed for nerve conduits. These electrical properties stimu-
(Continued)

late neurite outgrowth and axonal repair following a peripheral nerve transection.

63 Claims, 33 Drawing Sheets

(51) Int. Cl.
*A61L 27/44* (2006.01)
*A61L 27/50* (2006.01)
*A61F 2/00* (2006.01)
*A61L 27/26* (2006.01)
*A61L 27/58* (2006.01)
*C08G 63/12* (2006.01)
*C08G 63/47* (2006.01)
*H01B 1/12* (2006.01)
*A61B 17/00* (2006.01)

(52) U.S. Cl.
CPC ............ *A61L 27/26* (2013.01); *A61L 27/446* (2013.01); *A61L 27/50* (2013.01); *A61L 27/58* (2013.01); *C08G 63/12* (2013.01); *C08G 63/47* (2013.01); *H01B 1/125* (2013.01); *A61B 2017/00004* (2013.01); *A61B 2017/00831* (2013.01); *A61B 2017/00991* (2013.01); *A61B 2017/1132* (2013.01); *A61L 2400/12* (2013.01); *A61L 2430/32* (2013.01)

(58) Field of Classification Search
CPC .......... A61B 2017/00004; C08G 63/12; C08G 63/47; H01B 1/125; A61F 2/0077; A61L 27/26; A61L 27/58; A61L 27/50; A61L 27/446; A61L 27/18; A61L 2430/32; A61L 2400/12
See application file for complete search history.

(56) References Cited

U.S. PATENT DOCUMENTS

| | | | |
|---|---|---|---|
| 4,841,962 A | 6/1989 | Berg | |
| 5,024,841 A | 6/1991 | Chu | |
| 5,516,396 A | 5/1996 | Maurer | |
| 5,607,590 A | 3/1997 | Shimizu | |
| 5,736,372 A | 4/1998 | Vacanti | |
| 5,766,618 A | 6/1998 | Laurencin | |
| 6,095,148 A | 8/2000 | Shastri | |
| 6,306,424 B1 * | 10/2001 | Vyakarnam | A61F 2/30756 424/422 |
| 7,216,651 B2 | 5/2007 | Argenta | |
| 7,722,894 B2 | 5/2010 | Wang | |
| 8,632,523 B2 | 1/2014 | Eriksson | |
| 8,932,620 B2 | 1/2015 | Lelkes | |
| 2002/0004556 A1 | 1/2002 | Foulger | |
| 2003/0027332 A1 | 2/2003 | Lafrance | |
| 2003/0118692 A1 | 6/2003 | Wang | |
| 2004/0210009 A1 | 10/2004 | Kobayashi | |
| 2005/0063939 A1 | 3/2005 | Ameer | |
| 2006/0263417 A1 | 11/2006 | Lelkes | |
| 2006/0293169 A1 | 12/2006 | Srinivasan | |
| 2007/0155010 A1 | 7/2007 | Farnsworth | |
| 2007/0208420 A1 | 9/2007 | Ameer | |
| 2008/0009830 A1 | 1/2008 | Fujimoto | |
| 2008/0112998 A1 | 5/2008 | Wang | |
| 2008/0147156 A1 | 6/2008 | Imran | |
| 2009/0011486 A1 | 1/2009 | Bettinger | |
| 2009/0093565 A1 | 4/2009 | Yang | |
| 2009/0148945 A1 | 6/2009 | Ameer | |
| 2009/0187259 A1 | 7/2009 | Argenta | |
| 2009/0295644 A1 | 12/2009 | Curran | |
| 2009/0325859 A1 | 12/2009 | Ameer | |
| 2010/0196478 A1 | 8/2010 | Masters | |
| 2010/0221304 A1 | 9/2010 | Tan | |
| 2011/0052646 A1 | 3/2011 | Kaigler | |
| 2011/0129436 A1 | 6/2011 | Pryor | |
| 2011/0262489 A1 | 10/2011 | Zhao | |
| 2012/0016325 A1 | 1/2012 | Pinto | |
| 2012/0265297 A1 | 10/2012 | Altman | |
| 2014/0079759 A1 | 3/2014 | Patel | |

FOREIGN PATENT DOCUMENTS

| | | |
|---|---|---|
| JP | 1004629 | 1/1989 |
| JP | 2008099565 | 5/2008 |
| WO | 9000060 | 1/1990 |
| WO | 9918892 | 4/1999 |
| WO | 0061206 | 10/2000 |
| WO | 03026489 | 4/2003 |
| WO | 2007060433 | 5/2007 |
| WO | 2012004627 | 1/2012 |
| WO | 2012078472 | 6/2012 |

OTHER PUBLICATIONS

International Search Report from International Application No. PCT/US2013/032520 dated Aug. 2, 2013.
Written Opinion from International Application No. PCT/US2013/032520 date Aug. 2, 2013.
Evans GRD. Peripheral nerve injury: A review and approach to tissue engineered constructs. Anatomical Record 2001; 263(4):396-404.
Meek MF, Coert JH. US Food and Drug Administration/Conformit Europe-approved absorbable nerve conduits for clinical repair of peripheral and cranial nerves. Ann Plast Surg Jan. 2008;60(1):110-116.
Sondell M, Lundborg G, Kanje M. Regeneration of the rat sciatic nerve into allografts made acellular through chemical extraction. Brain Res Jun. 8, 1998;795(1-2):44-54.
Merle M, Dellon AL, Campbell JN, Chang PS. Complications from silicon-polymer intubulation of nerves. Mircrosurgery 1989; 10(2)130-133.
Meek MF, Coert JH. Clinical use of nerve conduits in peripheral-nerve repair: review of the literature. J Reconstr Microsurg Feb. 2002;18(2):97-109.
FitzGerald MJT. Neuroanatomy: Basic and Clinical. Philadelphia: W.B. Saunders Company, Ltd., 1996.
Young PA, Young PH. Basic Clinical Neuroanatomy. Philedelphia: Lippincott Williams, and Wilkins, 1997.
MacKinnon SE, Dellon AL. Surgery of the Peripheral Nerve. Thieme Medical Publishers New York, 1988.
Medscape: Diseases of the Peripheral Nervous System. Web MD Inc., ACP Medicine, 2004.
Stoll G, Muller HW. Nerve injury, axonal degeneration and neural regeneration: basic insights. Brain Pathol Apr. 1999;9(2):313-325.
Gordon T. The role of neurotrophic factors in nerve regeneration. Neurosurg Focus 2009;26(2):E3.
Wood MD, Moore AM, Hunter DA, Tuffaha S, Borschel GH, Mackinnon SE, et al. Affinity-based release of glial-derived neurotrophic factor from fibrin matrices enhances sciatic nerve regeneration. Acta Biomater May 2009;5(4):959-968.
Hayashi A, Moradzadeh A, Tong A, Wei C, Tuffaha SH, Hunter DA, et al. Treatment modality affects allograft-derived Schwann cell phenotype and myelinating capacity. Exp Neurol Aug. 2008;212(2):324-336.
Lee AC, Yu VM, Lowe JB, 3rd, Brenner MJ, Hunter DA, Mackinnon SE, et al. Controlled release of nerve growth factor enhances sciatic nerve regeneration. Exp Neurol Nov. 2003;184(1):295-303.
Deister C, Schmidt CE. Optimizing neurotrophic factor combinations for neurite outgrowth. J Neural Eng Jun. 2006;3(2):1 72-179.
Ahmed I, Liu HY, Mamiya PC, Ponery AS, Babu AN, Weik T, et al. Three-dimensional nanofibrillar surfaces covalently modified with tenascin-C-derived peptides enhance neuronal growth in vitro. J Biomed Mater Res A Mar. 15, 2006;76(4):851-860.
Zhang L, Ma Z, Smith GM, Wen X, Pressman Y, Wood PM, et al. GDNF-enhanced axonal regeneration and myelination following spinal cord injury is mediated by primary effects on neurons. Glia Jan. 23, 2009.

(56) References Cited

OTHER PUBLICATIONS

Zhang X, MacDiarmid AG, Manohar SK. Chemical synthesis of PEDOT nanofibers. Chem Commun (Camb) Nov. 14, 2005(42):5328-5330.

Kim YT, Haftel VK, Kumar S. Bellamkonda RV. The role of aligned polymer fiber-based constructs in the bridging of long peripheral nerve gaps. Biomaterials Jul. 2008;29(21):3117-3127.

Yang F, Murugan R, Wang S, Ramakrishna S. Electrospinning of nano/microscale poly(L-lactic acid) aligned fibers and their potential in neural tissue engineering. Biomaterials May 2005;26(15):2603-2610.

Wen X, Tresco PA. Effect of filament diameter and extracellular matrix molecule precoating on neurite outgrowth and Schwann cell behavior on multifilament entubulation bridging device in vitro. J Biomed Mater Res A Mar. 1, 2006;76(3):626-637.

Corey JM, Lin DY, Mycek KB, Chen Q, Samuel S, Feldman EL, et al. Aligned electrospun nanofibers specify the direction of dorsal root ganglia neurite growth. J Biomed Mater Res a Dec. 1, 2007;83(3):636-645.

Fan YW, Cui FZ, Chen LN, Zhai Y, Xu QY, Lee IS. Adhesion of neural cell son silicon wafer with nano-topographic surface. Applied Surface Science 2002;187 (3-4):313-318.

Schmalenberg KE, Uhrich KE. Micropatterned polymer substrates control alignment of proliferating Schwann cells to direct neuronal regeneration. Biomaterials Apr. 2005;26(12):1 423-1430.

Bruder JM, Lee AP, Hoffman-Kim D. Biomimetic materials replicating Schwann cell topography enhance neuronal adhesion and neurite alignment in vitro. J Biomater Sci Polym Ed 2007;18(8):967-982.

Borschel GH, Kia KF, Kuzon WM, Jr., Dennis RG. Mechanical properties of acellular peripheral nerve. J Surg Res Oct. 2003;114(2):133-139.

Rydevik BL, Kwan MK, Myers RR, Brown RA, Triggs KJ, Woo SLY, et al. An Invitro Mechanical and Histological Study of Acute Stretching on Rabbit Tibial Nerve. Journal of Orthopaedic Research 1990;8(5):694-701.

Guan J, Stankus JJ, Wagner WR. Biodegradable elastomeric scaffolds with basic fibroblast growth factor release. Journal of Controlled Release 2007;120 (1-2) :70-78.

Guan YQ, Tao HM, Li YC, Wang WW, Li ZB, Peng CL. Preparation and activity of a nanometer anti-microbial polyurethane. Journal of Wuhan University of Technology-Materials Science Edition 2009;24(4):540-545.

Wang S, Wan AC, Xu X, Gao S, Mao HQ, Leong KW, et al. A new nerve guide conduit material composed of a biodegradable poly(phosphoester). Biomaterials May 2001;22(10):1157-1169.

Wang W, Itoh S, Matsuda A, Ichinose S, Shinomiya K, Hata Y, et al. Influences of mechanical properties and permeability on chitosan nano/microfiber mesh tubes as a scaffold for nerve regeneration. J Biomed Mater Res a Feb. 2008;84(2):557-566.

Ciardelli G, Rechichi A, Cerrai P, Tricoli M, Barbani N, Giusti P. Segmented polyurethanes for medical applications: Synthesis, characterization and in vitro enzymatic degradation studies. Macromolecular Symposia 2004;218:261-271.

Evans AJ, Thompson BC, Wallace GG, Millard R, O\Leary SJ, Clark GM, et al. Promoting neurite outgrowth from spiral ganglion neuron explants using polypyrrole/BDNF-coated electrodes. J Biomed Mater Res A Oct. 2009;91(1):241-250.

Cho Y, Shi R, Ivanisevic A, Ben Borgens R. A mesoporous silica nanosphere-based drug delivery system using an electrically conducting polymer. Nanotechnology Jul. 8, 2009;20(27):275102.

Guimard NK, Gomez N, Schmidt CE. Conducting polymers in biomedical engineering. Progress in Polymer Science 2007;32:876-921.

Thompson BC, Richardson RT, Moulton SE, Evans AJ, O\Leary S, Clark GM, et al. Conducting polymers, dual neurotrophins and pulsed electrical stimulation—Dramatic effects on neurite outgrowth. J Control Release Sep. 27, 2009.

Cullen DK, A RP, Doorish JF, Smith DH, Pfister BJ. Developing a tissue-engineered neural-electrical relay using encapsulated neuronal constructs on conducting polymer fibers. J Neural Eng Dec. 2008;5(40):374-384.

Cui X, Lee VA, Raphael Y, Wiler JA, Hetke JF, Anderson DJ, et al. Surface modification of neural recording electrodes with conducting polymer/biomolecule blends. J Biomed Mater Res Aug. 2001;56(2):261-272.

Murphy CJ, Jana NR. Controlling the aspect ratio of inorganic nanorods and nanowires. Adv Mater Jan. 2002;14(1):80-82.

Li J, Ma PC, Chow WS, To CK, Tang BZ, Kim JK. Correlations between percolation threshold, dispersion state, and aspect ratio of carbon nanotubes. Advanced Functional Materials 2007;17(16):3207-3215.

Bauhofer W, Kovacs JZ. A review and analysis of electrical percolation in carbon nanotube polymer composites. Composites Science and Technology 2009;69 (10):1486-1498.

Hernandez JJ, Garcia-Gutierrez MC, Nogales A, Rueda DR, Kwiatkowska M, Szymczyk A, et al. Influence of preparation procedure on the conductivity and transparency of SWCNT-polymer nanocomposites. Composites Science and Technology 2009;69(11-12):1867-1872.

Caswell KK, Bender CM, Murphy CJ. Seedless, surfactantless wet chemical synthesis of silver nanowires. Nano Lett May 2003;3(5):667-669.

Gole A, Murphy CJ. Seed-mediated synthesis of gold nanorods: Role of the size and nature of the seed. Chem Mat Sep. 2004;16(19):3633-3640.

De S, Higgins TM, Lyons PE, Doherty EM, Nirmalraj PN, Blau WJ, et al. Silver Nanowire Networks as Flexible, Transparent, Conducting Films: Extremely High DC to Optical Conductivity Ratios. ACS Nano Jul. 2009;3(7):1 767-1774.

Kostarelos K. The long and short of carbon nanotube toxicity. Nature Biotechnology 2008;26(7):774-776.

Lam CW, James JT, McCluskey R, Arepalli S, Hunter RL. A review of carbon nanotube toxicity and assessment of potential occupational and environmental health risks. Critical Reviews in Toxicology 2006;36(3):189-217.

Zhang XP, Sun BQ, Friend RH, Guo HC, Nau D, Giessen H. Metallic photonic crystals based on solution-processible gold nanoparticles. Nano Lett Apr. 2006;6(4):651-655.

Kalbacova M, Kalbac M, Dunsch L, Kataura H, Hempel U. The study of the interaction of human mesenchymal stem cells and monocytes/macrophages with single-walled carbon nanotube films. Phys Status Solidi B-Basic Solid State Phys Nov. 2006;243(13):3514-3518.

Kalbacova M, Kalbac M, Dunsch L, Kromka A, Vanecek M, Rezek B, et al. The effect of SWCNT and nano-diamond films on human osteoblast cells. Phys Status Solidi B-Basic Solid State Phys 2007;244(11):4356-4359.

Hu H, Ni YC, Montana V, Haddon RC, Parpura V. Chemically functionalized carbon nanotubes as substrates for neuronal growth. Nano Lett 2004;4(3):507-511.

Wang LM, Li YF, Zhou LJ, Liu Y, Meng L, Zhang K, et al. Characterization of gold nanorods in vivo by integrated analytical techniques: their uptake, retention, and chemical forms. Anal Bioanal Chem Feb.;396(3):1105-1114.

Chen X, Schluesener HJ. Nanosilver: A nanoproduct in medical application. Toxicol Lett Jan. 2008;176(1):1-12.

Carlson C, Hussain SM, Schrand AM, Braydich-Stolle LK, Hess KL, Jones RL, et al. Unique Cellular Interaction of Silver Nanoparticles: Size-Dependent Generation of Reactive Oxygen Species. J Phys Chem B 2008;112(43):13608-13619.

AshaRani PV, Hande MP, Valiyaveettil S. Anti-proliferative activity of silver nanoparticles. BMC Cell Biol Sep. 2009;10:14.

Alkilany AM, Nagaria PK, Hexel CR, Shaw TJ, Murphy CJ, Wyatt MD. Cellular Uptake and Cytotoxicity of Gold Nanorods: Molecular Origin of Cytotoxicity and Surface Effects. Small Mar. 2009;5(6):701-708.

Bashar SA. Study of Indium Tin Oxide (ITO) for Novel Optoelectronic Devices. King\s College London: University of London; 1998.

(56) References Cited

OTHER PUBLICATIONS

Mitsumoto H, Tsuzaka K. Neurotrophic factors and neuromuscular disease: I. General comments, the neurotrophin family, and neuropoietic cytokines. Muscle Nerve Aug. 1999;22(8):983-999.
Jones DM, Tucker BA, Rahimtula M, Mearow KM. The synergistic effects of NGF and IGF-1 on neurite growth in adult sensory neurons: convergence on the PI 3-kinase signaling pathway. J Neurochem Sep. 2003;86(5):1116-1128.
Sakiyama-Elbert SE, Hubbell JA. Controlled release of nerve growth factor from a heparin-containing fibrin-based cell ingrowth matrix. J Control Release Oct. 3, 2000;69(1)149-158.
Webber CA, Xu Y, Vanneste KJ, Martinez JA, Verge VM, Zochodne DW. Guiding adult Mammalian sensory axons during regeneration. J Neuropathol Exp Neurol Mar. 2008;67(3):212-222.
Xu X, Yee WC, Hwang PY, Yu H, Wan AC, Gao, et al. Peripheral nerve regeneration with sustained release of poly(phosphoester) microencapsulated nerve growth factor within nerve guide conduits. Biomaterials Jun. 2003;24(13):2405-2412.
Boyd JG, Gordon T. A dose-dependent facilitation and inhibition of peripheral nerve regeneration by brain-derived neurotrophic factor. Eur J Neurosci Feb. 2002;15(4):613-626.
Batchelor PE, Porritt MJ, Martinello P, Parish CL, Liberatore GT, Donnan GA, et al. Macrophages and Microglia Produce Local Trophic Gradients That Stimulate Axonal Sprouting Toward but Not beyond the Wound Edge. Mol Cell Neurosci Nov. 2002;21(3):436-453.
Batchelor PE, Wills TE, Hewa AP, Porritt MJ, Howells DW. Stimulation of axonal sprouting by trophic factors immobilized within the wound core. Brain Res May 13, 2008;1209:49-56.
Barras FM, Pasche P, Bouche N, Aebischer P, Zurn AD. Glial cell line-derived neurotrophic factor released by synthetic guidance channels promotes facial nerve regeneration in the rat. J Neurosci Res Dec. 15, 2002;70(6):746-755.
Ohta M, Suzuki Y, Chou H, Ishikawa N, Suzuki S, Tanihara M, et al. Novel heparin/alginate gel combines with basic fibroblast growth factor promotes nerve regeneration in rat sciatic nerve. J Biomed Mater Res A Dec. 15, 2004;71(4):661-668.
Winseck AK, Caldero J, Ciutat D, Prevette D, Scott SA, Wang G, et al. In vivo analysis of Schwann cell programmed cell death in the embryonic chick: regulation by axons and glial growth factor. J Neurosci Jun. 1, 2002;22(11):4509-4521.
Bryan DJ, Holway AH, Wang KK, Silva AE, Trantolo DJ, Wise D, et al. Influence of glial growth factor and Schwann cells in a bioresorbable guidance channel on peripheral nerve regeneration. Tissue Eng Apr. 2000;6(2):129-138.
Zurn AD, Winkel L, Menoud A, Djabali K, Aebischer P. Combined effects of GDNF, BDNF, and CNTF on motoneuron differentiation in vitro. J Neurosci Res Apr. 15, 1996;44(2):133-141.
Bailey SB, Eicheler ME, Villadiego A, Rich KM. The influence of fibronectin and laminin during Schwann cell migration and peripheral nerve regeneration through silicon chambers. J Neurocytol Mar. 1993;22(3):176-184.
Woolley AL, Hollowell JP, Rich KM. First place Resident Basic Science Award 1990. Fibronectin-laminin combination enhances peripheral nerve regeneration across long haps. Otolaryngol Head Neck Surg Oct. 1990;103(4):509-518.
Dertinger SK, Jiang X, Li Z , Murthy VN, Whitesides GM. Gradients of substrate-bound laminin orient axonal specification of neurons. Proc Natl Acad Sci U S A Oct. 1, 2002;99(20):12542-12547.
Li GN, Liu J, Hoffman-Kim D. Multi-molecular gradients of permissive and inhibitory cues direct neurite outgrowth. Ann Biomed Eng Jun. 2008;36 (6):889-904.
Sta Iglesia DD, Cragoe EJ, Jr., Vanable JW, Jr. Electric field strength and epithelization in the newt (Notophthalmus viridescens). J Exp Zool Jan. 1, 1996;274 (1):56-62.
Sta Iglesia DD, Vanalbe JW, Jr. Endogenous lateral electric fields around bovine corneal lesions are necessary for and can enhance normal rates of wound healing. Wound Repair Regen Nov.-Dec. 1998;6(6):531-542.
Song B, Zhao M, Forrester J, McCaig C. Nerve regeneration and wound healing are stimulated and directed by an endogenous electrical field in vivo. Journal of Cell Science 2004;117(20):4681-4690.
Chiang M, Robinson KR, Vanable JW, Jr. Electrical fields in the vicinity of epithelial wounds in the isolated bovine eye. Exp Eye Res Jun. 1992;54(6):999-1003.
Huang J, Hu X, Lu L, Ye Z, Zhang Q, Luo Z. Electrical regulation of Schwann cells using conductive polypyrrole/chitosan polymers. J Biomed Mater Res A Jun. 17, 2009.
Supronowicz PR, Ajayan PM, Ullmann KR, Arulanandam BP, Metzger DW, Bizios R. Novel current-conducting composite substrates for exposing osteoblasts to alternating current stimulation. J Biomed Mater Res Mar. 5, 2002;59(30):499-506.
Borgens RB, Vanable JW, Jr. Jaffe LF. Bioelectricity and regeneration: large currents leave the stumps of regenerating newt limbs. Proc Natl Acad Sci U S A Oct. 1997;74(10):4528-4532.
Al-Majed AA, Neumann CM, Brushart TM, Gordon T. Brief electrical stimulation promotes the speed and accuracy of motor axonal regeneration. J Neurosci Apr. 1, 2000;20(7):2602-2608.
Marsh G, Beams HW. In Vitro Contorl of Growing Chick Nerve Fibers by Applied Electric Currents. Journal of Cellular and Comparative Physiology 1946;27:139-157.
Macias MY, Battocletti JH, Sutton CH, Pintar FA, Maiman DJ. Directed and enhanced neurite growth with pulsed magnetic field stimulation. Bioelectromagnetics May 2000;21(4):272-286.
Zhao M, Dick A, Forrester JV, McCaig CD. Electric field-directed cell motility involves up-regulated expression and asymmetric redistribution of the epidermal growth factor receptors and is enhanced by fibronectin and laminin. Molecular Biology of the Cell 1999;10(4):1259-1276.
Rajnicek AM, Robinson KR, McCaig CD. The direction of neurite growth in a weak DC electric field depends on the substratum: Contributions of adhesivity and net surface charge. Dev Biol Nov. 1998;203(2):412-423.
McCaig CD, Sangster L, Stewart R. Neurotrophins enhance electric field-directed growth cone guidance and directed nerve branching. Dev Dyn Mar. 2000;217 (3):299-308.
Evans PJ, Bain JR, Mackinnon SE, Makino AP, Hunter DA. Selective reinnervation: a comparison of recovery following microsuture and conduit nerve repair. Brain Res Sep. 20, 1991;559(2):315-321.
Wang S, Cai Q, Hou J, Bei J, Zhang T, Yang J, et al. Acceleration effect of basic fibroblast growth factor on the regeneration of peripheral nerve through a 15-mm gap. J Biomed Mater Res A Sep. 1, 2003;66(3):522-531.
Vleggeert-Lankamp CL. The role of evaluation methods in the assessment of peripheral nerve regeneration through synthetic conduits: a systematic review. Laboratory investigation. J Neurosurg Dec. 2007; 107(6):1168-1189.
Chamberlain LJ, Yannas IV, Hsu HP, Strichartz GR, Sepctor M. Near-terminus axonal structure and function following rat sciatic nerve regeneration through a collagen-GAG matrix in a ten-millimeter gap. J Neurosci Res Jun. 1, 2000;610(5):666-677.
Fine EG, Decosterd I, Papaloizos M, Zurn AD, Aebischer P. GDNF and NGF released by synthetic guidance channels support sciatic nerve regeneration across a long gap. Eur J Neurosci Feb. 2002;15(4):589-601.
Udina E, Furey M, Busch S, Silver J, Gordon T, Fouad K. Electrical stimulation of intact peripheral sensory axons in rats promotes outgrowth of their central projections. Exp Neurol Mar. 2008;210(1):238-247.
Al-Majed AA, Brushart TM, Gordon T. Electrical accelerates and increases expression of BDNF and trkB Mrna in regenerating rat femoral motoneurons. Eur J Neurosci Dec. 2000;12(12):4381-4390.
Al-Majed AA, Tam SL, Gordon T. Electrical stimulation accelerates and enhances expression of regeneration-associated genes in regenerating rat femoral motoneurons. Cell Mol Neurobiol Jun. 2004;24(3):379-402.
Zhang J, Lineaweaver WC, Oswald T, Chen Z, Zhang F. Ciliary neurotrophic factor for acceleration of peripheral nerve regeneration: an experimental study. J Reconstr Microsurg May 2004;20(4):323-327.

(56) References Cited

OTHER PUBLICATIONS

Varejao AS, Melo-Pinto P, Meek MF, Filipe VM, Bulas-Cruz J. Methods for the experimental functional assessment of rat sciatic nerve regeneration. Neurol Res Mar. 2004;26(2):186-194.

Varejao AS, Cabrita AM, Geuna S, Melo-Pinto P, Filipe VM, Gramsbergen A, et al. Toe out angle: a functional index for the evaluation of sciatic nerve recovery in the rat model. Exp Neurol Oct. 2003;183(20):695-699.

Song YX, Muramatsu K, Kurokawa Y, Kuriyama R, Sakamoto S, Kaneko K, et al. Functional recovery of rat hind-limb allografts. J Reconstr Microsurg Oct. 2005;21 (7):471-476.

Bain JR, Mackinnon SE, Hunter DA. Functional evaluation of complete sciatic, peroneal, and posterior tibial nerve lesions in the rat. Plast Reconstr Surg Jan. 1989;83(1):129-138.

Luis AL, Rodrigues JM, Lobato JV, Lopes MA, Amado S, Veloso AP, et al. Evaluation of two biodegradable nerve guides for the reconstruction of the rat sciatic nerve. Biomed Mater Eng 2007;17(1):39-52.

Gonzalez-Billault C, Jimenez-Mateos EM, Caceres A, Diaz-Nido J, Wandosell F, Avila J. Microtube-associated protein 1B function during normal development, regeneration, and pathological conditions in the nervous system. J Neurobiol Jan. 2004;58(1):48-59.

Pigino G, Paglini G, Ulloa L, Avila J, Caceres A. Analysis of the expression, distribution and function of cyclin dependent kinase 5 (cdk5) in developing cerebellar macroneurons. J Cell Sci Jan. 1997;110 (Pt 2):257-270.

Franzen R, Tanner SL, Dashiell SM, Rottkamp CA, Hammer JA, Quarles RH. Microtubule-associated protein 1 B: a neuronal binding partner for myelin-associated glycoprotein. J Cell Biol Dec. 10, 2001;155(6):893-898.

Riederer BM, Moya F, Calvert R. Phosphorylated MAP1b, alias MAP5 and MAP1x, is involved in axonal growth and neuronal mitosis. Neuroreport Jun. 1993;4(6):771-774.

Bouquet C, Ravaille-Veron M, Propst F, Nothias F. MAP1B coordinates microtubule and actin filament remodeling in adult mouse Schwann cell tips and DRG neuron growth cones. Mol Cell Neurosci Oct. 2007;36(2):235-247.

Garcia-Perez J, Avila J, Diaz-Nido J. Implication of cyclin-dependent kinases and glycogen synthase kinase 2 in the phosphorylation of microtubule-associated protein 1B in developing neuronal cells. J Neurosci Res May 15, 1998;52(4):445-452.

Goold RG, Gordon-Weeks PR. The Map kinase pathway is upstream of the activation of GSK3beta that enables it to phosphorylate MAP1B and contributes to the stimulation of axon growth. Mol Cell Neurosci Mar. 2005;28(3):524-534.

Goold RG, Gordon-Weeks PR. Glycogen synthase kinase 3beta and the regulation of axon growth. Biochem Soc Trans Nov. 2004;32(Pt 5):809-811.

Goold RG, Gordon-Weeks PR. NGF activates the phosphorylation of MAP1B by GSK3beta through the TrkA receptor and not the p75(NTR) receptor. J Neurochem Nov. 2003;87(4):935-946.

Cheng C, Webber CA, Wang J, Xu Y, Martinez JA, Liu WQ, et al. Activated RHOA and peripheral axon regeneration. Exp Neurol Aug. 2008;212(2):358-369.

Gallo G. RhoA-kinase coordinates F-actin organization and myosin II activity during semaphoring-3A-induced axon retraction. J Cell Sci Aug. 15, 2006;119(Pt 16):3413-3423.

Loudon RP, Silver LD, Yee HF, Jr., Gallo G. RhoA-kinase and myosin II are required for the maintenance of growth cone polarity and guidance by nerve growth factor. J Neurobiol Jul. 2006;66(8):847-867.

Melendez-Vasquez CV, Einheber S, Salzer JL. Rho kinase regulates Schwann cell myelination and formation of associated axonal domains. J Neurosci Apr. 21, 2004;24(16):3953-3963.

Sherman DL, Brophy PJ. Mechanisms of axon ensheathment and myelin growth. Nat Rev Neurosci Sep. 2005;6(9):683-690.

Sharma N, Marzo SJ, Jones KJ, Foecking EM. Electrical stimulation and testosterone differentially enhance expression of regeneration-associated genes. Exp Neurol May 7, 2009.

Tsujino H, Kondo E, Fukuoka T, Dai Y, Tokunaga A, Miki K, et al. Activating transcription factor 3 (ATF3) induction by axotomy in sensory and motoneurons: A novel neuronal marker of nerve injury. Mol Cell Neurosci Feb. 2000;15(2):170-182.

Geremia NM, Gordon T, Brushart TM, Al-Majed AA, Verge VM. Electrical stimulation promotes sensory neuron regeneration and growth-associated gene expression. Exp Neurol Jun. 2007;205(2):347-359.

McIntyre CC, Richardson AG, Grill WM. Modeling the excitability of mammalian nerve fibers: influence of afterpotentials on the recovery cycle. J Neurophysiol Feb. 2002;87(2):995-1006.

Shanthaveerappa TR, Bourne GH. Histological and histochemical studies of the choroid of the eye and its relations to the pia-arachnoid mater of the central nervous system and perineural epithelium of the peripheral nervous system. Acta Anat (Basel) 1965;61(3):379-398.

Jana NR, Gearheart L, Murphy CJ. Wet chemical synthesis of high aspect ratio cylindrical gold nanorods. J Phys Chem B May 2001;105(19):4065-4067.

Johnson EO, Soucacos PN. Nerve repair: experimental and clinical evaluation of biodegradable artificial nerve guides. Injury Sep. 2008;39 Suppl 3:S30-36.

Hudson TW, Evans GR, Schmidt CE. Engineering strategies for peripheral nerve repair. Orthop Clin North Am Jul. 2000;31(3):485-498.

Wang S, Yaszemski MJ, Knight AM, Gruetzmacher JA, Currier BL, Yaszemski MJ. Synthesis and characterizations of biodegradable and crosslinkable poly(epsilon-caprolactone fumarate), poly(ethylene glycol fumarate), and their amphiphilic copolymer. Biomaterials Feb. 2006;27(6):832-841.

Wang S, Yaszemski MJ, Knight AM, Gruetzmacher JA, Windebank AJ, Lu L. Photo-crosslinked poly(epsilon-caprolactone fumarate) networks for guided peripheral nerve regeneration: material properties and preliminary biological evaluations. Acta Biomater Jun. 2009;5(5):1531-1542.

Hadlock T, Sundback C, Hunter D, Cheney M, Vacanti JP. A polymer foam conduit seeded with Schwann cells promotes guided peripheral nerve regeneration. Tissue Engineering 2000;6(20)119-127.

Chang CJ, Hsu SH, Yen HJ, Chang H, Hsu SK. Effects of unidirectional permeability in asymmetric poly(DL-lactic acid-co-glycolic acid) conduits on peripheral nerve regeneration: an in vitro and in vivo study. J Biomed Mater Res Part B Oct. 2007;83B(1):206-215.

Hollowell JP, Villadiego A, Rich KM. Sciatic nerve regeneration across gaps within silicone chambers: long-term effects of NGF and consideration of axonal branching. Exp Neurol Oct. 1990;110(1):45-51.

Lietz M, Dreesmann L, Hoss M, Oberhoffner S, Schlosshauer B. Neuro tissue engineering of glial nerve guides and the impact of different cell types. Biomaterials Mar. 2006;27(8):1425-1436.

Song J, Cheng Q, Kopta S, Stevens RC. Modulating artificial membrane morphology: pH-induced chromatic transition and nanostructural transformation of a bolaamphiphilic conjugated polymer from blue helical ribbons to red nanofibers. J Am Chem Soc Apr. 11, 2001;123(14):3205-3213.

Kehoe S, Zhang XF, Boyd D. FDA approved guidance conduits and wraps for peripheral nerve injury: A review of materials and efficacy. Injury-Int J Care Inj May;43(5):553-572.

Pomerantseva I, Krebs N, Hart A, Neville CM, Huang AY, Sundback CA. Degradation behavior of poly(glycerol sebacate). J Biomed Mater Res Part A Dec. 2009;91A(4):1038-1047.

Wang YD, Ameer GA, Sheppard BJ, Langer R. A tough biodegradable elastomer. Nature Biotechnology Jun. 2002;20(6):602-606.

Nijst CLE, Bruggeman JP, Karp JM, Ferreira L, Zumbuehl A, Bettinger CJ, et al. Synthesis and characterization of photocurable elastomers from poly(glycerol-co-sebacate). Biomacromolecules Oct. 2007;8(10):3067-3073.

Gerecht S, Townsend SA, Pressler H, Zhu H, Nijst CLE, Bruggeman JP, et al. A porous photocurable elastomer for cell encapsulation and culture. Biomaterials Nov. 2007;28(32):4826-4835.

(56) References Cited

OTHER PUBLICATIONS

Svennersten K, Bolin MH, Jager EWH, Berggren M, Richter-Dahlfors A. Electrochemical modulation of epithelia formation using conducting polymers. Biomaterials Nov. 2009;30(31):6257-6264.

Luo XL, Weaver CL, Zhou DD, Greenberg R, Cui XYT. Highly stable carbon nanotube doped poly(3,4-ethylenedioxythiophene) for chronic neural stimulation. Biomaterials Aug.;32(24):5551-5557.

Abidian MR, Martin DC. Experimental and theoretical characterization of implantable neural microelectrodes modified with conducting polymer nanotubes. Biomaterials Mar. 2008;29(9):1273-1283.

Edwards SL, Church JS, Werkmeister JA, Ramshaw JAM. Tubular micro-scale multiwalled carbon nanotube-based scaffolds for tissue engineering. Biomaterials Mar. 2009;30(9):1725-1731.

Shi GX, Rouabhia M, Wang ZX, Dao LH, Zhang Z. A novel electrically conductive and biodegradable composite made of polypyrrole nanoparticles and polylactide. Biomaterials Jun. 2004;25(13):2477-2488.

George PM, Lyckman AW, LaVan DA, Hegde A, Leung Y, Avasare R, et al. Fabrication and biocompatibility of polypyrrole implants suitable for neural prosthetics. Biomaterials Jun. 2005;26(17):3511-3519.

Ifkovits JL, Devlin JJ, Eng G, Martens TP, Vunjak-Novakovic G, Burdick JA. Biodegradable Fibrous Scaffolds with Tunable Properties Formed from Photo-Cross-Linkable Poly(glycerol sebacate). ACS Appl Mater Interfaces Sep. 2009;1(9):1878-1886.

Liu QY, Tian M, Ding T, Shi R, Feng YX, Zhang LQ, et al. Preparation and characterization of a thermoplastic poly(glycerol sebacate) elastomer by two-step method. J Appl Polym Sci Feb. 2007;103(3):1412-1419.

Evans GR. Challenges to nerve regeneration. Semin Surg Oncol Oct.-Nov. 2000;19(3):312-318.

Chamberlain LJ, Yannas IV, Hsu HP, Strichartz GR, Spector M. Near-terminus axonal structure and function following rat sciatic nerve regeneration through a collagen-GAG matrix in a ten-millimeter gap. J Neurosci Res Jun. 1, 2000;60(5):666-677.

Zhang DH, Kandadai MA, Cech J, Roth S, Curran SA. Poly(L-lactide) (PLLA)/multiwalled carbon nanotube (MWCNT) composite: Characterization and biocompatibility evaluation. J Phys Chem B 2006;110(26):12910-12915.

Schense JC, Bloch J, Aebischer P, Hubbell JA. Enzymatic incorporation of bioactive peptides into fibrin matrices enhances neurite extension. Nature Biotechnology Apr. 2000;18(4):415-419.

Chen YS, Hsieh CL, Tsai CC, Chen TH, Cheng WC, Hu CL, et al. Peripheral nerve regeneration using silicone rubber chambers filled with collagen, laminin and fibronectin. Biomaterials Aug. 2000;21(15):1541-1547.

Evans GRD, Brandt K, Katz S, Chauvin P, Otto L, Bogle M, et al. Bioactive poly(L-lactic acid) conduits seeded with Schwann cells for peripheral nerve regeneration. Biomaterials Feb. 2002;23(3):841-848.

Goldner JS, Bruder JM, Li G, Gazzola D, Hoffman-Kim D. Neurite bridging across micropatterned grooves. Biomaterials Jan. 2006;27(3):460-472.

Abrams GA, Goodman SL, Nealey PF, Franco M, Murphy CJ. Nanoscale topography of the basement membrane underlying the corneal epithelium of the rhesus macaque. Cell Tissue Res Jan. 2000;299(1):39-46.

Miller C, Jeftinija S, Mallapragada S. Micropatterned Schwann cell-seeded biodegradable polymer substrates significantly enhance neurite alignment and outgrowth. Tissue Engineering Dec. 2001;7(6):705-715.

Zhao M, AgiusFernandez A, Forrester JV, McCaig CD. Orientation and directed migration of cultured corneal epithelial cells in small electric fields are serum dependent. Journal of Cell Science Jun. 1996;109:1405-1414.

Zhao M, McCaig CD, AgiusFernandez A, Forrester JV, ArakiSasaki K. Human corneal epithelial cells reorient and migrate cathodally in a small applied electric field. Current Eye Research 1997;16(10):973-984.

Baron-Van Evercooren A, Kleinman HK, Ohno S, Marangos P, Schwartz JP, Dubois-Dalcq ME. Nerve growth factor laminin and fibronective promote neurite growth in human fetal sensory ganglia cultures. Journal of Neuroscience Research 1982;8(2-3):179-194.

Cheng H, Hoffer B, Stromberg I, Russell D, Olson L. The effect of glial-cell line-derived neurotrophic factor in fibrin glue on developing dopamine neurons. Exp Brain Res May 1995;104(2):199-206.

Edelman ER, Mathiowitz E, Langer R, Klagsbrun M. Controlled and modulated release of basic fibroblast growth factor. Biomaterials Sep. 1991;12(7):619-626.

McDonald, D.S. & Zochodne, D.W. An injectable nerve regeneration chamber for studies of unstable soluble growth factors. Journal of Neuroscience Methods 122, 171-178 (2003).

Phillips,J.B., Bunting, S.C.J., Hall ,S.M. & Brown, R.A. Neural tissue engineering: A self-organizing collagen guidance conduit. Tissue Engineering 11, 1611-1617 (2005).

Jubran,M. & Widenfalk, J. Repair of peripheral nerve transections with fibrin sealant containing neurotrophic factors. Experimental Neurology 181, 204-212 (2003).

Foley,J.D., Grunwald, E.W., Nealey, P.F. & Murphy, C.J. Cooperative modulation of neuritogenesis by PC12 cells by topography and nerve growth factor. Biomaterials 26, 3639-3644 (2005).

Yusuka Katayama et al. Coil-Reinforced hydrogel tubes promote nerve regeneration equivalent to that of nerve autografts. Biomaterials 27, 503-518 (2006).

Yuan, Y., Zhang, P., Yang, Y., Wang, X. & Gu, X. The interaction of Schwann cells with chitosan membranes and fibers in vitro. Biomaterials 25, 4273-4278 (2004).

Evans, G.R.D. et al. In vivo evaluation of poly(-lactic acid) porous conduits for peripheral nerve regeneration. Biomaterials 20, 1109-1115 (1999).

Lietz, M. et al. Physical and biological performance of a novel block copolymer nerve guide. Biotechnology and Bioengineering 93, 99-109 (2006).

Keilhoff,G., Stang, F., Wolf, G. & Fansa, H. Bio-compatibility of type I/III collagen matrix for peripheral nerve reconstruction. Biomaterials 24, 2779-2787 (2003).

Jain, a., Kim, Y.T., Mckeon, R.J. & Bellamkonda, R.V. In situ gelling hydrogels for conformal repair of spinal cord defects, and local delivery of BDNF after spinal cord injury. Biomaterials 27, 497-504 (2006).

Li, M., Guo, Y., Wei, Y., MacDiarmid, A.G. & Lelkes, P.I. Electrospinning polyaniline-contained gelatin nanofibers for tissue engineering applications. Biomaterials 27, 2705-2715 (2006).

Novikova,L.N. et al. Alginate hydrogel and matrigel as potential cell carriers for neurotransplantation. Journal of Biomedical Materials Research Part A 77A, 242-252 (2006).

Al Majed, A.A., Tam, S.L. & Gordon, T. Electrical stimulation accelerates and enhances expression of regeneration-associated genes in regenerating rat femoral motoneurons. Cellular and Molecular Neurobiology 24, 379-402 (2004).

Brushart, T.M., Jari, R., Verge, V., Rohde, C. & Gordon, T. Electrical stimulation restores the specificity of sensory axon regeneration. Experimental Neurology 194, 221-229 (2005).

Ming, G.I., Henley, J., Tessier-Lavigne, M., Song, H.J. & Poo, M.m. Electrical Activity Modulates Growth Cone Guidance by Diffusible Factors. Neuron 29, 441-452 (2001).

Terell Rivers, Terry Hudson & Christine Schmidt. Synthesis of a Novel, Biodegradable Electrically Conducting Polymer for Biomedical Applications. Advanced Functional Materials 12, 33-37 (2002).

Kotwal, A. & Schmidt, C.E. Electrical stimulation alters protein adsorption and nerve cell interactions with electrically conducting biomaterials. Biomaterials 22, 1055-1064 (2001).

Yang, L., Feng, J.K. & Ren, A.M. Structural, electronic and optical properties of a series of oligofluorene-thiophene oligomers and polymers. Journal of Molecular Structure-Theochem 758, 29-39 (2006).

(56) References Cited

OTHER PUBLICATIONS

Suzuki, M., Fukuyama, M., Hori, Y. & Hotta, S. Electroluminescent features of oligothiophenes dispersed as a dopant in host matrices. Journal of Applied Physics 91, 5706-571 1 (2002).
Xu, H. et al. High-performance field-effect transistors based on Langmuir-Blodgett films of cyclo[8]pyrrole. Langmuir 21, 5391-5395 (2005).
Jin, Z., Pramoda, K.P., Xu, G. & Goh, S.H. Dynamic mechanical behavior of meltprocessed multi-walled carbon nanotubelpoly(methyl methacrylate) composites. Chemical Physics Letters 337, 43-47 (2001).
Webster, T.J., Waid, M.C., McKenzie, J.L., Price, R.L. & Ejiofor, J.U. Nanobiotechnology: carbon nanofibres as improved neural and orthopaedic implants. Nanotechnology 15, 48-54 (2004).
Wei, G. et al. One-step synthesis of silver nanoparticles, nanorods, and nanowires on the surface of DNA network. Journal of Physical Chemistry B 109, 8738-8743 (2005).
Murphy, C.J., Gole, A.M., Hunyadi, S.E. & Orendorff, C.J. One-dimensional colloidal gold and silver nanostructures. Inorganic Chemistry 45,7544-7554 (2006).
Orendorff, C.J., Gearheart, L., Jana, N.R. & Murphy, C.J. Aspect ratio dependence on surface enhanced Raman scattering using silver and gold nanorod substrates. Physical Chemistry Chemical Physics 8, 165-170 (2006).
Elias, K.L., Price, R.L. & Webster, T.J. Enhanced functions of osteoblasts on nanometer diameter carbon fibers. Biomaterials 23, 3279-3287 (2002).
Min, B.M., You, Y., Kim, J.M., Lee, S.J. & Park, W.H. Formation of nanostructured poly(lactic-co-glycolic acid)/chitin matrix and its cellular response to normal human keratinocytes and fibroblasts. Carbohydrate Polymers 57, 285-292 (2004).
Hu, H. et al. Polyethyleneimine functionalized single-walled carbon nanotubes as a substrate for neuronal growth. Journal of Physical Chemistry B 109, 4285-4289 (2005).
Mattson, M.P., Haddon, R.C. & Rao, A.M. Molecular functionalization of carbon nanotubes and use as substrates for neuronal growth. Journal of Molecular Neuroscience 14, 175-182 (2000).
Ni, Y.C. et al. Chemically functionalized water soluble single-walled carbon nanotubes modulate neurite outgrowth. Journal of Nanoscience and Nanotechnology 5, 1707-171 2 (2005).
Lansdown, A.B.G. Critical observations on the neurotoxicity of silver. Critical Reviews in Toxicology 37, 237-250 (2007).
Schmidt, C.E. Ann Rev Biomed Engr 5:293-347 (2003).
Rosenbalm, T., Levi-Polyachenko, N., and Wagner, W.D. Development of repeated biphasic conducting materials for peripheral nerve repair. Gordon Conference on Biochemistry, the Complex Membrane of the Electric Field, University of New England, Biddeford, ME (Jul. 11-16, 2010).
Oh, et al. High molecular weight soluble polypyrrole. Synthetic Metals 125: 267-272 (2002).
Taunk, M. et al. Hopping and tunneling transport over a wide temperature range in chemically synthesized doped and undoped polypyrrole. Solid State Communications 150: 1766-1769 (2010).
Yen, S-J et al. Preparation and characterization of polypyrrole/magnetite nanocomposites synthesized by in situ chemical oxidative polymerization. Journal of Polymer Sciences B: Polymer Physics 46: 1291-1300 (2008).
Lu, X. et al. Preparation and characterization of conducting polycaprolactone/chitosan/polypyrrole composites. Composites: Part A. 41: 1516-1523 (2010).
Oh, S.H. et al. Peripheral nerve regeneration within an asymmetrically porous PLGA/Pluronic F127 nerve guide conduit. Biomaterials 29: 1601-1609 (2008).
Oh, E.J. et al. Synthesis and characterization of high molecular weight, highly soluble polypyttole in organic solvents. Syntheic Metals 119: 109-110 (2001).
Shi, G. et al. A novel electrically conductive and biodegradable composite made of polypyrrole nanoparticles and polylactide. Biomaterials 25: 2477-2488 (2004).
Thomas, C.A. et al. Poly(3,4-alkylenedioxypyrrole)s as highly stable aqueous-compatible conducting polymers with biomedical implications. Adv. Mater 12: 222 (2000).
Wan, Y. et al. Porous-conductive chitosan scaffolds for tissue engineering II. in vitro and in vivo degradation. Journal of Materials Science: Materials in Medicine 16: 1017-1028 (2005).
Wan, Y. et al. Porous-Conductive Scaffolds for Tissue Engineering, 1: Preparation and Characterization. Macromol. Biosci. 4: 882-890 (2004).
Wang, Z. et al. In vivo evaluation of a novel electrically conductive polypyrrole/poly(D,L-lactide) composite and polypyrrole-coated poly(D,L-lactide-co-glycolide) membranes. J. Biomed Mater Res 70A: 28-38 (2004).
Yan, F. et al. Preparation of electrically conducting polypyrrole in oil/water microemulsion. J Appl Polym Sci 77: 135-140 (2000).
Stryker. Stryker Neuromatrix. 2009; Available from: http://www.stryker.com/en-us/products/Trauma/PeripheralNerveRepair/NeuroMatrix/index.htm.
Integra. NeuraGen Nerve Guide. 2009; Available from: http://www.integra-ls.com/products/?product=88.
Stryker. Stryker Neuroflex. 2009; Available from: http://www.stryker.com/en-us/products/Trauma/PeripheralNerveRepair/Neuroflex/index.htm.
Polyganics. Neurolac. 2009; Available from: http://www.polyganics.nl/index.php?id=19.
Synovis Micro Companies Alliance I. GEM Neurotube. 2009; Available from: http://www.synovismicro.com/gem_neurotube.php.
Integra. NeuraWrap Nerve Protector. 2009; Available from: http://www.integra-Is.com/products/?product=198.
SaluMedica. SaluBridge Physician Information. 2009; Available from: http://www.salumedica.com/salubridgeinfodoc.htm.
Barrett, DG and Yousaf, MN. Design and Applications of Biodegradable Polyester Tissue Scaffolds Based on Endogenous Monomers Found in Human Metabolism. Molecules, Oct. 12, 2009.
Dumitriu, Severian and Popa, Valentin. Polymeric Biomaterials: Structure and Function, vol. 1. Boca Raton, FL: CRC Press, Jan. 17, 2013.
International Search Report and Written Opinion from International Application No. PCT/US15/54484 dated Jan. 6, 2016.
Supplementary European Search Report for EP13849526 dated May 25, 2016.
Wang, R et al. "Evaluation of Repeated Biphasic Conducting Materials for Peripheral Nerve Repair" and "Injectable and Self-Assembling Sponge as a Protective Layer at Device-Tissue Interfaces in Wound Repair." BMES, 12th Annual Graduate Student Research Symposium. May 16, 2013.
Subramanian et al, Development of biomaterial scaffold for nerve tissue engineering: Biomaterial mediated neural regeneration, Journal of Biomedical Science, 2009, 16, pp. 1-11.
Yu et al, Promoting neuron adhesion and growth, Materials today, 2008, 11, pp. 36-43.
Widmer et al, Manufacture of porous biodegradable polymer conduits by an extrusion process for guided tissue regeneration, Biomaterials, 1998, 19, pp. 1945-1955.
Chen et al, Development of biodegradable porous scaffolds for tissue engineering, Materials Science and Engineering C, 2001, 17, pp. 63-69.
Lee et al, In vivo conjunctival reconstruction using modified PLGA grafts for decreased scar formation and contraction, Biomaterials, 2003, 24, pp. 5049-5059.
Cytometrics, from http://www.nanomedicine.com/NMI/8.5.1.htm, pp. 1-2, accessed Jul. 5, 2016.
May, The Effects of Biological Wound Dressings on the Healing Process,National Tissue Services, American Red Cross, 1991;8(3-4):243-9.
Salisbury et al., Biological Dressings and Evaporative Water Loss from Burn Wounds, Annals of Plastic Surgery vol. S No. 4 Oct. 1980, pp. 270-272.
Calvin et al., Microstructure and Mechanics of the Chorioamnion Membrane with an Emphasis on Fracture Properties, vol. 1101, Reproductive Biomechanics pp. 166-185, Apr. 2007.

(56) References Cited

OTHER PUBLICATIONS

Kenar et al. (2010). Design of 3D aligned mycoardial tissue construct from biodegradable polyesters. J. Mater. Med 21:989-997.
Yang et al., "Electrospinning of nano/micro scale poly(L-lactic acid) aligned fibers and their potential in neural tissue engineering," Biomaterials 260:2603-2610 (2005).
Tao Xua, et al., Viability and electrophysiology of neural cell structures generated by the inkjet printing method, Biomaterials 27 (2006) 3580-3588, Jan. 2006.
Scott J.Hollister, Porous scaffold design for tissue engineering, Nature Materials vol. 4 Jul. 2005.
Banani Kundu et al., Thromboelastometric and platelet responses to silk biomaterials, Scientific Reports, pp. 1-9, May 2014.
R. W. Farndale et al., The role of collagen in thrombosis and hemostasis, Journal of Thrombosis and Haemostasis, 2: 561-573 , 2004.
Wei Wu, Ph.D. et al., Artificial Niche Combining Elastomeric Substrate and Platelets Guides Vascular Differentiation of Bone Marrow Mononuclear Cells, Tissue Engineering: Part A vol. 17, Nos. 15 and 16, 2011.
Extended European Search Report from European Patent Application No. 13775894.2, dated Nov. 27, 2015.
Motlagh et al. (2006) "Hemocompatibility Evaluation of Poly(glycerol-sebacate) in vitro for vascular tissue engineering", Biomaterials 27(24): 4315-4324.
Wang et al. (2012) "Novel Nanofiber-based Graft for Heart Valve Replacement," Thesis for Master of Science, Biomedical Engineering, Wake Forest University Dec. 12, 2012.
International Search Report from International Application No. PCT/US2013/066747, dated Dec. 20, 2013.
Written Opinion from International Application No. PCT/US2013/066747, dated Dec. 20, 2013.
International Preliminary Report on Patentability from International Application No. PCT/US2013/066747, dated Apr. 28, 2015.
Lang et al. (2014) "A blood-resistant surgical glue for minimally invasive repair of vessels and heart defects," Science Translational Medicine, 6(218): 1-6.
Liu, Y., et al., "Engineering of bio-hybrid materials by electrospinning polymer-microbe fibers," P. Natl. Acad. Sci. USA 106(34):14201-14206 (Aug. 25, 2009).
Abdel-Fattah, W.I., et al., "Synthesis, characterization of chitosans and fabrication of sintered chitosan microsphere matrices for bone tissue engineering," Acta Biomaterialia 3:503-514 (2007).
Apte, S. S. (2011). "Current developments in the tissue engineering of autologous heart valves: moving towards clinical use." Future cardiology 7(1): 77-97.
Barakat, N.A.M., et al., "Polymeric nanofibers containing solid nanoparticles prepared by electrospinning and their applications," Chemical Engineering Journal 156:487-495 (2010).
Beachley, V., et al., "Polymer nanofibrous structures: Fabrication, biofunctionalization, and cell interactions," Progress in Polymer Science, 35(7):868-892 (Jul. 2010) (available online Mar. 17, 2010).
Beun, L. H., X. J. Beaudoux, et al. (2011). "Self-Assembly of Silk-Collagen-like Triblock Copolymers Resembles a Supramolecular Living Polymerization." ACS Nano 6(1): 133-140.
Billiar, K. L. and M. S. Sacks (2000). "Biaxial Mechanical Properties of the Native and Glutaraldehyde-Treated Aortic Valve Cusp: Part II—A Structural Constitutive Model." Journal of Biomechanical Engineering 122(4): 327-335.
Boissard, C.I.R., et al., "Nanohydroxyapatite/poly(ester urethane) scaffold for bone tissue engineering," Acta Biomaterialia 5:3316-3327 (Nov. 2009; available online May 12, 2009).
Boland, E.D., et al., "Electrospinning polydioxanone for biomedical applications," Acta Biomaterialia 1:115-123 (2005).
Bondar, B., S. Fuchs, et al. (2008). "Functionality of endothelial cells on silk fibroin nets: Comparative study of micro- and nanometric fibre size." Biomaterials 29(5): 561-572.
Breuer, C. K. (2004). "Application of tissue-engineering principles toward the development of a semilunar heart valve substitute." Tissue engineering 10 (11-12): 1725-1736.

Butcher, J. T., G. J. Mahler, et al. (2011). "Aortic valve disease and treatment: The need for naturally engineered solutions." Advanced Drug Delivery Reviews 63 (4-5): 242-268.
Causa, F., et al., "A multi-functional scaffold for tissue regeneration: The need to engineer a tissue analogue," Biomaterials, 28(34):5093-5099 (Dec. 2007; available online Aug. 6, 2007).
Cebotari, S. (2011). "Use of fresh decellularized allografts for pulmonary valve replacement may reduce the reoperation rate in children and young adults: early report." Circulation (New York, N.Y.) 124(11 suppl): S115-123.
Chen, D., et al., "Application of electrostatic spinning technology in nano-structured polymer scaffold," Zhongguo Xiu Fu Chong Jian Wai Ke Za Zhi, 21(4):411-415 (Apr. 2007), 1 sheet abstract.
Chen, R., et al., "Preparation and characterization of coaxial electrospun thermoplastic polyurethane/collagen compound nanofibers for tissue engineering applications," Colloids and Surfaces B: Biointerfaces 79(2):315-325 (Sep. 1, 2010) (available online Apr. 3, 2010).
Chen, W.-Q., H. Priewalder, et al. (2010). "Silk cocoon of Bombyx mori: Proteins and posttranslational modifications—heavy phosphorylation and evidence for lysine-mediated cross links." Proteomics 10(3): 369-379.
Chen, Y., et al., "Increased osteoblast functions in the presence of BMP-7 short peptides for nanostructured biomaterial applications," J. Biomed. Mater. Res. A 91:296-304 (2009; published online Nov. 3, 2008).
Chobanian, A. V., G. L. Bakris, et al. (2003). "Seventh Report of the Joint National Committee on Prevention, Detection, Evaluation, and Treatment of High Blood Pressure." Hypertension 42(6): 1206-1252.
Chronakis, I.S., "Novel nanocomposites and nanoceramics based on polymer nanofibers using electrospinning process—A review," Journal of Materials Processing Technology 167:283-293 (2005).
Cilurzo, F., C. G. M. Gennari, et al. (2011). "An investigation into silk fibroin conformation in composite materials intended for drug delivery." International Journal of Pharmaceutics 414(1-2): 218-224.
De Cock, L. J. (2010). "Layer-by-layer incorporation of growth factors in decellularized aortic heart valve leaflets." Biomacromolecules 11(4): 1002-1008.
De Cupere, V. M., J. Van Wetter, et al. (2003). "Nanoscale Organization of Collagen and Mixed Collagen Pluronic Adsorbed Layers." Langmuir 19(17): 6957-6967.
Deka, H., et al., "Biocompatible hyperbranched polyurethane/multi-walled carbon nanotube composites as shape memory materials," Carbon 48:2013-2022 (2010; available online Feb. 11, 2010).
Deng, C. (2011). "Application of decellularized scaffold combined with loaded nanoparticles for heart valve tissue engineering in vitro." Journal of Huazhong University of Science and Technology. Medical sciences 31(1): 88-93.
Deng, M., et al., "Biomimetic, bioactive etheric polyphosphazene-poly(lactide-co-glycolide) blends for bone tissue engineering," J. Biomed Mater Res A 92:114-125 (2010; published online Jan. 22, 2009).
Deng, M., et al., "Miscibility and in vitro osteocompatibility of biodegradable blends of poly[(ethyl alanato) (p-phenyl phenoxy) phosphazene] and poly(lacitic acid-glycolic acid)," Biomaterials 29:337-349 (2008; available online Oct. 17, 2007).
Dijkman, P. E., A. Driessen-Mol, et al. (2012). "Decellularized homologous tissue-engineered heart valves as off-the-shelf alternatives to xeno- and homografts." Biomaterials 18:4545-54.
Dohmen, P. M., A. Lembcke, et al. (2011). "Ten Years of Clinical Results With a Tissue-Engineered Pulmonary Valve." The Annals of Thoracic Surgery 92(4): 1308-1314.
Dong, B., et al., "Electrospinning of collagen nanofiber scaffolds from benign solvents," Macromolecular Rapid Communications 30(7):539-542 (Feb. 5, 2009).
Douglas, T., et al., "Novel ceramic bone replacement material CeraBall® seeded with human mesenchymal stem cells," Clin. Oral Impl. Res. 21:262-267 (2010).
Edwards, M. B., E. R. Draper, et al. (2005). "Mechanical testing of human cardiac tissue: some implications for MRI safety." J Cardiovasc Magn Reson 7(5): 835-840.

(56) References Cited

OTHER PUBLICATIONS

Ekaputra, A.K., et al., "Composite electrospun scaffolds for engineering tubular bone grafts," Tissue Eng. Part A 15(12):3779-3788 (Dec. 8, 2009) (published online Jul. 20, 2009; online ahead of print: Jul. 24, 2009; online ahead of editing: Jun. 15, 2009).

Faria, M.L.E., et al., "Recombinant human bone morphogenetic protein-2 in absorbable collagen sponge enhances bone healing of tibial osteotomies in dogs," Veterinary Surgery 36(2):122-131 (Feb. 2007; first published online Mar. 2, 2007).

Fujihara, K., et al., "Guided bone regeneration membrane made of polycaprolactone/calcium carbonate composite nano-fibers," Biomaterials 26:4139-4147 (2005; available online Dec. 24, 2004).

Gu, X. and K. S. Masters (2010). "Regulation of valvular interstitial cell calcification by adhesive peptide sequences." Journal of Biomedical Materials Research Part A 93A(4): 1620-1630.

Guan, J., et al., "Preparation and characterization of highly porous, biodegradable polyurethane scaffolds for soft tissue applications," Biomaterials 26:3961-3971 (2005; available online Dec. 8, 2004).

Hayashi, T. and S. Mukamel (2007). "Vibrational Exciton Couplings for the Amide I, II, III, and a Modes of Peptides." The Journal of Physical Chemistry B 111(37): 11032-11046.

Hersh, R.E., et al., "A technique for the treatment of sternal infections using the vacuum assisted closure device", Heart Surg. Forum, 4(3):211-15 (2001).

Heydarkhan-Hagvall, S., et al., "Three-dimensional electrospun ECM-based hybrid scaffolds for cardiovascular tissue engineering," Biomaterials 29(19):2907-2914 (Jul. 2008; available online Apr. 9, 2008).

Hill, C.A., et al., "Superior sternal cleft repair using autologous rib grafts in an infant with complex congenital heart disease," Ann. Thorac. Surg., 84:673-4, (2007).

Hinton, R. B. and K. E. Yutzey (2011). "Heart Valve Structure and Function in Development and Disease." Annual Review of Physiology 73(1): 29-46.

Hong, Y., et al., "Preparation, bioactivity, and drug release of hierarchical nanoporous bioactive glass ultrathin fibers," Adv. Mater. 22:754-758 (2010).

Hong, Y., et al., "Tailoring the degradation kinetics of poly(ester carbonate urethane)urea thermoplastic elastomers for tissue engineering scaffolds," Biomaterials 31:4249-4258 (2010; available online Feb. 25, 2010).

Hopkins, R. A. (2005). "Tissue engineering of heart valves: decellularized valve scaffolds." Circulation (New York, N.Y.) 111(21): 2712-2714.

Horan, R. L., K. Antle, et al. (2005). "In vitro degradation of silk fibroin." Biomaterials 26(17): 3385-3393.

Hoshi, R.A., "Nanoporous biodegradable elastomers," Adv. Mater. 21:188-192 (2009).

Hu, X., D. Kaplan, et al. (2006). "Determining Beta-Sheet Crystallinity in Fibrous Proteins by Thermal Analysis and Infrared Spectroscopy." Macromolecules 39 (18): 6161-6170.

Ifkovits, J.L., et al., "Biodegradable and radically polymerized elastomers with enhanced processing capabilities," Biomed Mater. 3(3):034104 (Sep. 2008) (published Aug. 8, 2008).

Ifkovits, J.L., et al., "Biodegradable fibrous scaffolds with tunable properties formed from photo-cross-linkable poly(glycerol sebacate)," ACS Appl. Mater. Interfaces 1(9):1878-1886 (Sep. 2009; published online Sep. 11, 2009).

Jeong, C.G., et al., "Mechanical, permeability, and degradation properties of 3D designed poly(1,8 octanediol-co-citrate) scaffolds for soft tissue engineering," J. Biomed. Mater. Res. Part B: Appl. Biomater. 93(1):141-149 (Apr. 2010; published online Jan. 20, 2010).

Ji, Y., et al., "Electrospun three-dimensional hyaluronic acid nanofibrous scaffolds," Biomaterials 27:3782-3792 (2006; available online Mar. 23, 2006).

Jiang, C., X. Wang, et al. (2007). "Mechanical Properties of Robust Ultrathin Silk Fibroin Films." Advanced Functional Materials 17(13): 2229-2237.

Jordan, J. E., J. K. Williams, et al. (2012). "Bioengineered self-seeding heart valves." The Journal of thoracic and cardiovascular surgery 143(1): 201-208.

Kidane, A. G., G. Burriesci, et al. (2009). "A novel nanocomposite polymer for development of synthetic heart valve leaflets." Acta Biomaterialia 5(7): 2409-2417.

Kidoaki, S., et al., "Mesoscopic spatial designs of nano- and microfiber meshes for tissue-engineering matrix and scaffold based on newly devised multilayering and mixing electrospinning techniques," Biomaterials 26(1):37-46 (Jan. 2005) (available online Mar. 2, 2004).

Kim, H.W., et al., "Bioactive glass nanofiber-collagen nanocomposite as a novel bone regeneration matrix," J. Biomed. Mater. Res. A 79:698-705 (2006; published online Jul. 18, 2006).

Kim, K., M. Yu, et al. (2003). "Control of degradation rate and hydrophilicity in electrospun non-woven poly(d,l-lactide) nanofiber scaffolds for biomedical applications." Biomaterials 24(27): 4977-4985.

Kim, S.S., et al., "Accelerated bonelike apatite growth on porous polymer/ceramic composite scaffolds in vitro," Tissue Eng. 12(10):2997-3006 (Oct. 2006).

Krogman, N.R., et al., "Hydrogen bonding in blends of polyesters with dipeptide-containing polyphosphazenes," J. Appl. Polym. Sci. 115:431-437 (2010; published online Sep. 1, 2009).

Krogman, N.R., et al., "The influence of side group modification in polyphosphazenes on hydrolysis and cell adhesion of blends with PLGA," Biomaterials 30:3035-3041 (2009; available online Apr. 5, 2009).

Lahiri, D., et al., "Boron nitride nanotube reinforced polylactide-polycaprolactone copolymer composite: Mechanical properties and cytocompatibility with osteoblasts and macrophages in vitro," Acta Biomaterialia 6:3524-3533 (2010; available online Mar. 10, 2010).

Lee, K.-W., D. B. Stolz, et al. (2011). "Substantial expression of mature elastin in arterial constructs." Proceedings of the National Academy of Sciences 108(7): 2705-2710.

Leonelli, C., et al., "Synthesis and characterization of cerium-doped glasses and in vitro evaluation of bioactivity," Journal of Non-Crystalline Solids 316:198-216 (2003).

Li, C., et al., "Electrospun silk-BMP-2 scaffolds for bone tissue engineering," Biomaterials, 27(16):3115-3124 (Jun. 2006) (available online Feb. 3, 2006).

Li, M., et al., "Electrospun blends of natural and synthetic polymers as scaffolds for tissue engineering," Conf. Proc. IEEE Eng. Med. Biol. Soc. 6:5858-5861 (2005), 1 sheet abstract.

Li, M., et al., "Electrospun protein fibers as matrices for tissue engineering," Biomaterials 26(30):5999-6008 (Oct. 2005) (available online May 13, 2005).

Li, W.J., et al., "Fabrication and characterization of six electrospun poly(alpha-hydroxy ester)-based fibrous scaffolds for tissue engineering applications," Acta Biomater. 2(4):377-385 (Jul. 2006; published online May 6, 2006).

Liu, T., W. K. Teng, et al. (2010). "Photochemical crosslinked electrospun collagen nanofibers: Synthesis, characterization and neural stem cell interactions." Journal of Biomedical Materials Research Part A 95A(1): 276-282.

Liu, Y., et al., "Electrospinning of poly(ethylene-co-vinyl acetate)/clay nanocomposite fibers," J. Polym. Sci.: Part B: Polym. Phys. 47:2501-2508 (Dec. 2009; first published online Nov. 10, 2009).

Lombardi, S. J. and D. L. Kaplan (1990). "The Amino Acid Composition of Major Ampullate Gland Silk (Dragline) of Nephila Clavipes (Araneae, Tetragnathidae)." Journal of Arachnology 18(3): 297-306.

Lu, X.L., et al., "Shape memory property of poly(L-lactide-co-µ-caprolactone) copolymers," Materials Science and Engineering A 438-440:857-861 (2006).

Ma, Z., et al., "Potential of nanofiber matrix as tissue-engineering scaffolds," Tissue Engineering 11(½):101-109 (2005).

Malafaya, P. B., G. A. Silva, et al. (2007). "Natural-origin polymers as carriers and scaffolds for biomolecules and cell delivery in tissue engineering applications." Advanced Drug Delivery Reviews 59(4-5): 207-233.

(56) References Cited

OTHER PUBLICATIONS

Martins, A., et al., "Biodegradable nanofibers-reinforced microfibrous composite scaffolds for bone tissue engineering," Tissue Engineering: Part A, 16(12):3599-3609 (2010) (published online Sep. 21, 2010).
Mendelboum Raviv, S., K. Szekeres-Csiki, et al. (2011). "Coating conditions matter to collagen matrix formation regarding von Willebrand factor and platelet binding." Thrombosis Research 129(4):e29-35.
Minoura, N., M. Tsukada, et al. (1990). "Fine structure and oxygen permeability of silk fibroin membrane treated with methanol." Polymer 31(2): 265-269.
Mirensky, T. L. and C. K. Breuer (2008). "The Development of Tissue-Engineered Grafts for Reconstructive Cardiothoracic Surgical Applications." Pediatr Res 63(5): 559-568.
Misra, S.K., et al., "Characterization of carbon nanotube (MWCNT) containing P(3HB)/bioactive glass composites for tissue engineering applications," Acta Biomaterialia 6:735-742 (2010; available online Oct. 1, 2009).
Mol, A. (2004). "Review article: Tissue engineering of semilunar heart valves: current status and future developments." The Journal of heart valve disease 13 (2): 272-280.
Nagata, M., et al., "Synthesis, characterization, and enzymatic degradation of network aliphatic copolyesters," Journal of Polymer Science: Part A: Polymer Chemistry, 37:2005-2011 (1999).
Nair, L.S., et al., "Biodegradable polymers as biomaterials," Prog. Polym. Sci. 32:762-798 (2007; available online Jun. 11, 2007).
Nair, L.S., et al., "Nanofibers and nanoparticles for orthopaedic surgery applications," J. Bone Joint Surg. Am. 90(Supp. 1):128-131 (2008).
Nair et al. (2004). "Development of novel tissue engineering scaffolds via electrospinning." Exper. Opin. Biol. Ther. 4:659-668.
Ndreu, A., et al., "Electrospun biodegradable nanofibrous mats for tissue engineering," Nanomedicine (Lond.) 3(1):45-60 (Feb. 2008), 1 sheet abstract.
Newton, D., R. Mahajan, et al. (2009). "Regulation of material properties in electrospun scaffolds: Role of cross-linking and fiber tertiary structure." Acta Biomaterialia 5(1): 518-529.
Nkomo, V. T., J. M. Gardin, et al. (2006). "Burden of valvular heart diseases: a population-based study." The Lancet 368(9540): 1005-1011.
Okhawilai, M. (2010). "Preparation of Thai silk fibroin/gelatin electrospun fiber mats for controlled release applications." International journal of biological macromolecules 46(5): 544-550.
Ostergaard L, Kristiansen SB, Angleys H, et al. The role of capillary transit time heterogeneity in myocardial oxygenation and ischemic heart disease. Basic Res Cardiol May 2014;109(3):409.
Pomerantseva, I., N. Krebs, et al. (2009). "Degradation behavior of poly(glycerol sebacate)." Journal of Biomedical Materials Research Part A 91A(4): 1038-1047.
Qiu, H., et al., "A citric acid-based hydroxyapatite composite for orthopedic implants," Biomaterials 27:5845-5854 (2006) (available online Aug. 21, 2006).
Ranganathan, S.I., et al., "Shaping the micromechanical behavior of multi-phase composites for bone tissue engineering," Acta Biomaterial 6:3448-3456 (2010; available online Mar. 24, 2010).
Ren, L., et al., "Fabrication of gelatin-siloxane fibrous mats via sol-gel and electrospinning procedure and its application for bone tissue engineering," Materials Science and Engineering C 30:437-444 (2010; available online Jan. 11, 2010).
Rockwood, D. N., R. C. Preda, et al. (2011). "Materials fabrication from Bombyx mori silk fibroin." Nat. Protocols 6(10): 1612-1631.
Ruzmetov, M., J. J. Shah, et al. (2012). "Decellularized versus standard cryopreserved valve allografts for right ventricular outflow tract reconstruction: A single-institution comparison." The Journal of thoracic and cardiovascular surgery 143(3): 543-549.
Sacks, M. S., F. J. Schoen, et al. (2009). "Bioengineering Challenges for Heart Valve Tissue Engineering." Annual Review of Biomedical Engineering 11(1): 289-313.
Sant, S., C. M. Hwang, et al. (2011). "Hybrid PGS-PCL microfibrous scaffolds with improved mechanical and biological properties." Journal of Tissue Engineering and Regenerative Medicine 5(4): 283-291.
Sant, S., et al., "Fabrication and characterization of tough elastomeric fibrous scaffold applications," Conf. Proc IEEE Eng. Med. Biol. Soc. 2010:3546-3548, and 32nd Annual International Conference of the IEEE EMBS Buenos Aires, Argentina, (Aug. 31-Sep. 4, 2010).
Sant, S. and A. Khademhosseini (2010). Fabrication and characterization of tough elastomeric fibrous scaffolds for tissue engineering applications. Engineering in Medicine and Biology Society (EMBC), 2010 Annual International Conference of the IEEE.
Sasaki, N., et al., "Stress-strain curve and Young's Modulus of a collagen molecule as determined by the x-ray diffraction technique," J. Biomechanics, 29(5):655-658 (1996).
Schofer, M.D., et al., "Characterization of a PLLA-collagen I blend nanofiber scaffold with respect to growth and osteogenic differentiation of human mesenchymal stem cells," ScientificWorldJournal 9:118-129 (Feb. 15, 2009).
Schopka, S. (2009). "Recellularization of biological heart valves with human vascular cells: in vitro hemocompatibility assessment." Journal of biomedical materials research. Part B, Applied biomaterials 88(1): 130-138.
Schroeder, W. A., L. M. Kay, et al. (1955). "The Amino Acid Composition of Bombyx mori Silk Fibroin and of Tussah Silk Fibroin." Journal of the American Chemical Society 77(14): 3908-3913.
Sell, S. A., M. J. McClure, et al. (2009). "Electrospinning of collagen/biopolymers for regenerative medicine and cardiovascular tissue engineering." Advanced Drug Delivery Reviews 61(12): 1007-1019.
Sell, S. A., P. S. Wolfe, et al. (2010). "The Use of Natural Polymers in Tissue Engineering: a Focus on Electrospun Extracellular Matrix Analogues." Polymers 2(4): 522-553.
Sethuraman, S., et al., "Novel low temperature setting nanocrystalline calcium phosphate cements for bone repair: Osteoblast cellular response and gene expression studies," J. Biomed. Mater. Res. A 82:884-891 (2007; published online Mar. 2, 2007).
Shah, P.N., et al., "Electrospinning of L-tyrosine polyurethanes for potential biomedical applications," Polymer 50:2281-2289 (May 2009; available online Mar. 19, 2009).
Shekaran, A. and A. J. Garcia (2011). "Nanoscale engineering of extracellular matrix-mimetic bioadhesive surfaces and implants for tissue engineering." Biochimica et Biophysica Acta (BBA)—General Subjects 1810(3): 350-360.
Simon, P., M. T. Kasimir, et al. (2003). "Early failure of the tissue engineered porcine heart valve SYNERGRAFT® in pediatric patients." European Journal of Cardio-Thoracic Surgery 23(6): 1002-1006.
Simone, E. A., T. D. Dziubla, et al. (2009). "Filamentous Polymer Nanocarriers of Tunable Stiffness that Encapsulate the Therapeutic Enzyme Catalase." Biomacromolecules 10(6): 1324-1330.
Sjogren, J., et al., "Vacuum-assisted closure therapy in mediastinitis after heart transplantation", J. Heart Lung Transplant., 23(4):506-7 (Apr. 2004).
Smith, I.O., et al., "Nanostructured polymer scaffolds for tissue engineering and regenerative medicine," Interdisciplinary Reviews: WIREs Nanomed. Nanobiotechnol. 1(2):226-236 (Mar./Apr. 2009) (Jan. 12, 2009).
Smith, L.A., et al., "Nano-fibrous scaffolds for tissue engineering," Colloids and Surfaces B: Biointerfaces 39(3):125-131 (Dec. 10, 2004; available online Feb. 4, 2004).
Soletti, L., et al., "A bilayered elastomeric scaffold for tissue engineering of small diameter vascular grafts," Acta Biomaterialia 6:110-122 (2010; available online Jun. 18, 2009).
Soliman, S., S. Sant, et al. (2011). "Controlling the porosity of fibrous scaffolds by modulating the fiber diameter and packing density." Journal of Biomedical Materials Research Part a 96A(3): 566-574.
Sung, H.-W., C.-N. Chen, et al. (2000). "In vitro surface characterization of a biological patch fixed with a naturally occurring crosslinking agent." Biomaterials 21(13): 1353-1362.

(56) References Cited

OTHER PUBLICATIONS

Tedder, M. E. (2009). "Stabilized collagen scaffolds for heart valve tissue engineering." Tissue engineering. Part A 15(6): 1257-1268.

Trowbridge, E. A., P. V. Lawford, et al. (1989). "Pericardial heterografts: a comparative study of suture pull-out and tissue strength." Journal of Biomedical Engineering 11(4): 311-314.

Um, I. C., H. Kweon, et al. (2001). "Structural characteristics and properties of the regenerated silk fibroin prepared from formic acid." International journal of biological macromolecules 29(2): 91-97.

Um, I.C., et al., "Electro-spinning and electro-blowing of hyaluronic acid," Biomacromolecules 5:1428-1436 (2004; published online May 7, 2004).

Van Susante, J.L.C., et al., "Linkage of chondroitin-sulfate to type I collagen scaffolds stimulates the bioactivity of seeded chondrocytes in vitro," Biomaterials, 22:2359-2369 (2001).

Venugopal, J., et al., "Biomimetic hydroxyapatite-containing composite nanofibrous substrates for bone tissue engineering," Phil. Trans. R. Soc. A 368:2065-2081 (2010).

Venugopal, J. R. et al., "Nanobioengineered electrospun composite nanofibers and osteoblasts for bone regeneration," Artif. Organs 32(5):388-397 (2008).

Vesely, I. and R. Noseworthy (1992). "Micromechanics of the fibrosa and the ventricularis in aortic valve leaflets." Journal of Biomechanics 25(1): 101-113.

Wan, L.-S. and Z.-K. Xu (2009). "Polymer surfaces structured with random or aligned electrospun nanofibers to promote the adhesion of blood platelets." Journal of Biomedical Materials Research Part A 89A(1): 168-175.

Wan, Y., et al., "Biphasic scaffold for annulus fibrosus tissue regeneration," Biomaterials 29:643-652 (2008; available online Nov. 13, 2007).

Wang, C., et al., "Correlation between processing parameters and microstructure of electrospun poly(D,L-lactic acid) nanofibers," Polymer 50:6100-6110 (Nov. 2009; available online Oct. 30, 2009).

Wang, J., et al., "Spiral-structured, nanofibrous, 3D scaffolds for bone tissue engineering," J. Biomed. Mater. Res. A 93:753-762 (2010; published online Jul. 29, 2009).

Wang, W., et al., "Biodegradable polyurethane based on random copolymer of L-lactide and µ-caprolactone and its shape-memory property," J. Appl. Polym. Sci. 104:4182-4187 (2007).

Wang, Y., et al., "In vivo degradation characteristics of poly(glycerol sebacate)," J. Biomed Mater Res A, 66(1):192-197 (Jul. 1 2003) (published online Jun. 10, 2003).

Wang, Y., G. A. Ameer, et al. (2002). "A tough biodegradable elastomer." Nat Biotech 20(6): 602-606.

Webb, A.R., et al., "Biodegradable polyester elastomers in tissue engineering," Expert Opin. Biol. Ther. 4(6):801-812 (2004).

Yacoub, M. H. and J. J. M. Takkenberg (2005). "Will heart valve tissue engineering change the world?" Nat Clin Pract Cardiovasc Med 2(2): 60-61.

Yacoub, M. H. and L. H. Cohn (2004). "Novel Approaches to Cardiac Valve Repair." Circulation 109(9): 1064-1072.

Yamada, K. M., D. W. Kennedy, et al. (1980). "Characterization of fibronectin interactions with glycosaminoglycans and identification of active proteolytic fragments." Journal of Biological Chemistry 255(13): 6055-6063.

Yang, J., et al., "Synthesis and evaluation of poly(diol citrate) biodegradable elastomers," Biomaterials 27:1889-1898 (2006; available online Nov. 15, 2005).

Yang, X., et al., "Acceleration of osteogenic differentiation of preosteoblastic cells by chitosan containing nanofibrous scaffolds," Biomacromolecules 10 (10):2772-2778 (Sep. 10, 2009).

Yang, X., et al., "Multifunctional nanofibrous scaffold for tissue engineering," Journal of Experimental Nanoscience 3(4):329-345 (2008).

Yi, F., et al., "Poly(glycerol sebacate) nanofiber scaffolds by core/shell electrospinning," Macromol. Biosci. 8:803-806 (2008).

Yi, F. and D. A. LaVan (2008). "Poly(glycerol sebacate) Nanofiber Scaffolds by Core/Shell Electrospinning." Macromolecular Bioscience 8(9): 803-806.

Yoganathan, A. P., Z. He, et al. (2004). "Fluid Mechanics of Heart Valves." Annual Review of Biomedical Engineering 6(1): 331-362.

Yoshimoto, H., et al., "A biodegradable nanofiber scaffold by electrospinning and its potential for bone tissue engineering," Biomaterials 24(12):2077-2082 (May 2003).

Zhang, Y., et al., "Electrospun biomimetic nanocomposite nanofibers of hydroxyapatite/chitosan for bone tissue engineering," Biomaterials 29:4314-4322 (2008; available online Aug. 20, 2008).

Zhong, S.P., et al., "Development of a novel collagen-GAG nanofibrous scaffold via electrospinning," Materials Science and Engineering: C, 27(2):262-266 (Mar. 2007) (available online Jun. 8, 2006).

Zhou, C.-Z., et al. (2001) "Silk Fibroin: Structural implications of a remarkable amino acid sequence." Proteins: Structure, Function, and Bioinformatics 44(2): p. 119-122.

Zhou, J., C. Cao, et al. (2010). "In vitro and in vivo degradation behavior of aqueous-derived electrospun silk fibroin scaffolds." Polymer Degradation and Stability 95(9): 1679-1685.

Zhu, J., A. Negri, et al. (2010). "Closed headpiece of integrin alphaIIbbeta3 and its complex with an alphaIIbbeta3-specific antagonist that does not induce opening." Blood(Aug. 2, 2010): Dec. 2010.

Zoccola, M., A. Aluigi, et al. (2008). "Study on Cast Membranes and Electrospun Nanofibers Made from Keratin/Fibroin Blends." Biomacromolecules 9(10): 2819-2825.

Zong, X., S. Ran, et al. (2003). "Structure and Morphology Changes during in Vitro Degradation of Electrospun Poly(glycolide-co-lactide) Nanofiber Membrane." Biomacromolecules 4(2): 416-423.

Zou, L., S. Cao, et al. (2012). "Fibronectin induces endothelial cell migration through beta1-integrin and Src dependent phosphorylation of fibroblast growth factor receptor-1 at tyrosines 653/654 and 766." Journal of Biological Chemistry.

\* cited by examiner

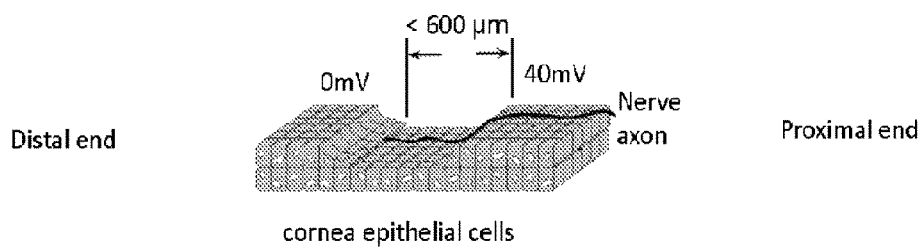
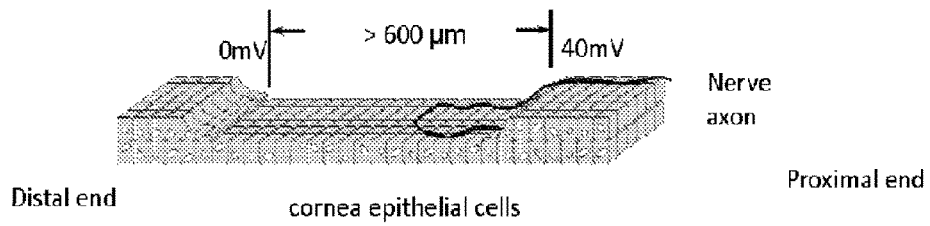
FIGURE 1

Exemplary Table of Mechanical Properties and Cell Responses of Biodegradable Polymers

| Polymer | Abbreviation | Young's modulus [MPa] | Tensile Strength [MPa] | Degradation | Cell Viability |
|---|---|---|---|---|---|
| poly (pyrrole) | Ppy | 20-500 | 3-50 | | Mild - up to 2 weeks. Moderate to severe tissue reaction from 1-4 months. |
| poly (caprolactone) | PCL | 250 | 12 | 92% remaining at 42 days, total degradation 1-3 years | No cytotoxic response |
| poly (aniline) | PANI | 200-2000 | 2-3 | | 60% survival at 9 weeks |
| collagen | | .001-.04 | .0005-.011 | | No cytotoxic response |
| poly(glycolic acid) | PGA | .005-6900 | 68.9 | 6-12 months | Minimal cytotoxic response |
| poly (lactic acid) | PLA | 2800 | 35 | 0.1% remaining @ 19 days | |
| poly (L-lactic acid) | PLLA | 17-23 | 27 - 36 | 70% remaining at 30 days | |
| poly (ester-urethane) urea | PEUU 2000 P | 11.9 | 24 - 34 | 95% remaining at 28 days, 65% remaining at 56 days | 100% survival at 2 d, 120% at 4 d |
| poly (caprolactone) fumarate | PCLF 530 | 0.67 | 0.48 | 85% remaining at 35 days | No cytotoxic response |
| | PCLF 1250 | 20 - 41 | 3.7 | 70% remaining at 35 days | No cytotoxic response |
| poly (3,4-ethylenedioxythiophene) | PEDOT | 1600-2000 | 33-52 | | 80% survival at 3 d |
| poly (glycerol sebacate) | PGS | 0.32 - 0.78 | 0.55 - 0.67 | 30-60 days | No cytotoxic response |
| poly (octane diol) citrate | POC | 0.40 - 0.76 | 0.44 - 0.80 | 30-60 days | Negative cellular response to unbound citrate |
| chitosan | | 9 - 12 | 0.08 - 0.64 | | No cytotoxic response |

Exemplary Table of Conductivity of Electrically Responsive Polymers

| Polymer | Abbreviation | Material Type | Conductivity [S/cm] |
|---|---|---|---|
| poly (pyrrole) | Ppy | synthetic | 40-200 |
| poly (aniline) | PANI | synthetic | 5 |
| poly (3,4-ethylenedioxythiophene) | PEDOT | synthetic | 0.19 |
| chitosan | | natural | 1e-5 - 1e-4 |
| poly (acetylene) | PA | synthetic | 200-1000 |

Exemplary Table of Measured Conductivity of Gold Nanowires

| Form | Conductivity [S/cm] |
|---|---|
| single nanowire | 2.1 x 10^-5 |
| bulk gold | 4.5 x 10^5 |
| indium tin oxide (ITO) film | 1x10^-4 |
| gold nanowires in film (100 mg/mL gold in ITO film) | 4.0 x 10^4 |

FIGURE 2

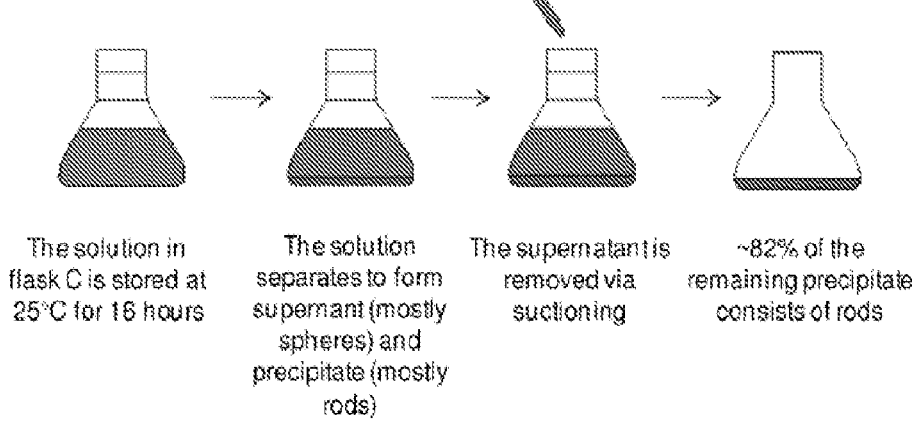
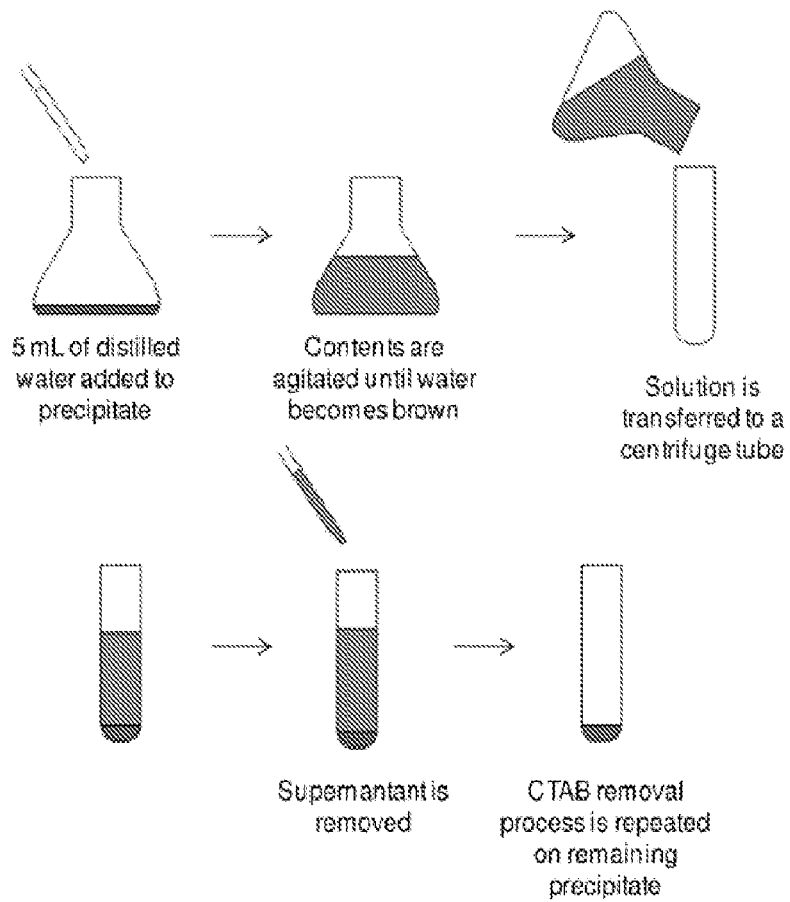
FIGURE 26C

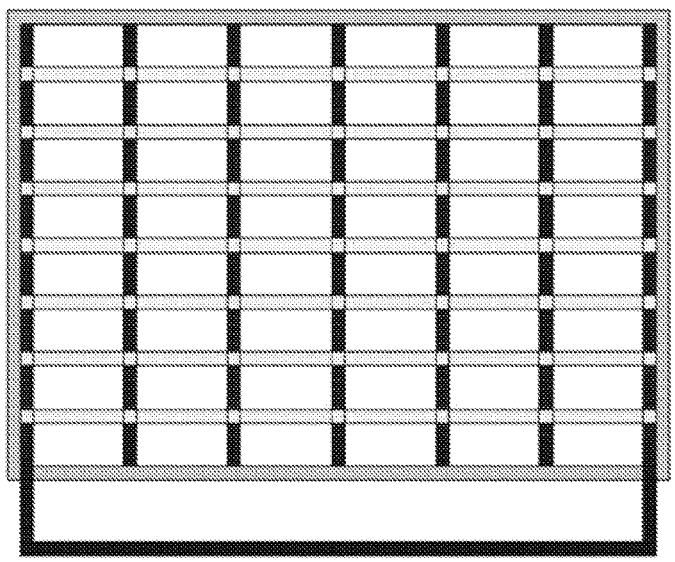

General Notes: This drawing is not to scale to enhance visualization of the structure. Actual structure is 20 cm x 12 cm with narrow struts 20 – 40 μm wide and spacing between struts of 600 μm.

Top View
Note: Green indicates rectangular mold, Yellow indicates struts which insert into the mold, Blue indicates support struts and handle for insert

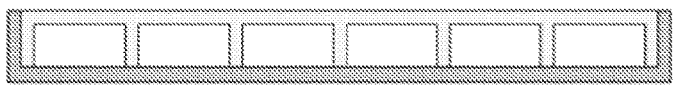

Side View
Note: Green indicates rectangular mold, Yellow indicates insert struts

FIGURE 27

| Group | Sample Type | Purpose | Sample Number |
|---|---|---|---|
| 1 | seeded conduit with neurons (inside) | control for neurons on conduit | 3 samples at 3 and 5 days |
| 2 | seeded conduit with Schwann cells (outside) | control for Schwann cells on conduit | 3 samples at 3 and 5 days |
| 3 | seeded conduit with neurons (inside), Schwann cells (outside) | experiment | 3 samples at 3 and 5 days |
| 4 | neurons seeded on collagen gel | positive control for neurons | 3 samples at 3 and 5 days |
| 5 | Schwann cells seed on collagen gel | positive control for Schwann cells | 3 samples at 3 and 5 days |
| 6 | conduit with no cells | negative control for material | 3 samples at 3 and 5 days |
| Expected Outcome: No difference in cell death or activity between seeded materials and positive controls. | | | Total = 6 x 6 = 36 |

FIGURE 29

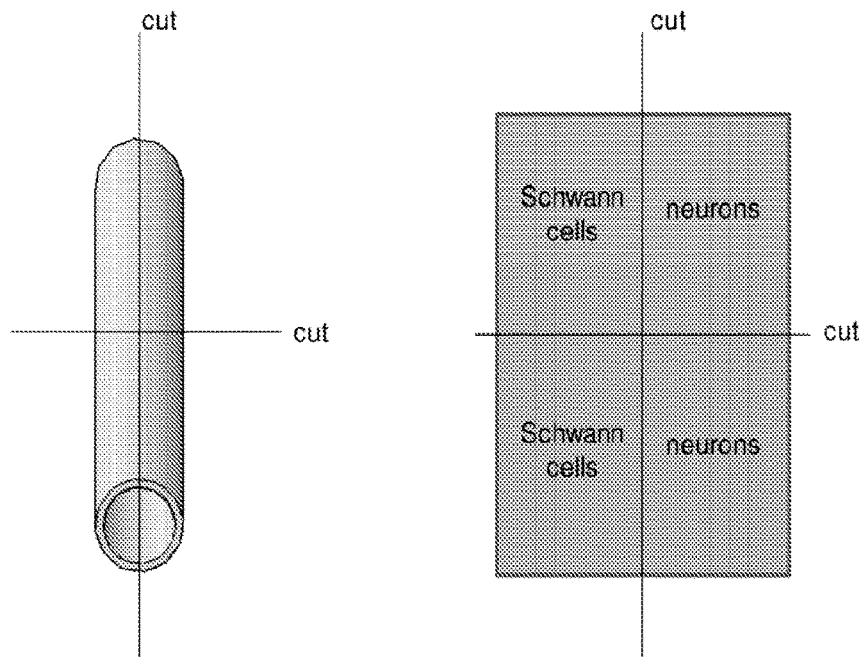

FIGURE 30

| Group | Sample Type | Purpose | Sample Number |
|---|---|---|---|
| 1 | seeded conduits, AC stimulation (3V, 20 Hz) | From literature | 3 samples at 24 and 48 hrs |
| 2 | seeded conduits, DC stimulation (0.8 V, constant) | Adjusted from literature | 3 samples at 24 and 48 hrs |
| 3 | seeded conduits, No stimulation | Negative control | 3 samples at 24 and 48 hrs |
| 4 | seeded conduits, AC stimulation (0.8V, 20 Hz) | Negative control | 3 samples at 24 and 48 hrs |
| 5 | seeded conduits, DC stimulation (3 V, constant) | Negative control | 3 samples at 24 and 48 hrs |
| Expected Outcome: AC stimulation will induce higher neurite outgrowth than DC or no stimulation. | | | Total = 6 x 5 = 30 |

FIGURE 31

| Group | Sample Stimulation Parameters | Purpose | Sample Number |
|---|---|---|---|
| 1 | No stimulation | negative control | 3 samples at 3 and 5 days |
| 2 | 1 hour/day everyday (1 hour on, 23 hours off) | shortest daily stim. | 3 samples at 3 and 5 days |
| 3 | Constant stimulation (24 hours per day) | positive control (longest daily stim.) | 3 samples at 3 and 5 days |
| 4 | 1 hour on the first day only | one time stimulation, lit. comparison | 3 samples at 3 and 5 days |
| 5 | Every other hour (1 hour on, 1 hour off) | short intervals between stim. | 3 samples at 3 and 5 days |
| 6 | Stimulation for one hour, repeated every 6 hours | longer intervals between stim. | 3 samples at 3 and 5 days |
| Expected Outcome: Once every six will likely produce maximum neurite outgrowth because it allows tissue to rest longer between stimulation while continuing periodic stimulation. | | | Total = 6 x 6 = 36 |

FIGURE 32

| Group | Sample | Purpose | Sample Number |
|---|---|---|---|
| 1 | Straight conduit of High Conductivity Material | negative control | 3 samples at 3 and 5 days |
| 2 | Straight conduit of Low Conductivity Material | positive control | 3 samples at 3 and 5 days |
| 3 | Low conductive material in 600 μm segments | based on electric field effect in animal models | 3 samples at 3 and 5 days |
| 4 | Low conductive material in 300 μm segments | halved spacing from animal models | 3 samples at 3 and 5 days |
| 5 | Low conductive material in 1200 μm segments | double spacing from animal models | 3 samples at 3 and 5 days |
| Expected Outcome: Low conductive material in 600 μm segments will induce maximal neurite outgrowth. | | | Total = 6 x 5 = 30 |

FIGURE 33

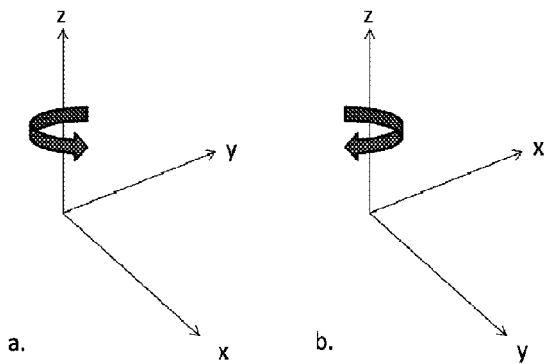

FIGURE 34

| Group | Sample | Purpose |
|---|---|---|
| 1 | autograft | positive control |
| 2 | untreated | negative control |
| 3 | Optimized Material from Aim 1, No Stimulation | negative control for material |
| 4 | Optimized Material and Stimulation from Aims 1 and 2 | experiment |

Expected Outcome: Optimized Material and Stimulation will enhance neurite outgrowth and demonstrate functional recovery prior to autograft.

FIGURE 35

| Total Number of Rats = Groups*Animals/Group*Evaluation Points ||||
|---|---|---|---|
| Groups | Animals/Group | Terminal Evaluation Points | Total Number of Rats |
| 4 | 12 | 2 | 96 |

FIGURE 36

CONDUIT FOR PERIPHERAL NERVE REPLACEMENT

RELATED APPLICATIONS

This application is a 371 application of International Application No. PCT/US2013/032520, filed Mar. 15, 2013, which claims the benefit of U.S. Provisional Application No. 61/623,528, filed Apr. 12, 2012, the entirety of which are incorporated by reference herein.

FIELD OF THE INVENTION

The present invention relates generally to biphasic materials and devices comprising the same and more particularly but not exclusively to biphasic polymeric materials including conductive polymers and conduits composed of the same for the treatment of peripheral nerves.

BACKGROUND OF THE INVENTION

Peripheral nerve impairment is caused by diseases, therapies, and injuries resulting in over 50,000 surgical procedures in the U.S. each year. Peripheral nerve repair is presently possible for transected nerve gaps of up to 3 cm. However, no treatment options are available for over 87% of patients having transacted nerve gaps greater than 3 cm because rapid scar formation overcomes slow nerve outgrowth. Indeed, current surgical options limit repair of peripheral nerves to a maximum gap of 3 cm. Attempts to surpass this 3 cm boundary have been ineffective.

Current surgical procedures for peripheral nerve damage are inadequate. Autografts and allografts are currently used but the availability and section of grafts and immunosuppression to prevent graft rejection are problems associated with graft procedures. Additionally, various types of conduits have been used for peripheral nerve replacement, but typically lack chemical, biological, and morphological guidelines provided by grafts. Among the drawbacks associated with presently deployed grafts and conduits is the fact that the repair, as stated, is limited to gaps of up to 3 cm in length. The length limitation is likely due to a lack of chemical and/or electrical stimuli. Indeed, various data indicate that an electrical stimulation field promotes upregulation of chemical, molecular and genetic factors to accelerate nerve repair over a 24-48 hour period. Experimental results from newt and bovine cornea transections indicate electric field gradients across a nerve transection may increase the promotion and direction of neurite outgrowth observed by single electric field gradients.

Due to the present limitations in the art for treating and repairing peripheral nerve damage, new therapies, materials and devices are needed. More specifically, new materials and methods are desperately needed to treat patients suffering from peripheral nerve impairment or injury and having a 3 cm or greater nerve gap.

SUMMARY OF THE INVENTION

The present invention involves development of materials and devices for repair of transected peripheral nerves. These devices or conduits are designed such that repeated electric field gradients can be initiated to promote neurite and axonal outgrowth. Conducting conduits using doped synthetic and/or natural polymers create specifically patterned high and low conducting segmented materials, which are mechanically used to produce the electrical properties needed for nerve conduits. These electrical properties stimulate neurite outgrowth and axonal repair following a peripheral nerve transection.

The present invention encompasses, in one aspect, a biphasic material comprising a first polymer component doped with a non-metal component, which increases the conductivity of the first polymer component; and a second polymer component. The first and/or second polymer component may include a bioabsorbable polymer. In some embodiments the first and/or second polymer component may comprise poly glycerol sebacate (PGS), an esterified polyglycerol sebacate, glycolic acid, polydiolcitrate, poly(ester-urethane)urea, polycaprolactone (PCL), hydroxyapatite, hyaluronic acid, alginate, collagen, elastin, vimentin, laminin, fibrin, melanin, gum Arabic, polycaprolactonefumarate, poly(octane diol) citrate, lactic acid, or combinations thereof. In another embodiment, the esterified polyglycerol sebacate is an acrylated polyglycerol sebacate (PGSA).

In a further embodiment, the non-metal component comprises polypyrrole, polyaniline, poly(3,4-ethylenedioxythiophene), polyacetylene carbon nanotubes, a silicate, or combinations thereof. The non-metal component may be capable of conductivity in the range of about 5-200 S/cm.

In a still further embodiment, the first polymer component and second polymer component are configured to support differing electric field gradients, respectively, therein. In certain embodiments, the first polymer component may have a conductivity of at least about $10^{-6}$-$10^{-4}$ S/cm. The second polymer component may have a conductivity of at least about 0-1.25×$10^{-5}$ S/cm. The first and/or second polymer component may, in certain embodiments of the claimed invention, have the mechanical properties of native nerve.

In an additional embodiment, the mechanical properties of the first and/or second polymer may be selected from the group consisting of an elastic modulus of at least about 0.4-0.7 mPa, a tensile strength of at least about 0.21-1.49 N, and a biodegradability of at least about 3-12 months. The biphasic material may also comprise cells.

In another aspect, the present invention comprises a tube configured to support a plurality of electric field gradients along its length, comprising a plurality of first segments and a plurality of second tubular segments adjoined along a common axis of the tube, the first tubular segments comprising a first polymer component doped with a non-metal component which increases the conductivity of the first polymer component, and the second tubular segments comprising a second polymer component.

In a first embodiment, the tube is bioresorbable. In another embodiment the first and/or second polymer component comprises a bioresorbable polymer. In a further embodiment, the first and/or second polymer component comprises poly glycerol sebacate, an esterified polyglycerol sebacate, glycolic acid, polydiolcitrate, poly(ester-urethane)urea, polycaprolactone, hydroxyapatite, alginate, collagen, elastin, vimentin, laminin, hyaluronic acid, fibrin, melanin, gum Arabic, polycaprolactonefumarate, poly(octane diol) citrate, lactic acid, or combinations thereof. In still further embodiments, the non-metal component comprises polypyrrole, polyaniline, poly(3,4-ethylenedioxythiophene), polyacetylene carbon nanotubes, a silicate, or combinations thereof.

In an additional embodiment, the length of the first tubular segments and the length of the second tubular segments are equal. However, in other embodiments, the length of the first tubular segments and the length of the second tubular segments are not equal. In one embodiment, the length of the first tubular segments is at least about 10-1200 μm. The length of the first tubular segments may be at least about 600 μm. In additional embodiments, the length of the second tubular segments is less than the first tubular segments. The length of the second tubular segments may be at least about 10-600 μm. In still further embodiments, the cylinder wall thickness of the plurality of first and/or second tubular segments is at least about 0.1 mm to 1 cm. The tube may also comprise cells.

In another aspect, the present invention comprises a telescoping segmented apparatus comprising a plurality of tubular segments disposed along a longitudinal axis, wherein each segment of the plurality of tubular segments comprises the biphasic material set forth hereinabove, and wherein each successive tubular segment has a smaller radius than a preceding tubular segment. In one embodiment, each tubular segment of the plurality of tubular segments has a cylinder wall thickness of at least about 0.1 mm to 1 cm. The telescoping segmented apparatus may also comprise cells.

In additional aspects, the present invention encompasses a sheet or a strip comprising the biphasic material set forth hereinabove. The sheet or strip may also comprise cells.

In a still further aspect, the present invention includes a method of making a tube configured to support a plurality of electric field gradients along its length, comprising the steps of:
(a) providing a mold having one or more depressions disposed therein;
(b) placing a low conductivity polymer in the depression;
(c) placing a high conductivity polymer over the low conductivity polymer;
(d) adhering the low and high conductivity polymers to one another; and
(e) removing the adhered low and high conductivity polymer from the mold to provide the tube configured to support a plurality of electric field gradients along its length.
In a first embodiment, at least one of the low conductivity polymer and high conductivity polymer comprise a bioabsorbable material. In a further embodiment, the method comprises the step of adhering the polymers comprises crosslinking the low and high conductivity polymers. In a still further embodiment, the step of providing a mold comprises providing a cylindrical mold in which the depressions are disposed on a surface of the mold. In another embodiment, the method further comprises the step of forming pores within the low and high conductivity polymers. The depressions may also comprise grooves. Additionally, the method may also include the step of seeding the tube with cells.

In another aspect, the present invention includes an esterified polyglycerol sebacate polymer, the repeating structural unit of the esterified polyglycerol sebacate polymer having the formula

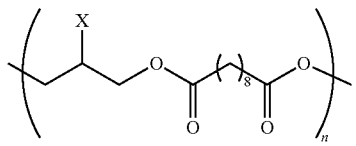

wherein X is an ester. In a first embodiment of the esterified polyglycerol sebacate polymer, the repeating structural unit of the esterified polyglycerol sebacate polymer has the formula

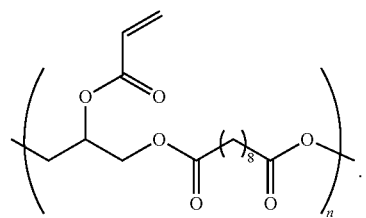

In an additional aspect, the present invention encompasses a method of repairing a damaged nerve comprising the steps of (a) placing a tube comprising the biphasic material set forth hereinabove at a nerve to be repaired, wherein the tube is configured to support a plurality of electric field gradients along its length; and (b) securing a distal stump of the damaged nerve to a distal end of the but such that proximal and distal stump of the damaged nerve are in electrical communication. Additionally, the method of repairing a damaged nerve may include the step of seeding the tube with cells.

BRIEF DESCRIPTION OF THE DRAWINGS

The foregoing summary and the following detailed description of the exemplary embodiments of the present invention may be further understood when read in conjunction with the appended drawings, in which:

FIG. 1 graphically illustrates the effect of electric fields on transacted nerve gaps in cornea epithelial cells.

FIG. 2 demonstrates three tables including: (1) an exemplary table of mechanical properties and cell responses of biodegradable polymers; (2) an exemplary table of conductivity of electrically responsive polymers; and (3) an exemplary table of measured conductivity of gold nanowires.

FIG. 10 demonstrates $^1$H NMR of prepolymers: (A) PGS. Sebacic acid peaks were observed at 1.2, 1.5, and 2.2 ppm; glycerol peaks were at 3.7, 4.2 and 5.2 ppm. (B) PGSA 25% acrylation. (C) PGSA 30% acrylation. (D) PGSA 35% acrylation. (E) PGSA 40% acrylation. For FIGS. 10B, 10C, 10D, and 10E, vinyl peaks were observed at 5.9, 6.1, and 6.4 ppm, in addition to sebacic acid and glycerol peaks as observed in PGS prepolymer.

FIG. 11 demonstrates (A) ATR-FTIR spectra, which are overlayed, of untreated PGS and PGSA with 25, 30, 35, and 40% acrylation. PGS 0% acrylation; the C═O bond was observed at 1700 cm$^{-1}$ and the stretch observed from 2850 to 2920 cm$^{-1}$ was attributed to C—H; finally, the O—H stretch was observed around 3300 cm$^{-1}$. PGSA 25% acrylation. PGSA 30% acrylation. PGSA 35% acrylation. PGSA 40% acrylation. For plots of 0, 25, 30, 35, and 40% the spectra were the same as PGS with the addition of any acrylate stretch at 1693 cm$^{-1}$. (B) ATR-FTIR spectra, which are overlayed, focusing on the range of about 2150 to 1650 cm$^{-1}$ to visualize the acrylate stretch.

Figure 12:
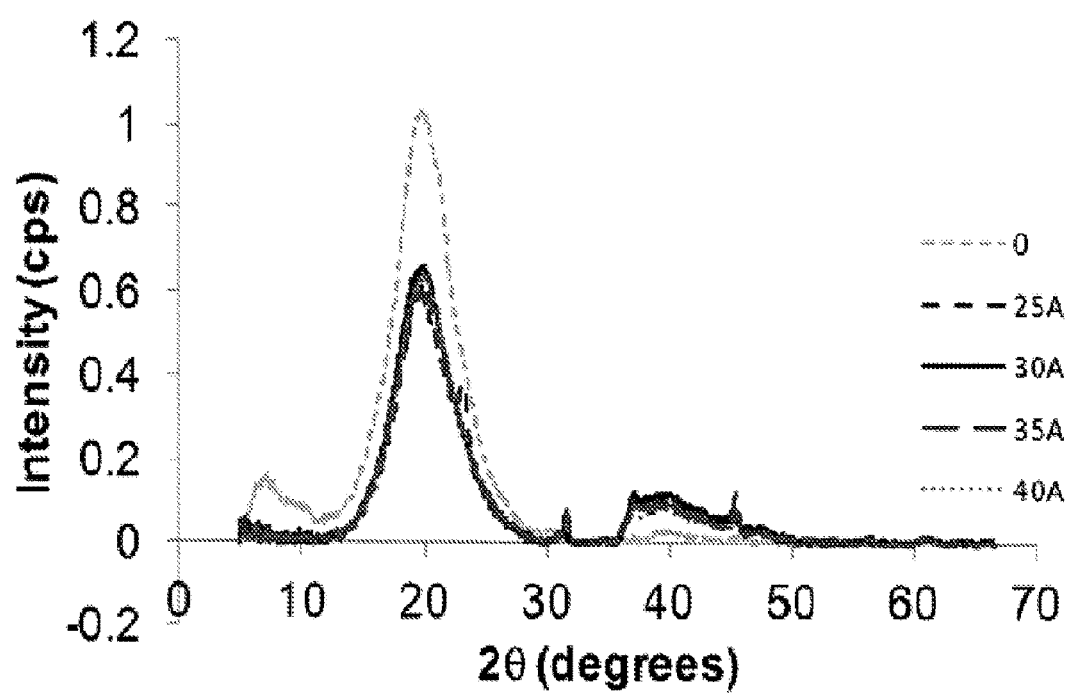

FIG. 12 demonstrates a Fourier transformed X-ray diffraction spectra for PGS and PGSA with 25, 30, 35, and 40% acrylation treated to remove unreacted agents. Specimens were free standing films of 0.6 mm thickness. Structure variations were observed at 7.6, 19.5, 32, 37, 39, and 45.5° along N.

Figure 13:
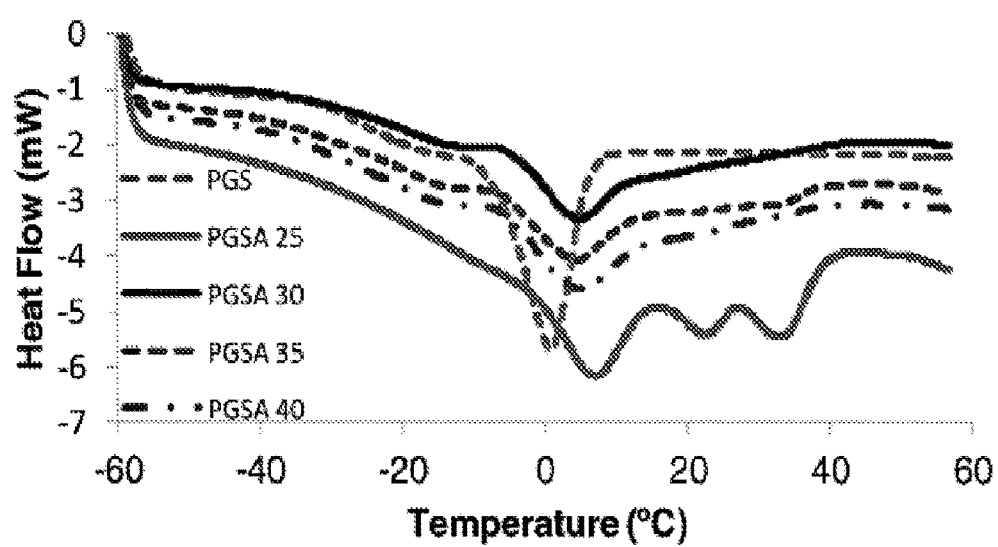

FIG. 13 demonstrates the DSC glass transition and melting curves for PGS and PGSA with 25, 30, 35, and 40% acrylation. (Heating from −60 to 60° C. at a rate of 10° C./min) PGS, Tg=−25.7±0.32° C. (mean±SEM); PGSA with 25% acrylation, Tg=−20.1±0.15° C. (mean±SEM); PGSA with 30% acrylation, Tg=−23.2±0.43° C. (mean±SEM); PGSA with 35% acrylation, Tg=−25.4±0.30° C. (mean±SEM); PGSA with 40% acrylation, Tg=−26.24±0.43° C. (mean±SEM). No significant difference was observed between 0, 35, and 40% acrylations. Significant differences were observed between 25%, 30%, and 0, 35, and 40% acrylations (p<0.0001).

Figure 14:
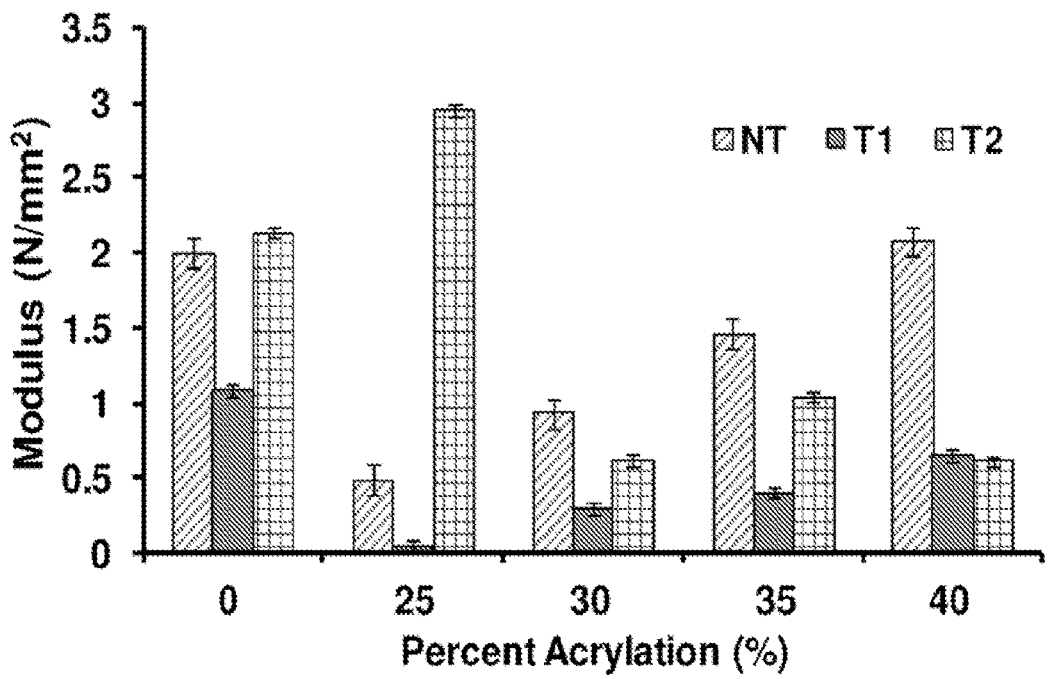

FIG. 14 graphically demonstrates an elastic moduli comparison of untreated PGS and PGSA with 25, 30, 35, and 40% acrylation. (Specimens were dog bone shaped with length=3.5 cm and width=5.0 cm. Testing was performed with a 500 N load cells with a crosshead speed rate of 50 mm/min.) The legend keys represent NT: untreated, T1: treatment 1 (repeated 70% ethanol washes), T2: treatment 2 (gradated ethanol washes) Bars represent mean elastic modulus from 3 repetitions with n=6. Lines represent standard error of the mean. ANOVA analysis showed statistically significant differences (p<0.0001). Waller Duncan's post hoc analysis was applied to separate means with statistically significant differences (p<0.05). Means with the same letter are not significantly different.

Figure 15:
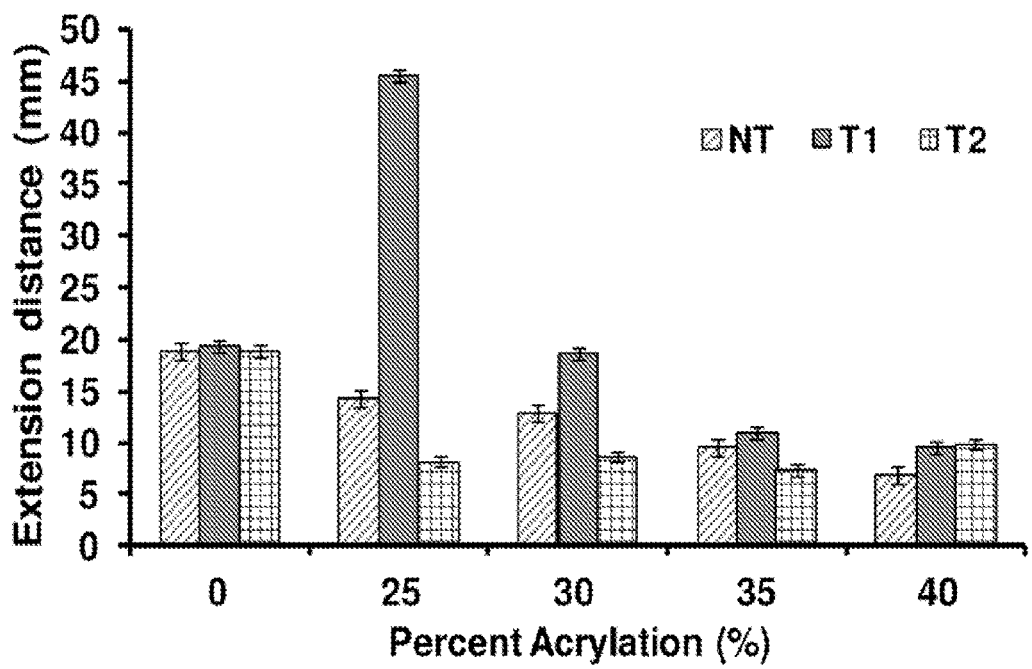

FIG. 15 graphically demonstrates an elongation to break comparison of untreated PGS and PGSA with 25, 30, 35, and 40% acrylation. (Specimens were dog bone shaped with length=3.5 cm and width=5.0 cm. Testing was performed with a 500 N load cells with a crosshead speed rate of 50 mm/min.) The legend keys represent NT: untreated, T1: treatment 1 (repeated 70% ethanol washes), T2: treatment 2 (gradated ethanol washes) Bars represent mean elongation to break from 3 repetitions with n=6. Lines represent standard error of the mean. ANOVA analysis showed statistically significant differences (p<0.0001). Waller Duncan's post hoc analysis was applied to separate means with statistically significant differences (p<0.05). Means with the same letter are not significantly different.

Figure 16:
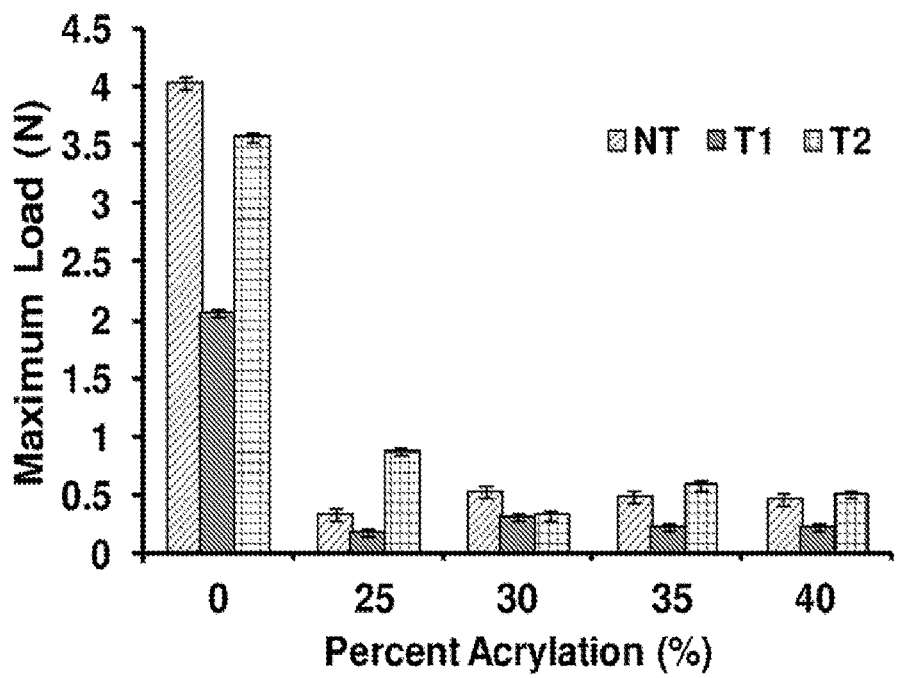

FIG. 16 graphically demonstrates a tensile strength comparison of untreated PGS and PGSA with 25, 30, 35, and 40% acrylation. (Specimens were dog bone shaped with length=3.5 cm and width=5.0 cm. Testing was performed with a 500 N load cells with a crosshead speed rate of 50 mm/min.) The legend keys represent NT: untreated, T1: treatment 1 (repeated 70% ethanol washes), T2: treatment 2 (gradated ethanol washes) Bars represent mean maximum load from 3 repetitions with n=6. Lines represent standard error of the mean. ANOVA analysis showed statistically significant differences (p<0.0001). Waller Duncan's post hoc analysis was applied to separate means with statistically significant differences (p<0.05). Means with the same letter are not significantly different.

Figure 17:
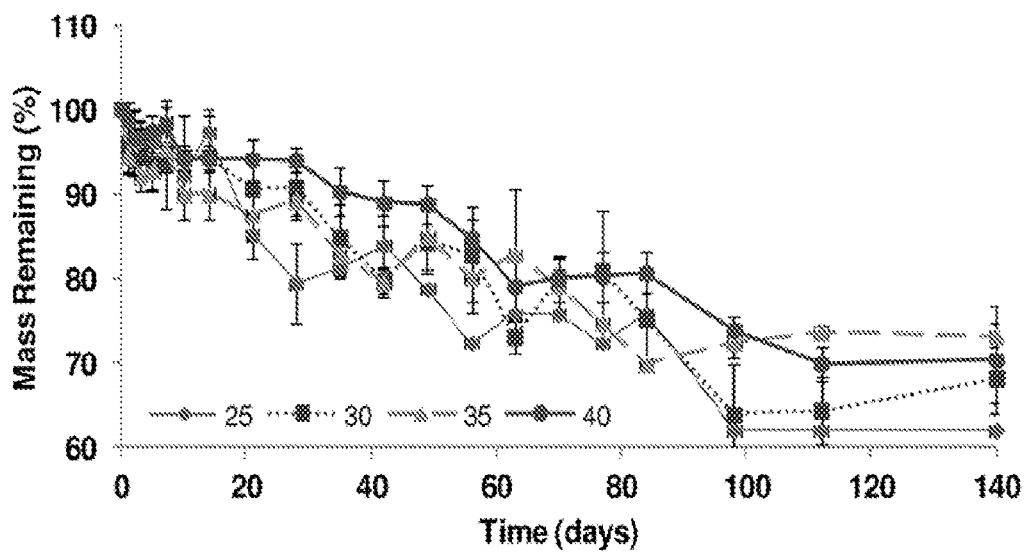

FIG. 17 graphically demonstrates an analysis of Degradation based on Mass Remaining that indicates that 70% of the mass of the tested material remains after 20 weeks and that there is no substantial difference in mass loss between different degrees of acrylation of PGSA.

Figure 18:
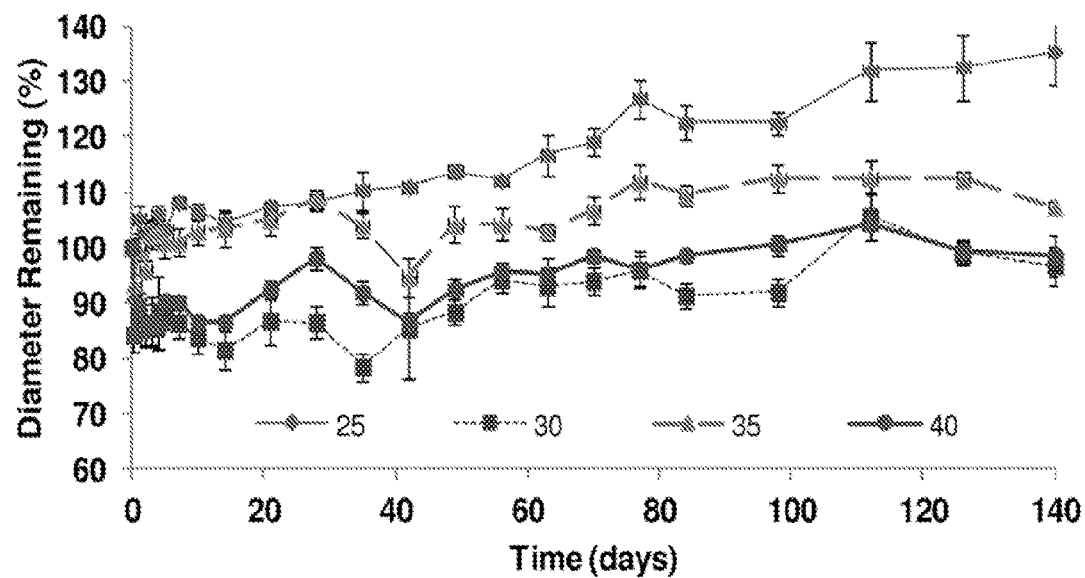

FIG. 18 graphically demonstrates an analysis of Degradation based on swelling of the polymer which indicates that all acrylations initially decrease in diameter followed by gradual swelling. For 25% acrylation, the swelling was more rapid with a final increase of 30% in diameter by 20 weeks; whereas for higher acrylations, swelling returned the discs to their original diameter by 20 weeks.

Figure 19:
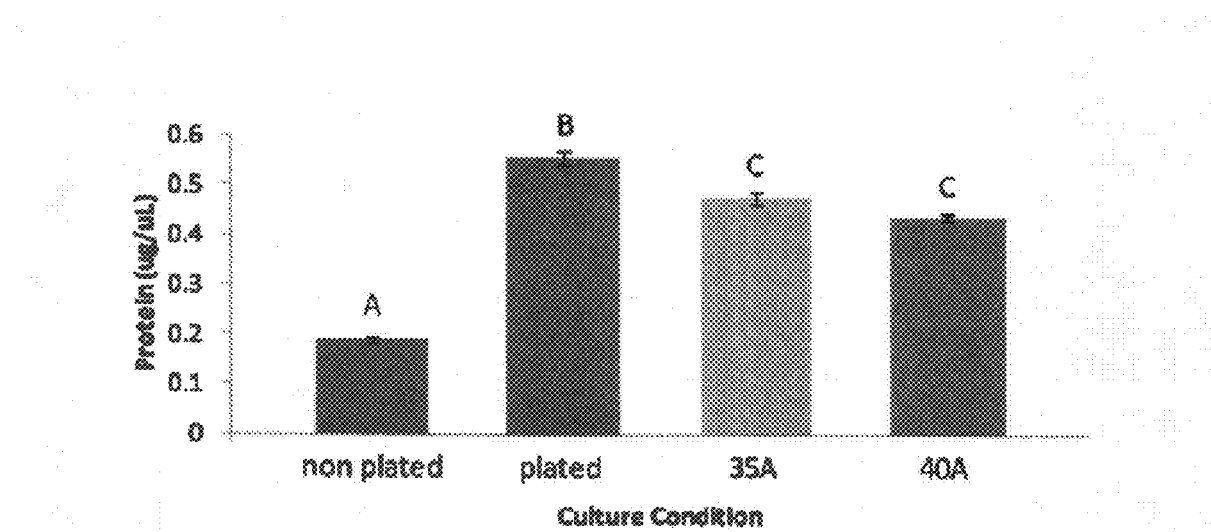

FIG. 19 demonstrates a BCA Protein Assay comparison of HEPM (fibroblast morphology) cells prior to plating (nonplated), and cells plated on tissue culture polystyrene, PGSA 35% acrylation, and PGSA 40% acrylation for three days growth. There was no significant difference between 35 and 40% acrylation. ANOVA analysis showed statistically significant differences (p<0.0001). Waller Duncan's post hoc analysis was applied to separate means with statistically significant differences (p<0.05). Means with the same letter are not significantly different.

Figure 20:
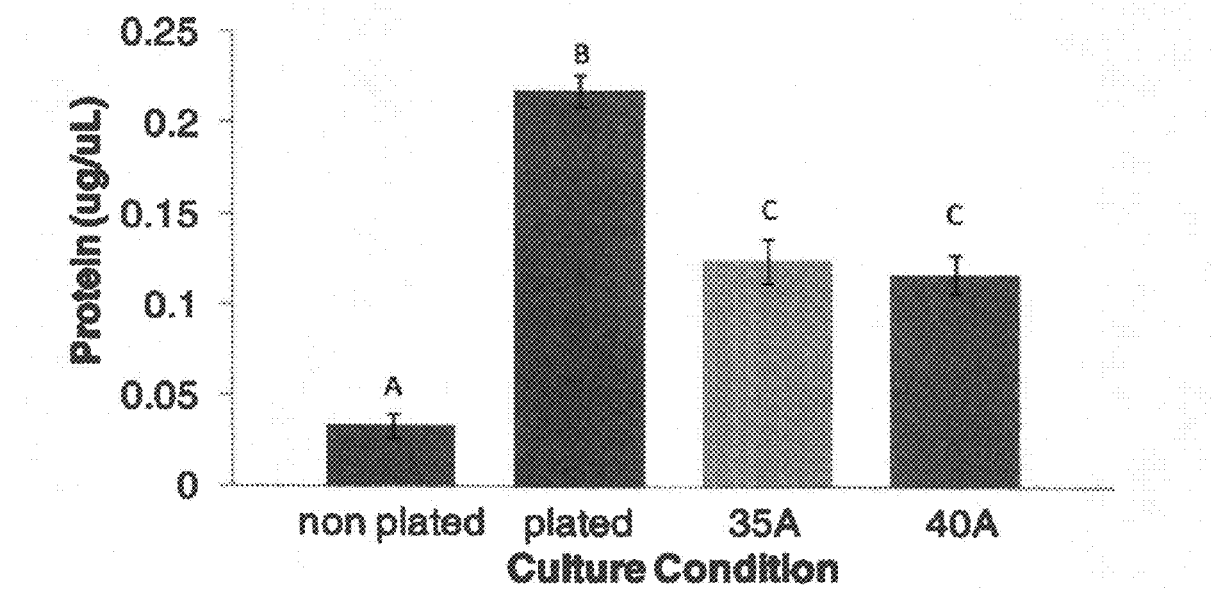

FIG. 20 demonstrates a BCA Protein Assay comparison of B35 (neuroblastoma morphology) cells prior to plating (nonplated), and cells plated on tissue culture polystyrene, PGSA 35% acrylation, and PGSA 40% acrylation for three days growth. There was no significant difference between 35 and 40% acrylation. ANOVA analysis showed statistically significant differences (p<0.0001). Waller Duncan's post hoc analysis was applied to separate means with statistically significant differences (p<0.05). Means with the same letter are not significantly different.

Figure 21:
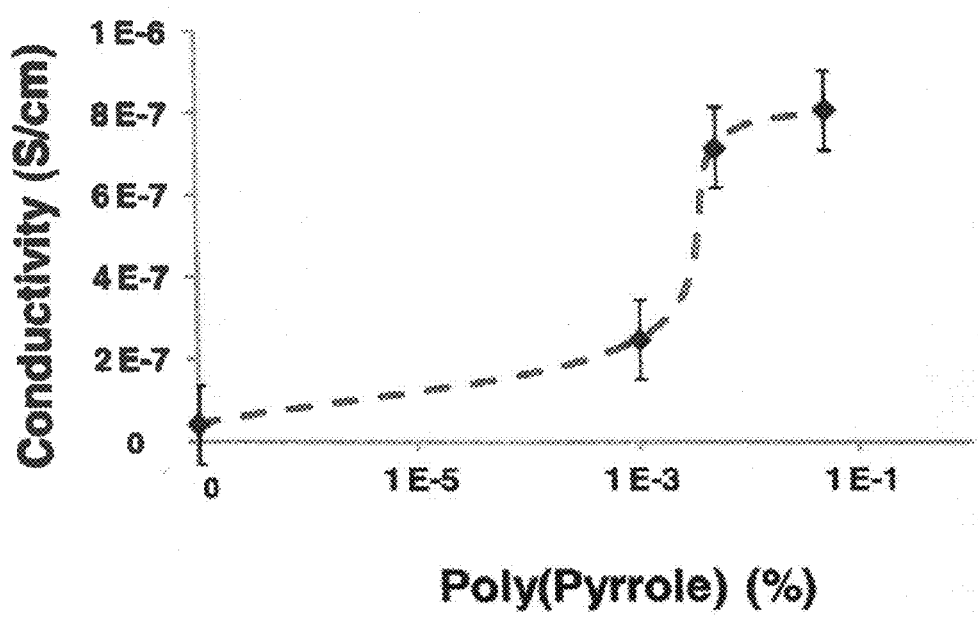

FIG. 21 demonstrates a conductivity comparison of PPy doped PGSA with 35% acrylation.

Figure 22:
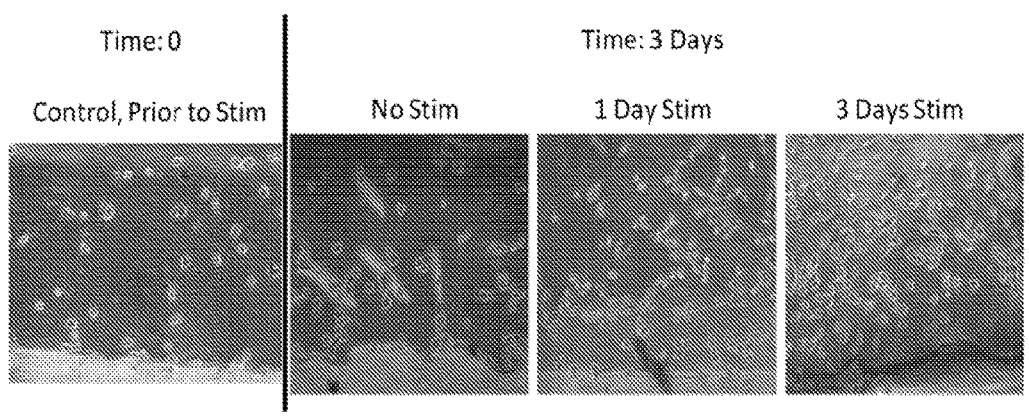
Figure 23:
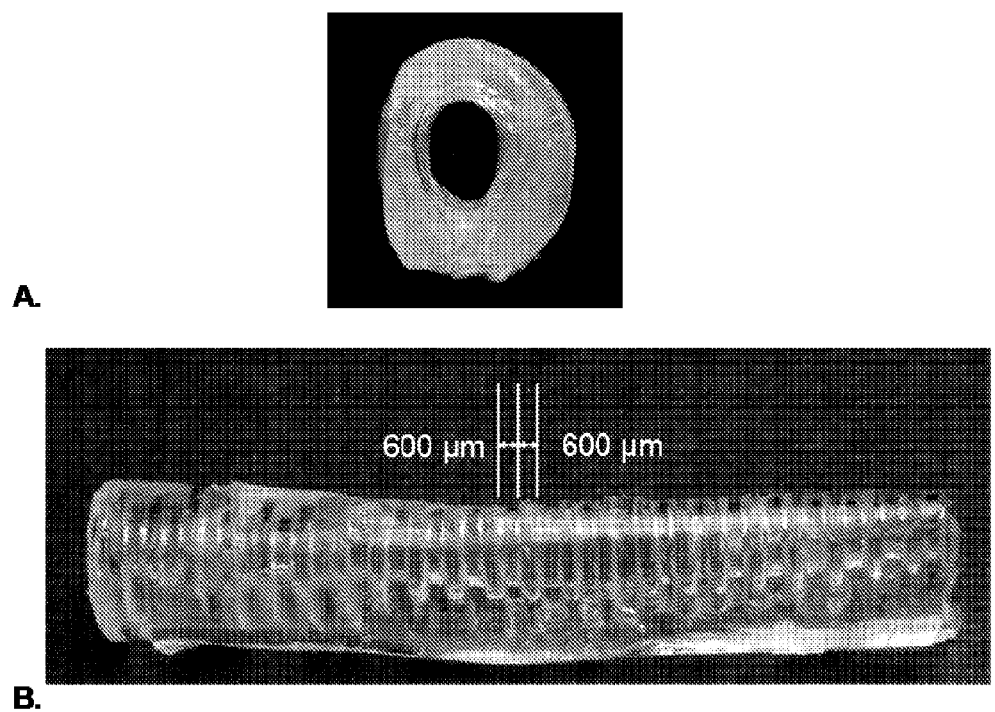

FIG. 22 demonstrates cellular replication, migration, and direction as influenced by biphasic sheets alone or with 1 or 3 days of electrical stimulation at 3V, 20 Hz. The treatment (i.e. treatment 1) demonstrated cellular adhesion (12 hours after plating) concentrated near the border of the low conductivity "hill" and the high conductivity "valley" on the sheets. After three days of cell culture, images indicated 3 days stimulation >1 day stimulation >no stimulation, FIG. 23 demonstrates the ormation of a biphasic conducting tube for nerve implantation. (A) Cross-sectional view demonstrating that the hole goes completely through the tube. (B) Transverse view illustrating the alternating high and low conductivity material sections which will permit transmission of high and low electric fields along the tube.

Figure 24:
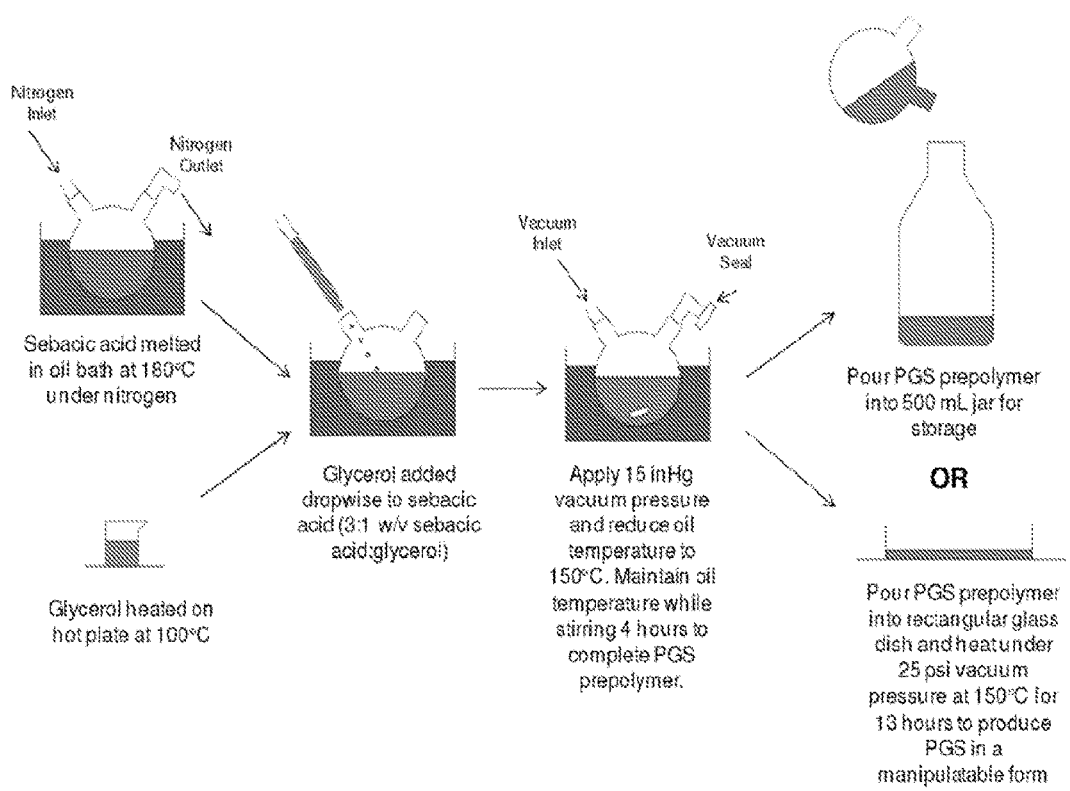

FIG. 24 schematically illustrates a method of synthesizing PGS.

Figure 25:
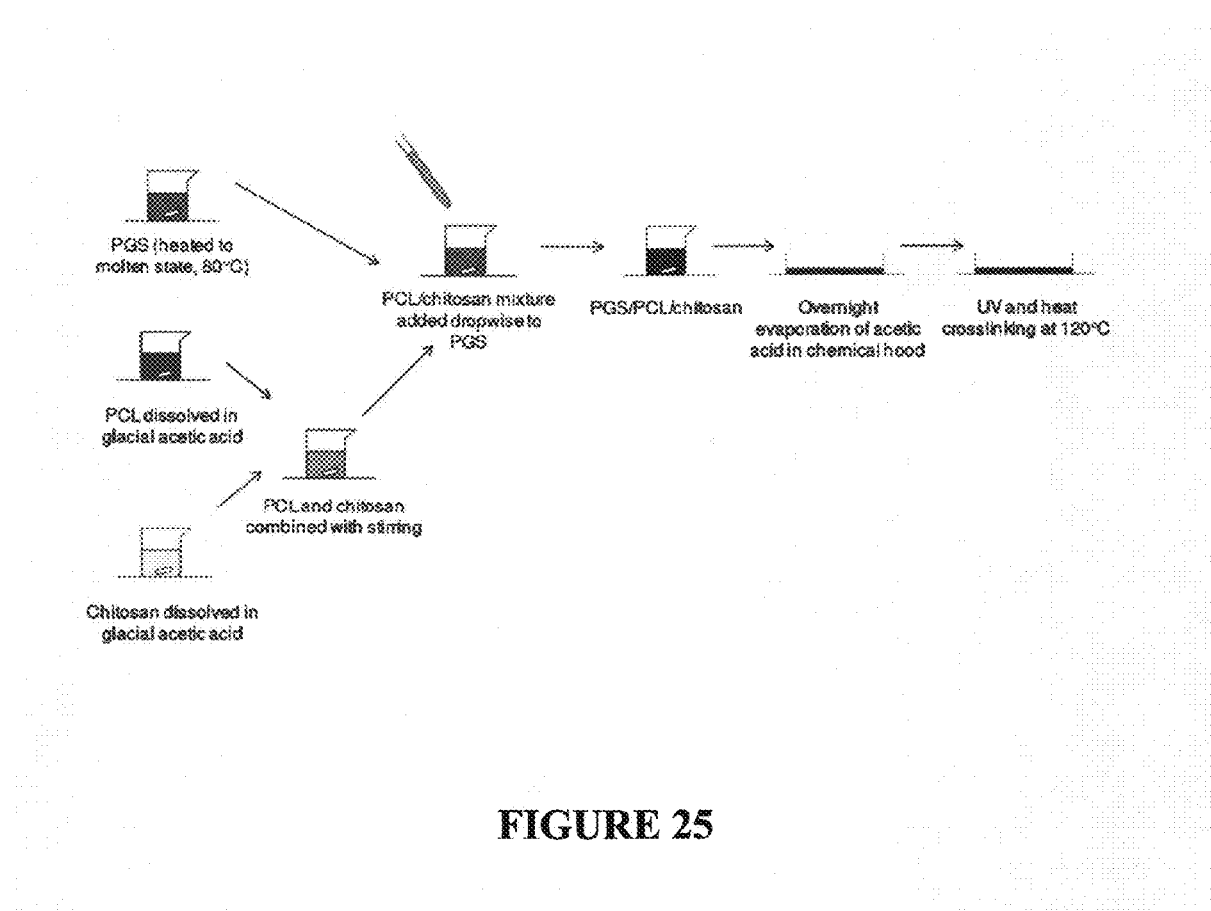

FIG. 25 schematically illustrates a method of preparing a copolymer. Specifically, a copolymer of PGS/PCL/Chitosan is demonstrated therein.

Figure 26A:
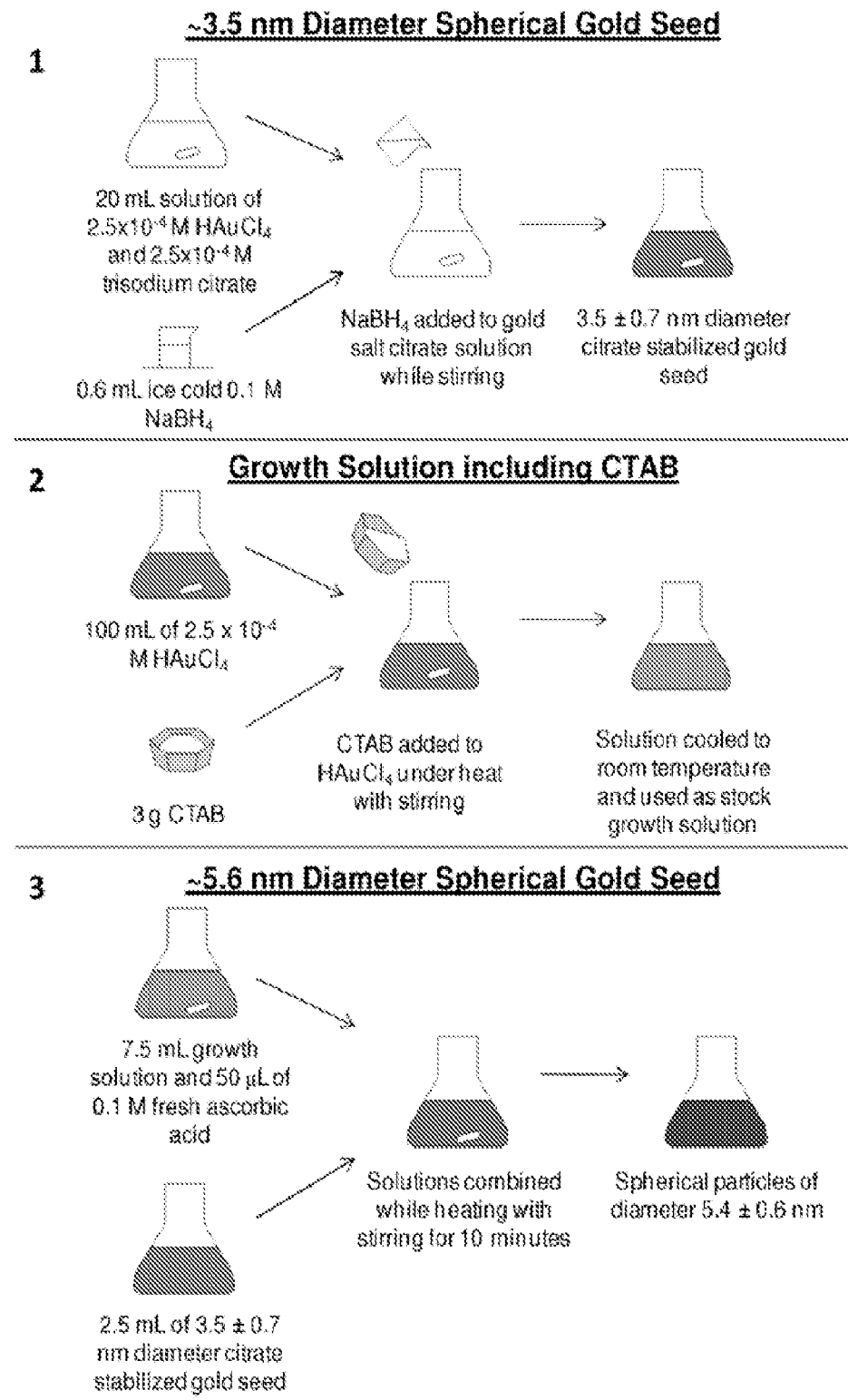
Figure 26B:
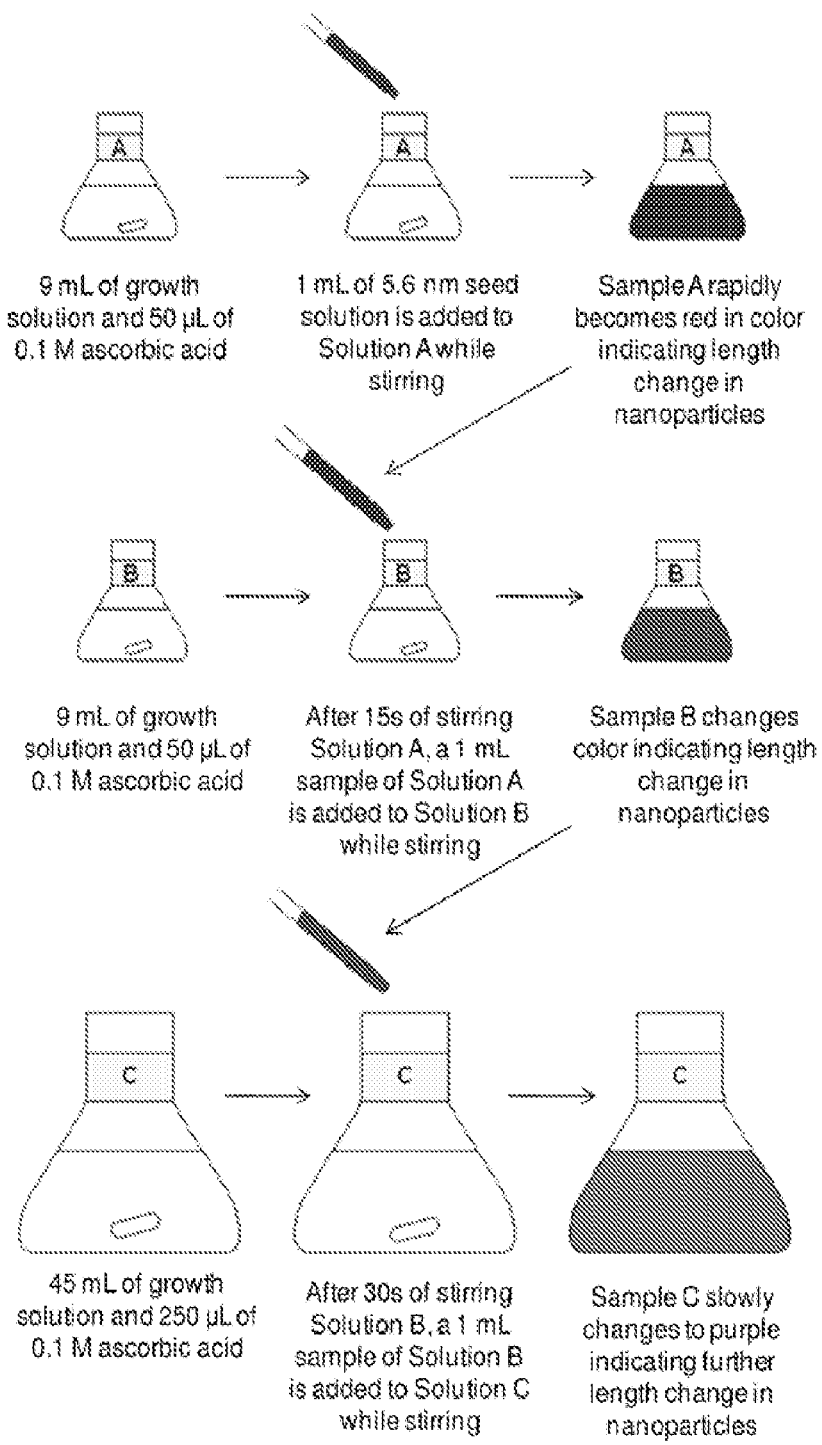

FIGS. 26A-26C schematically illustrate the multi-step synthesis of gold nanorods. Specifically, (A) the seed and growth solution preparation for gold nanorod synthesis; (B) the three step extension of seeds into gold nanorods; and (C) purification of gold nanorods.

FIG. 27 schematically illustrates a rectangular mold with vertical grid insert that may be used for segmented sheet preparation.

Figure 28:
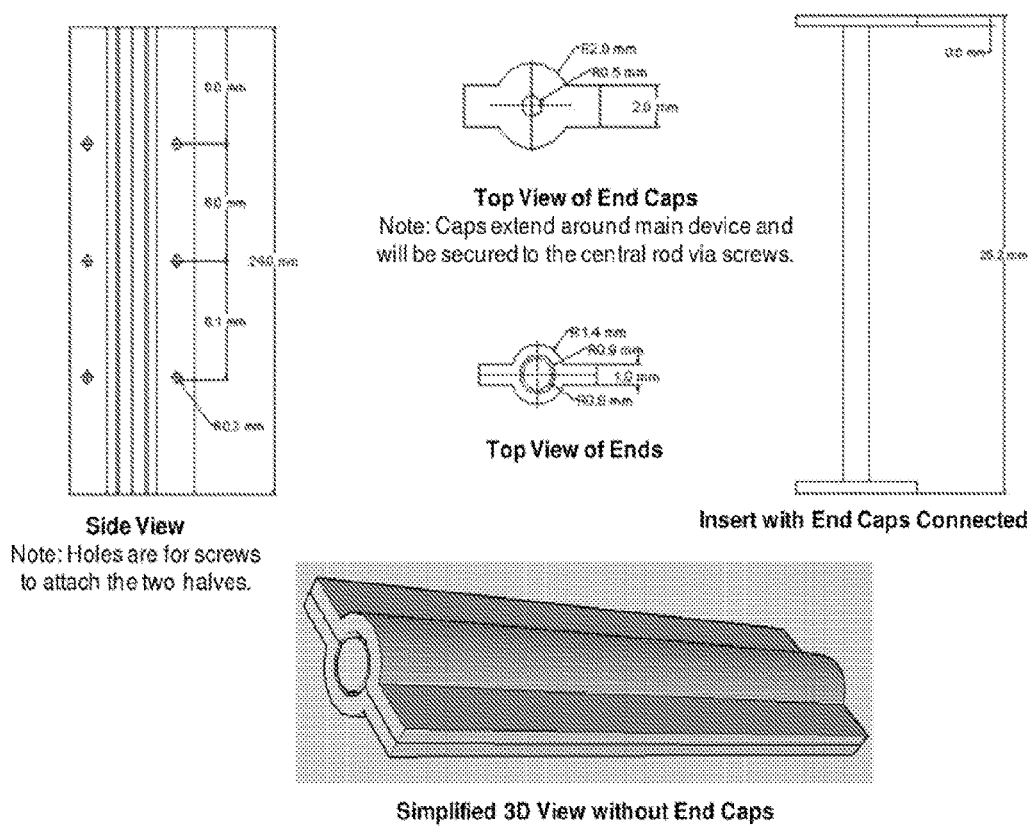

FIG. 28 schematically illustrates a tubular mold for conduit preparation.

FIG. 29 demonstrates an analytical method for evaluating cell-material response.

FIG. 30 schematically illustrates conduit sectioning for a cell viability assessment. Each conduit may be assessed for cell viability and activity for neurons and Schwann cells at 3 and 5 days after cell seeding. Each conduit can then be halved along the horizontal and vertical midsections and assessed.

FIG. 31 demonstrates an analytical method for comparison of influence due to voltage type (AC or DC) on neurite outgrowth.

FIG. 32 demonstrates an analytical method for comparison of varied stimulation patterns and their effect on neurite outgrowth.

FIG. 33 demonstrates an analytical method for comparison of conductive segment influence on neurite outgrowth.

FIG. 34 provides an explanation of the right hand rule, as discussed herein. Specifically, (A) x×y curls clockwise with direction along the positive z-axis; and (B) x×y curls counterclockwise with direction along the negative z-axis.

FIG. 35 demonstrates an analytical method for in vivo comparison of nerve repair following transection.

FIG. 36 demonstrates prospective animal usage necessary for the in vivo comparison of nerve repair following transection.

DETAILED DESCRIPTION OF THE INVENTION

Paralysis, desensitization, or extra sensitization of motor and sensory nerves is caused by peripheral nerve damage. Diseases (e.g., leprosy, diabetes, and HIV), therapies (e.g., chemotherapy and radiation), and injuries (e.g., trauma, brachial plexus, and stroke) are all sources of nerve impairment. In the United States, over 50,000 surgical procedures are reported annually for peripheral nerve repair. A lack of treatment options for large scale nerve damage (e.g., salvaged limbs) indicates countless unreported injuries. For the past 100 years, many experimental and clinical techniques have been investigated to improve repair of peripheral nerve. However, while new procedures and devices have extended surgical options, repairs are limited to a maximum nerve gap of 3 cm.

In development of the present invention that overcomes the failings of the prior art, a comparison was made of the differences between species' responses to nerve damage. The comparison demonstrates the presence and effect of electric fields on cellular activity. Observations from newt limb repair and bovine cornea regeneration, demonstrate that the capacity of electric field stimulation may be limited to about 600 μm zones of effectiveness. See, for example, FIG. 1. Newt regeneration is accomplished in a segmental manner which enables the specialized blastema tissue to control the length of repair. Without being restricted to any one theory, the present invention sets forth a series of electric field gradients throughout the wound region that promote elevated rates of axonal outgrowth. Moreover, the present invention sets forth segmental conducting conduits composed of bioresorbable polymers that generate a series of electric fields that extend gradients along an entire damage site. The series of electric field gradients eliminate the factor of short distance effectiveness provided from single point stimulation. Additionally, segmental conducting conduits are provided based on traditional measures of functional, electrical, and morphological changes. Molecular effects are also assessed to provide an understanding of electrical effects on pathways for nerve regeneration. Further, the present invention includes a mathematical model of the electrical field gradients to relate electrical stimulation effects to axonal outgrowth rate.

Surgical procedures for treating peripheral nerve damage fall within two major categories: grafts and conduits. A nerve graft ordinarily originates from the patient (autograft), or from living or cadaveric human donor tissue (allograft). Drawbacks to autografts include creation of multiple surgical sites, availability, and selection of grafts with similar size and structure of the damaged nerve. Allografts overcome several of the disadvantages of autografts, but require immune suppression or decelluarlization to prevent immune rejection.

Conduits are tubular alternatives to nerve grafts. Unlike grafts, conduits are prepared from natural or synthetic materials. Conduits are tailored to mimic the mechanical properties of natural nerve but lack the chemical, biological, and morphological guidelines provided by grafts. Neither current grafts nor conduits are capable of functional sensory nerve repair.

Nerve conduits were developed to isolate and evaluate axon outgrowth during nerve repair. The effect of isolation reveals conduits to be viable for clinical applications. Although originally constructed of silicone, nerve compression complications led to discontinued use of silicone. The FDA has approved a selection of biocompatible conduits for clinical use. Type I collagen (Neuragen, NeuroMatrix, and Neueroflex) and combinations of Type I and Type IV collagen (Revolnerv) can be constructed into porous conduits to generate natural, bioresorbable repair solutions. Additionally, synthetic materials have been employed to generate non-bioabsorbable (Salubridge) and bioabsorbable conduits. (Neurotube, Neurolac, Neurawrap). Synthetic materials included poly (vinylalcohol) (PVA) hydrogel, polyglycoloic acid (PGA) mesh, and poly(DL-lactide-ε-caprolactone). While these conduits were prepared from various materials with different bioresorbable capacities and porosities, all have similar limitations. None of the conduits used in the field are able to repair nerve damage greater than 3 cm in length. The terms "bioresorbable" or "bioabsorbable," as used herein, may refer to synthetic or natural materials, including biomaterials, which can be replaced in vivo by natural extracellular matrix proteins and/or may be absorbed or resorbed in vivo. Further, while motor function was recovered from conduit use, minimal, if any, sensory nerve repair was observed. Conduits have provided a protective shell for nerve regrowth, but they have shown that degradable, porous conduits were incomplete solutions for surpassing nerve repair limitations. Generation of material for nerve conduits has focused on developing and modifying polymers with tailored mechanical and degradative properties, positive cell responses, and electrical conductivity.

In a preferred aspect, the present invention sets forth the development of a bioresorbable tube capable of producing repeated electric field gradients with an applied stimulus that can provide for nerve outgrowth.

In the construction of the devices of the present invention, the materials that make up such devices were first considered. The present invention sets forth a biphasic material that comprises two polymers wherein the polymers have differing conductive properties.

Regarding the selection and development of polymer components encompassed within the scope of the invention, mechanical and degradative properties of experimentally evaluated materials are demonstrated in FIG. 2. Numbers following material types in FIG. 2 indicate molecular weights. Polymers with contrasting tensile strengths and elastic moduli have been combined to achieve targeted mechanical properties. Extensive healing time for long gap repair motivated the use of slowly degradable (up to one year) polymers such as poly(ester-urethane) urea (PEUU), modified PCL, and PEUU/PCL combinations. In addition to providing desired mechanical and degradative properties, PEUU, PCL and combinations have demonstrated positive cell-material responses, which reinforce their potential for biological application. Due to the physiologically conductive nature of nerve and the idea that charged surfaces promote neurite outgrowth, application of conductive materials has emerged in experimental conduits. FIG. 2 summarizes the conductive properties of select synthetic and natural polymers used for biological applications. Examination of polymer options for conduction has indicated tradeoffs between synthetic and natural materials. Synthetic electrically conductive polymers (e.g, polypyrrole, polyaniline, and poly(3,4-ethylenedioxythiophene)) are capable of conductivity in the range of about 5-200 S/cm but may not be favorable for long term neurite growth. Natural conducting polymers, such as, melanin, chitosan, and gum Arabic have positive cell response but lower conductivity and mechanical properties than synthetic counterparts. However, the drawbacks of negative cell responses and weak material and conduction properties indicate the need for alternate materials for with enhanced conductive properties.

A biphasic material, preferably a repeating biphasic material, of the present invention may comprise several polymer components. For example, the biphasic material may comprise a first polymer component and a second polymer component having different conductive properties. The polymers of the present invention may include PGS, an esterified poly(glycerol sebacate) (e.g., PGSA), glycolic acid, polydiolcitrate, poly(ester-urethane)urea, PCL, hydroxyapatite, hyaluronic acid, alginate, collagen, elastin, vimentin, laminin, fibrin, melanin, gum Arabic, polycaprolactonefumarate, poly(octane diol) citrate, lactic acid, or combinations thereof. Preferably, the esterified poly(glycerol sebacate) is PGSA. In preferred aspects of the polymer components of the present invention, at least one of the first polymer component and second polymer component comprises a bioabsorbable or bioresorbable polymer.

Moreover, conductivity or conductive properties of the polymer components may be augmented or enhanced. Indeed, the first polymer component may be doped or otherwise treated to include a dopant or conductive filler components such as a conductive or semi-conductive metal component and/or a conductive non-metal component, which increases the conductivity of the polymer.

Several materials, as defined above, may be used to augment or enhance the conductive properties of the polymer components of the present invention. For example, nanoparticles have been incorporated into polymeric constructs as a means of enhancing conductivity. When electrons have a minimally resistive path to follow, materials have maximal conductivity. Increased resistance occurs when materials have multiple pathways for current flow, bends and tapered/pointed features. The minimal resistance/maximal conductivity achieved by narrow, long, straight wires may be attained on the nanoscale via tube, rod, and wire shaped particles. Key conducting nanoparticles in the tube/rod/wire category are single walled carbon nanotubes (SWCNTs), multiwalled carbon nanotubes (MWCNTs), and metal nanowires and rods. The metals utilized in the present invention may include silver, gold, platinum or a combination thereof. In a preferred aspect, the conducting nanoparticles are nanorods. Nanorods and nanowires may have diameters from at least about 1 to 100 nm and may be distinguished from one another based on aspect ratios. A shape's "aspect ratio," as used herein, may be defined as the length of the major axis divided by the length of the minor axis. Nanorods have aspect ratios between about 1 to 20, whereas nanowires have aspect ratios greater than about 20. Nanoparticle conductivity is influenced by material composition, dispersion, and aspect ratio.

Although silver, gold and carbon are conductive materials, the order of conductivity may be defined as silver having the highest conductivity ($6.3 \times 10^5$ S/cm), followed by gold ($4.5 \times 10^5$ S/cm), and carbon ($0.7 \times 10^5$ S/cm). SWCNT and MWCNT are entangled tubes with aspect ratios between about 100-2000, and are typically about 95% carbon. Moreover, SWCNT and MWCNT have roughly equal conductivities. Additionally, the incorporation of SWCNT in polyethylene terephthalate (PET) showed that SWCNTs resulted in a $10^3$ increase in conductivity from $10^{-8}$ S/cm with PET alone to $10^{-5}$ with 0.5% SWCNT and a $10^6$ increase in conductivity with 3% SWCNT yielding a conductivity of $10^{-2}$ S/cm. Regarding metal nanomaterials, silver nanowires may be dispersed with length distributions from about 100 nm to 19 μm and aspect ratios from about 11 to 50. Gold nanorods may also be dispersed to achieve over 80% long nanorods (about 600 nm in length) with 70% of the aspect ratios between about 18 to 23. While silver nanowires achieve higher aspect ratio and longer lengths than gold nanowires and nanorods, the distribution of lengths and aspect ratio and longer lengths than gold nanowires and nanorods, the distribution of lengths and aspect ratios is much narrower for gold.

Low conductivity materials such as chitosan ($10^{-4}$ S/cm) can be enhanced by low concentrations (0-5%) of metal nanowires to achieve high conductivity materials. Silver nanowires with resulting solutions comprised of short nanorods (aspect ratio (A.R.): 6.1±0.64 nm), medium length nanorods (A.R.: 17.0±0.06), and long nanowires (A.R.: 34.02±3.01) have been synthesized. Low concentrations (0-5%) of the prepared silver nanorods may be incorporated into chitosan films to enhance conductivity by up to $10^{10}$.

Turning to other nanomaterial configurations, mats of pure silver nanowires may have conductivity of $2 \times 10^5$ S/cm and thick films $5 \times 10^6$ S/cm for wires of about 85 nm in diameter and having a length of about 6.5 μm. FIG. 2 summarizes gold nanorod conductivity singly and within polymer films. Accordingly, in preferred aspects of the present invention, the conductivity of polymer components of the invention may be increased by incorporating a nanoparticle comprising gold, silver, carbon, or a combination thereof.

Turning to polymer dopants or conductive filler components, electrically conductive polymers have been developed for applications ranging from solar cells to stimulation that can aid in biological repair. Moreover, the conductive non-metal components may include PPy, polyaniline, poly(3,4-ethylenedioxythiophene), polyacetylene carbon nanotubes, a silicate, or combinations thereof. In some embodiments, the PPy may comprise a dispersed or water soluble PPy. In accordance with the present invention, for example, due to the hydrophobicity of PGSA and maximal solubility of the dispersed PPy in ethanol, soluble PPy may be distributed in ethanol, then the ethanol based distributed PPy solution may then be added to the PGSA solution and further distributed to provide an example of a high conductivity material. Additionally, soluble PPy is preferred as a dopant because it may achieve high electrical conductivity properties to maximize nanocomposite conductivity and processing yield, while minimizing aggregation during preparation with a hydrophobic base polymer (e.g, PGSA) and minimizing dopant production cost.

For biological applications, strict mechanical properties are critical to emulate the function of tissue in need of repair and to permit biological tissue to replace implanted materials. Specifically, electrical stimulation across a peripheral nerve gap has been shown to upregulate chemical factors resulting in a three-fold increase in repair rate. The repetition of electric field gradients can overcome the present limitations in nerve gap repair.

To achieve repeating electric field gradients, a device comprising a biphasic material and having alternatively high and low electrically conductive polymers has been developed. To develop multiple electric field gradients, repeating biphasic conducting materials composed of polymer and materials which modify the conductivity of the same are prepared. The biphasic material of the present invention may be in the form of a tube, sheet, or strip having a thickness of at least about 0.1 mm to 1 cm. The length or area of the biphasic material is dependent upon the area of use and the application envisioned. However, for nerve conduits of the present invention, lengths may be at least about 1 cm to 20 cm. In preferred aspects, the biphasic material may be configured to form a tube, sheet or telescoping segmented apparatus or tube. In a most preferred embodiment, the biphasic material is configured to form a tube.

Two material phases of high and low conductivities are prepared in long and short segments, respectively. The term "high conductivity," as used herein, refers to those materials having a conductivity of at least about $10^{-6}$ to $10^{-4}$ S/cm. The term "low conductivity," as used herein, refers to those materials having a conductivity of at least about $0-1.25\times10^{-5}$ S/cm. Applied electric stimulation to the material produces high electric fields which gradually taper. Repeated biphasic sections produce a series of electric field gradients. Material selections may preferably be guided by known mechanical properties of native nerve (elastic modulus 0.4-0.7 mPa and tensile strength 1.1-1.7 mPa or 0.21-1.49 N), biodegradability within repair time (3-12 months), and conductivity based on epithelial measures of electric field and current density ($1.25\times10^{-4}$ S/cm).

As an example, chitosan is a natural polymer with conductivity between $10^{-5}$ and $10^{-4}$ S/cm but high tensile strength and elastic moduli. PGS, a degradable polymer with low elastic modulus and tensile strength, is combined with chitosan to achieve mechanical properties measured from native nerve. The resulting copolymer provides suitable conductivity for low conducting material. To produce high conducting segments, low concentrations (0-5%) of metal nanorods can be incorporated into the chitosan/PGS copolymer. Based on the effective length of electric fields from newt limbs and bovine cornea, long segments will be 600 µm in length. Short segment length is based on the length of squamous epithelial cells from sciatic nerve sheaths.

Electrical properties are assessed using optical and electronic measures. For example, a light microscope may be used to verify probe position for two oscilloscope inputs. A power supply may be used to apply 0.1-0.2 ms, 3 V stimulation to one end of the conducting sheet. Interfacing the oscilloscope outputs to a data acquisition system allows acquisition of the stimulation time (pulse distance) and amplitude (voltage) for probes along the sheet. Such experiments confirm the beneficial production of a series of electric field gradients using repeated biphasic conducting materials.

Turning to the activity of the repeating biphasic conducting materials themselves, alternated phases of long, high conductivity materials followed by short, low conductivity materials enable an applied electric field to taper, and then spike to restart the gradient. Appropriate lengths for long and short segments are approximated based on effective distances for promotion and direction of axonal outgrowth due to electric field gradients from epithelial cells and the length of squamous epithelial cells ensheathing sciatic nerve. The segments of the present invention may have a length of at least about 10 µm to 1200 µm. Preferably, the present invention includes long and short segments. Preferably, long segments may comprise lengths of at least about 600 µm and short segments may comprise lengths of at least about 10-600 µm. More preferably, the short segments may comprise lengths of at least about 10-40 µm. Additionally, the short segments may comprise lengths of at least about 20-40 µm. See, for example, FIGS. 3A and 3B.

There are various pattern types providing low and high conduction, depending on the types of materials used for construction of conduit. These may include various types of sheathed materials or materials seeded with various types of cells. Molding of polymeric materials may provide conduits with a branch design. Potentially, large diameter nerves can be targeted for repair with regard to the material blends other applications to design scaffolds for tissue repair can exist. One example is in bone repair. The conduits can be used to add specific structure to any tissue defect.

Indeed, the biphasic material of the present invention may be used for the repair of peripheral nerves, bone tissue and muscle tissue (e.g., skeletal muscle tissue and cardiac muscle tissue, where cells respond to electrical currents). Preferably, the biphasic material of the present invention may be used for peripheral nerve repair. Moreover, in sheet form, the biphasic material of the present invention can be used to promote peristalsis or weight loss following regional application to the patient.

Figure 3A:
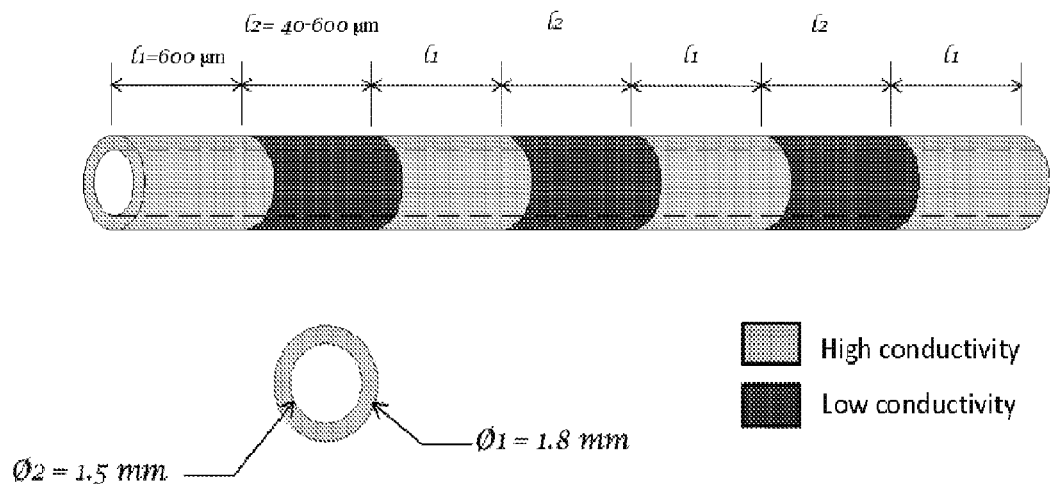
FIGS. 3A and 3B schematically illustrate tube conduits of the present invention. Specifically, (A) provides a tube conduit of the present invention wherein the high conductivity segment has a length ($l_1$) of 600 μm and the low conductivity segment has a length ($l_2$) of about 40-600 μm; (B) provides a tube conduit of the present invention wherein the high conductivity segment has a length ($l_1$) of 600 μm and the low conductivity segment has a length ($l_2$) of about 10-20 μm.
Figure 3B:
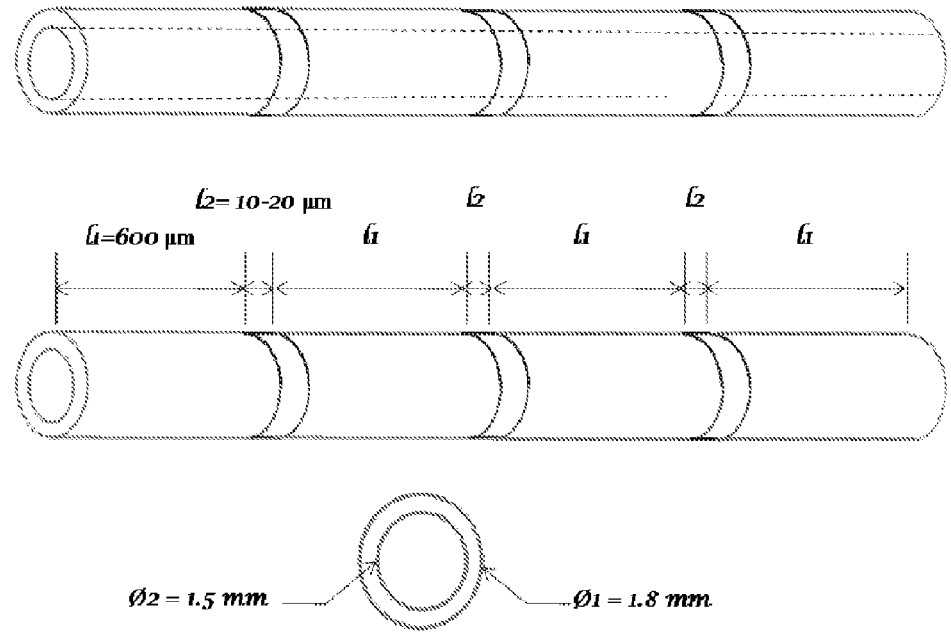

As stated above, in preferred aspects, the biphasic material may be used to develop a conduit for treating a transected nerve. There are at least two embodiments of the conduit of the invention: a tube and telescoping segmented apparatus or tube. The conduits of the invention can be utilized in various lengths to repair peripheral nerve and can be seeded with cells. In preferred aspects, the material utilized for development of the conduit has mechanical properties similar to peripheral nerves and demonstrates Young's Modulus between 0.4 to 0.7 milipascals and tensile strength from 1.1 to 1.7 milipascals. FIGS. 3A and 3B illustrate the first embodiment of the conduit of the invention which comprises a tube conduit. The tube conduit is provided as having a fixed length with repeating segments. (FIGS. 3A and 3B).

Figure 4:
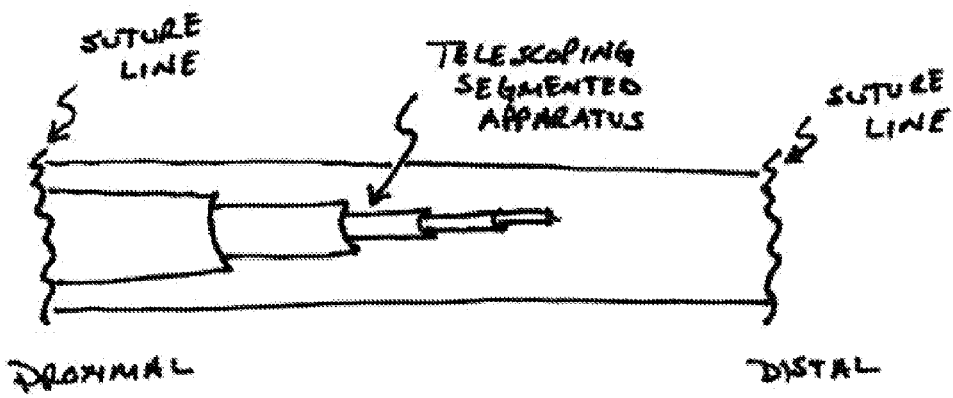
FIG. 4 schematically illustrates the positioning and structure of a telescoping segmented apparatus of the present invention.

A second embodiment of the invention is a telescoping segmented apparatus. In this case both high and low conducting materials will be located in each segment, but the addition of polymers responsive to electrical conduction will propagate the device through tissue as conduction of electrical impulse proceeds. This is demonstrated in FIG. 4. The telescoping apparatus or tube may comprise hyaluronic acid or other compatible materials. Also, extension of the telescoping segmented apparatus, when in use, can be driven through osmotic pressure. Indeed, as indicated in FIG. 4, rather than having a fixed length as in the tube embodiment, the telescoping segmented apparatus can be inserted in an un-telescoped state at the site of injury and then be "driven" or "telescoped" into an expanded position.

In another aspect, the materials of the present invention comprise scaffolds. More specifically, said materials comprising scaffolds may be prepared from nanocomposite materials. The scaffolds prepared from nanocomposite materials are designed to impart nano-scale features, such as fibers and pores. Multiple methods such as gelling, cryogenic linearization, solvent or salt leaching, inkjet printing and electrospinning may be used to develop the scaffold structure. Injectable, self-assembling scaffolds may also be used. All scaffolds are designed to provide a conductive, structurally supportive matrix for cell infiltration between the distal and proximal ends of a peripheral nerve.

To develop multiple electric field gradients, it is proposed that repeating biphasic conducting materials composed of resorbable biopolymers with a conductive filler component (or dopants), such as, metal nanowires be provided. Repetition of biphasic composites establishes a series of electric field gradients. Repeated biphasic conducting materials, which establish multiple electric field gradients, may eliminate the 3 cm restriction to enable nerve repair independently of the length of damage.

According to an aspect of the present invention to achieve appropriate mechanical properties emulating native human nerve tissue, electrically conductive, bioresorbable elastomers made of acrylated PGS are synthesized with 25, 30, 35, and 40% acrylation as verified by $^1$H-NMR. Tensile strength, elastic moduli, and elongation to break are evaluated via Instron 5500R mechanical tester to select the acrylation percentage of PGSA that matched the mechanical properties of native nerve tissue. Conductivity limits are calculated based on current density in native nerve and the electric field strength surrounding the nerve yielding a target high conductivity of about $1 \times 10^{-4}$ S/cm and a target low conductivity of about $1 \times 10^{-5}$ S/cm. Composites of PGSA with PPy or other dopants set forth herein (e.g., MWCNTs) are prepared with conductivity calculated from current and voltage measurements via 4 point probe. Using a ribbed silicone mold, high and low conductivity polymers are alternated and UV crosslinked to achieve repeated electric field gradients. See, as an example of the foregoing method, FIG. 5. The materials may be implanted into a rat model for peripheral nerve repair, opening the door for translation of tunable electrically conductive nano-composites in clinically relevant tissue engineering applications.

Additionally, the present invention allows for the ability of the polymer to facilitate cell ingrowth based on its properties of electrical conduction. Following seeding of conduit with cells or influx of stem cells into the conduit, the conduit will undergo resorption over time with the end result of repair of peripheral nerve greater than 3 cm in length. The conduit has the ability to produce electrical currents, to stimulate cell-cell interactions and elongation of axons to repair peripheral nerve. To our knowledge, there are no types of conduit materials that provide electrical conduction in a manner in which is designed for this particular purpose. A conductive, nano-structured biomaterial that allows for in vivo electrical stimulation from the proximal to distal ends of a nerve may encourage regeneration by promoting Schwann cell-neuron interaction resulting a subsequent axonal extension.

The bioresorbable materials of the present invention preferably degrade after about 3 months. More preferably, the bioresorbable materials of the present invention degrade after about 3-12 months.

The embodiments of the present invention are preferably applicable in surgical procedures to replace peripheral nerve. This would include cases that result from paralysis, desensitization or extra sensitization of motor and sensory nerves and the plethora of diseases which include leprosy, diabetes, HIV, chemotherapy radiation, trauma injuries, and stroke.

The following examples are provided to describe the invention in further detail. These examples are provided for illustrative purposes only and are not intended to limit the invention in any way.

EXAMPLES

Example 1

Figure 6:
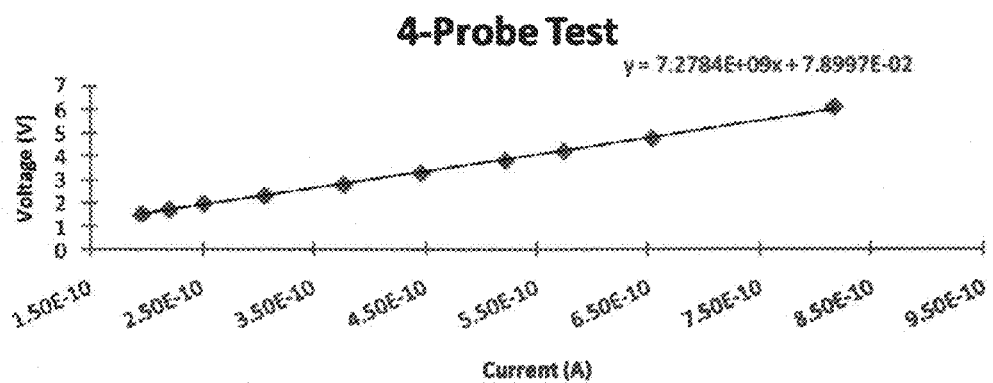
FIG. 6 demonstrates a 4-probe test where currents and voltages were measured across a silver doped chitosan film.
Figure 7:
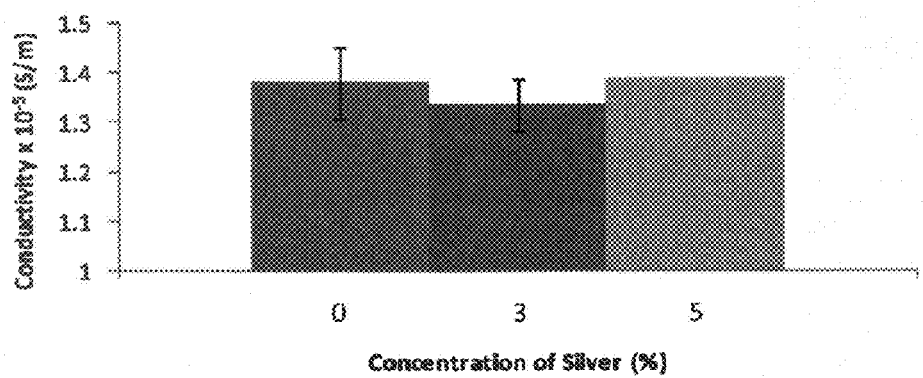
FIG. 7 illustrates a study comparing the conductivity of silver nanorod doped chitosan films.

Conductive materials can be enhanced by low concentrations (0-5%) of metal nanowires to increase material conductivity. We have synthesized silver nanowires with resulting solutions comprised of short nanorods (aspect ratio (A.R.): 6.1±0.64 nm), medium length nanorods (A.R: 17.0±0.06), and long nanowires (AR: 34.02±3.01). We incorporated low concentrations (0-5% by weight) of the prepared silver nanorods into chitosan films (conductivity=$10^{-6}$ S/cm) to evaluate changes in conductivity. We have achieved silver nanorods in the desired size range and successfully generated chitosan films doped with silver nanowires. (See FIGS. 6 and 7). Stable chitosan conductivity measures require input voltages in the range of 2 to 100 kV to achieve read voltages in the range of 2-100 V across the film. Distinction of conductivity for nanowire doping variation requires minimum input voltages of 10 kV. These input voltages are not reasonable options for human or animal modeling. These experiments can be repeated with polymers with higher conductivity at low input voltage ranges up to 10 V. It is expected that this range will allow distinction of conductivities between metal nanorod doped films.

Example 2

Figure 8:
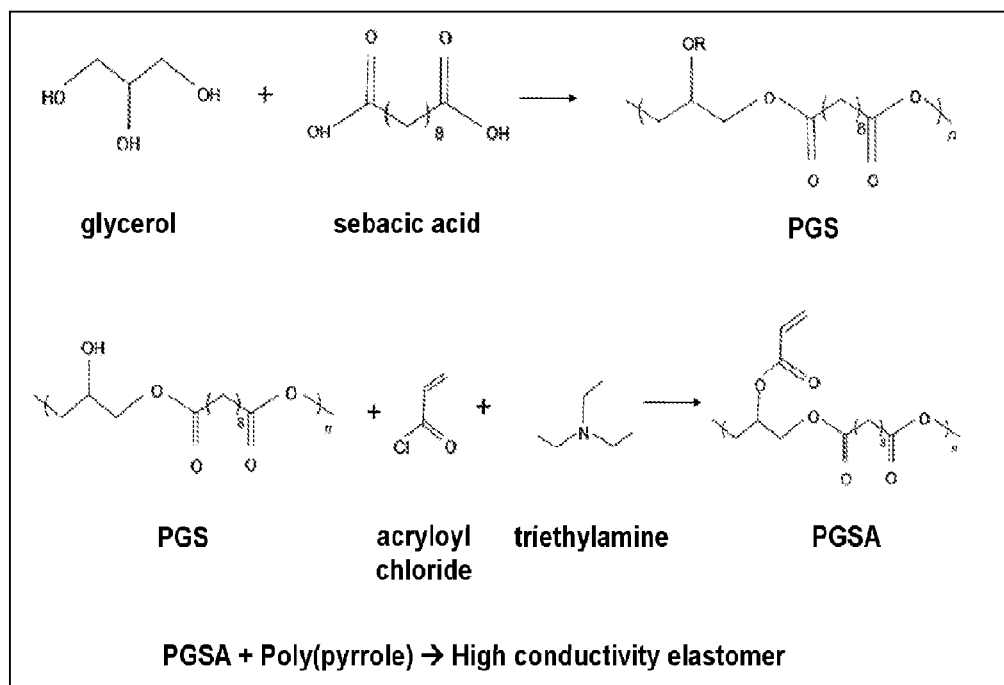
FIG. 8 schematically represents the synthesis of PGSA, an exemplary polymer component of the present invention.

A conduit of the present invention was prepared and tested utilizing PGSA. See FIG. 8.

Methods.

PGS was prepared by melting sebacic acid (Sigma 283258) in an oil bath at 180° C., under nitrogen. Glycerol (Fisher Scientific G33) preheated to 100° C. was added dropwise to sebacic acid (3:1 w/v sebacic acid: glycerol). The prepolymer was completed by applying 15 in Hg vacuum pressure while stirring 4 hours with the oil bath maintained at 150° C.

Synthesis of PGSA.

PGSA was prepared by melting PGS into an excess solution of dichloromethane (Fisher D37). PGS was acrylated to 25, 30, 35, and 40% of its hydroxyl groups using 25, 30, 35, or 45% molar amounts of acryloyl chloride (Sigma A24109). Hydrochloric acid was removed from equilibrium via vaporization with the dropwise addition of triethylamine (Sigma T0886) (1.2:1.0, triethylamine:acryolyl chloride). Dichloromethane was removed by rotovaporization. Triethylamine salts were precipitated from the solution using excess ethyl acetate (Fisher E195) followed by filtration. The filtered solution was rotovaporated again to remove ethyl acetate. Further ethyl acetate removal was completed by heating and stirring solutions under vacuum pressure for 72 hours. Solutions were stored at room temperature in the dark.

Polymer Preparation.

UV curing of PGSA requires use of a photoinitiator, 2,2-Dimethoxy-2-phenyl-acetophenone (Sigma, 196118) (DMPA). Prior to adding to molds 1% (w/w) DMPA was added to PGSA. A heat gun was applied to the solution until it boiled to facilitate DMPA incorporation without further solvent addition. PGSA was poured into plastic molds lined with parchment paper for ease of polymer removal. The polymer was crosslinked by exposure to UV light (about 28 mW/cm$^2$, model 100AP, Blak-Ray) for 20 minutes.

Polymer Characterization.

Nuclear Magnetic Resonance (NMR) was performed using a Bruker 300 MHz NMR to confirm consistency between polymer batches and to calculate the degree of acrylation for PGSA. PGS was assessed after processing the prepolymer and PGSA was assessed after removal of ethyl acetate as indicated by a solid polymer following cooling to room temperature. For both, 20 mg of polymer was dissolved in deuterated chloroform. Samples were assessed using MestRec v.4.9.9.5. The degree of acrylation was calculated and characterized using $^1$H-NMR spectroscopy. Briefly, PGS and PGSA peaks differ by the presence of three acrylate peaks located at 5.9, 6.1, and 6.4. The calculated integrations for sebacic acid located at peaks 1.3 and 1.9 ppm were 8 and 4, respectively. Measured integration peaks at 1.3 and 1.6 were summed and divided by the calculated integration, 12. Acrylations performed at 25, 30, 35 and 40% were expected to yield three peaks at 5.9, 6.1 and 6.4 ppm of equivalent integration of approximately 0.25, 0.30, 0.35 and 0.40, respectively. The three vinyl peaks were integrated separately with calculated values of one each for 100% acrylation. Vinyl integrations were summed and divided by three to attain the average vinyl integration. The average vinyl integration was then divided by the calculated relative sebacic acid integration to determine the percent acrylation for each polymer.

Differential scanning calorimetry (DSC), a thermogravimetric assessment, was used to determine changes in polymer state with respect to changing temperature. Analysis of elastomeric polymers dictated assessment of the temperature range during which the polymers maintained rubber state, indicated by the glass transition temperature ($T_g$). A DSC Q 200 (TA instruments) assessed samples in Tzero pans and lids using a 3 cycle heat, cool, heat approach, namely (0 to 40° C., 40 to −60° C., −60° C. to 40° C.). Universal Analysis software (TA Instruments) was used to analyze output data for $T_g$. Briefly, $T_g$ was determined by identifying the linear region prior to the melt curve. Maximum and minimum points were selected based on the plateau region before and after the slope. $T_g$ was calculated by finding the slope of the line between the plateau regions.

Thin film X-ray Diffraction (XRD) collected angular scatter which allows the atomic structure of molecules to be resolved. Using an XRD Bruker Hi-Star Diffractometer structure changes were observed for heat polymerized PGS and UV polymerized PGSA 25, 30, 35, and 40% acrylation. Samples of thin films of the polymers were cut into 2 mm diameter circles using a punch biopsy. Diffraction was captured using GADDS software with three minute exposures in transmission mode with rotation. Diffraction patterns were Fourier transformed using EVA software to generate output as intensity with respect to. the 2θ angle. XRD polymer assessment yields broad peaks but can still yield useful information about the change in polymer structures with dopants or structural changes by comparison of peak intensity at 20.

A JASCO FT/IR 460 Plus Attenuated Total Reflectance-Fourier Transform (ATR-FTIR) Spectrometer was used to capture the reflected bond energy of a molecule due to vibrations caused by infrared stimulation. ATR-FTIR was used to compare changes in bonds of PGS and the acrylated PGS molecules. Crosslinked polymer disks (2 mm diameter) were placed on the diamond crystal under contact pressure to remove air/crystal contact. Data were output as intensity (arbitrary units, a.u.) with respect to wavenumber (cm$^{-1}$). Crosslinked PGS was used as a baseline for the non-acrylated polymer bonds. Peaks for acrylation bonds were possible in the ranges 1125-1225, 1250-1325, and 1700-1750 cm$^{-1}$.

Features important to the claimed invention and integral to the application of biopolymers for surgery are flexibility, maximal applied force and stretch distance. Tensile testing provides outputs which allow calculation of mechanical properties, such as, elastic moduli, tensile strength, and elongation to break, which directly answer the above features. An Instron 300 R Mechanical Tester and an Electro-Force 3100 Test Instrument (Bose) were used to characterize the mechanical properties of the PGS and the PGSA, respectively. PGS samples were heat crosslinked into thin sheets and stamped into dog bone shapes per ASTM standard D-638-IV. PGSA samples were heat crosslinked into thin sheets and stamped into dog bone shapes similar to ASTM D-638-V with dimensions 1×3.5 cm. Smaller samples were necessary for PGSA due to limited polymer batch sizes. All samples were evaluated at a rate of 50 mm/min with a 500 N load cell. Tensile strength values came from the polymer's maximum load. Elastic moduli (Young's moduli) were identified by calculating the stress and strain curves and finding the slope of the steepest linear section of the curve through least square's fit. Elongation to break was calculated based on the extension of the polymer at the point of break. To evaluate mechanical properties post treatment for cell culture and in vivo implantation, samples were either treated with 1) 3, 1 hour washes of ethanol followed by 3, 1 hour washes of PBS to remove unreacted agents or 2) 15 minute washes of gradated ethanol (30, 40, 50, 60, 40, and 20%) followed by triplicate, 15 min PBS washes. Following treatment, samples were subjected to tensile testing under the same conditions as used for untreated samples. Samples prepared via treatment one were evaluated for degradative properties using 3 mm diameter discs which were placed into 30 mm culture plates or 20 mL tubes with PBS. Diameters of samples placed in dishes were measured via digital calipers for swelling daily through day 7, then weekly until 150 days. Samples placed in tubes were lyophilized and weighed to assess change in mass daily through day 7, then weekly until 150 days. All were performed in triplicate.

Statistical analysis was conducted using SASS with Enterprise Guide. Samples were compared via ANOVA with Duncan's multiple range test for post hoc evaluation.

Cellular Compatibility.

Unreacted components were removed from samples prior to cell culture via 1) 3-1 hour washes of ethanol, followed by 3-1 hour washes of sterile PBS or 2) 15 minute washes of gradated ethanol (30, 40, 50, 60, 40, and 20%) followed by triplicate, 15 min PBS washes. Samples were warmed to 37° C. two hours prior to cell seeding. Cells were seeded into 6 well plates with 100,000 cells per well. Three additional vials were prepared with 100,000 cells each using lysis buffer to get a baseline of initial cell protein prior to division. Vials were frozen at −80° C. for evaluation with other cells. Seeded cells were plated onto tissue culture polystyrene with no sample (control), a disc sample of 35% acrylation, and a disc sample of 40% acrylation. Media was changed daily and cells were lysed after three days. A standard curve was established with dilute protein samples from 0.5 to 20 μg/mL. Cell samples were added to a 96 well plate at 10 μL per well in duplicate. BCA Reagents A and B were added 50:1, respectively, with 200 μL per well. Samples were incubated 30 minutes at 37° C. and read at 562 nm using a TECAN infinite M200. Samples were evaluated using both HEPM (fibroblast morphology) and B35 (neuroblastoma morphology) cell lines.

Electrical Conductivity.

Samples of 35% PGS were preprepared in 35 mm petri dishes lined with parchment paper. Each disc comprised 1 g of PGSA with 0.1% DMPA dissolved. Doped polymer solutions were prepared using either carboxylated MWCNTs (CheapTubes) or chemically crosslinked PPy synthesized from pyrrole (Sigma Aldrich, W338605) doped with dioctyl sulfosuccinate sodium salt, $C_{20}H_{37}NaO_7S$ (Fisher Scientific, AC 11710-0025). Briefly, PPy (here PPy-DEHS) was synthesized by dropping freshly distilled pyrrole (0.4 mol) into a chilled $Na^+DEHS^-$ (0.15 mol) solution in 18 MΩ water (900 mL in a 1 L beaker) with continuous stirring. A chilled solution of 0.10 mol of ammonium persulfate, $(NH_4)_2S_2O_8$ (Fisher Scientific, BP179), in 100 mL 18 MΩ water was dropped into the chilled solution of pyrrole and $Na^+DEHS^-$ and maintained at 4° C. for 20 hours with continuous vigorous stirring. The dropped PPy precipitate was filtered using #40 filter paper and washed with 4 L 18 MΩ water.

Additionally, polymeric samples for electrical testing prepared as thin (m) discs (9.5 cm Ø). To produce discs, solutions of 0, 0.001, 0.005, 0.05% (wt/wt) of PPy in PGSA, ethanol based PPy solutions (bath and horn sonicated, 1 hr each) were added to PGSA/DMPA/ethanol solutions. Combined solutions were bath and horn sonicated (1 hour each) and poured into parchment paper lined dishes for overnight solvent evaporation followed by 20 minutes of UV crosslinking (ca 28 mW/cm², model 100AP, Blak-Ray,). Disc volume resistance (R) was measured via Keithley Model 65 High Resistivity Test System (V range=10 V, i=100 nA, 500 readings per sample) and sample thickness (t) using digital calipers to obtain $R_{avg}$ and $t_{avg}$, respectively. Conductivity was calculated using $t_{avg}/R_{avg}$.

Briefly, MWCNT solutions were prepared in 18 MΩ water (2 mg/mL) with 0.1% Pluronic and horn sonicated 30 min at 35% amplitude (2 s on, 2 s off). PPy solutions were prepared in chloroform (Fisher Scientific, C603) (1.1.33 mg/mL) with 0.1% Pluronic and horn sonicated 30 min at 35% amplitude (2 s on, 2 s off). Since PGSA is hydrophobic, PGSA was dissolved in 200 proof ethanol (1:1, vol/vol) in order to be combined with MWCNT solutions. PGSA dissolves well in chloroform so PGSA was dissolved in chloroform (1:1, vol/vol) for combination with PPy solutions. Solutions were prepared as 0.001, 0.005, 0.01, 0.05, 0.1, 0.5, 1.0 and 5.0% (wt/wt) of either MWCNT or PPy in PGSA. For cases in which the MWCNT solution volume was greater than that of the PGSA solution, additional 200 proof ethanol was added to the PGSA solution to prevent polymer precipitation. Combined solutions were horn sonicated 5 minutes at 35% amplitude (2 s on, 2 s off) and poured into 35 mm petri dishes lined with parchment paper. All solutions were left overnight in a fume hood to allow solvent evaporation. Following solvent evaporation, samples were UV crosslinked for 20 minutes.

Conductivity was found by measuring conductances using a Delcom 717 Conductance Monitor. Samples were placed between two pieces of weight paper and measured five times each. Conductivity was calculated by dividing the Mhos/sq by the thickness of the sample. Statistical analysis was conducted using SASS with Enterprise Guide. Samples were compared via ANOVA with Duncan's multiple range test for post hoc evaluation.

Biphasic Sheet Preparation.

Development of the biphasic sheet required the preparation of a mold from which polymer could easily release. Preparation of a sheet mold began with a Delrin inverse mold with spacings 600 μm wide and 400 μm deep. (FIG. 9A.) Using Sylgard 184 Silicone Elastomer Kit (Dow Corning, Midland, Md.), silicone molds were cast using the Delrin mold to obtain thin flexible sheets with the desired spacings which could be used to create tubular molds in the future. (FIG. 9B-C) Low conductivity polymer was injected into the valleys of the mold and the top was coated with high conductivity polymer (FIG. 9D). Sheets were crosslinked for 20 minutes under 365 nm, 30 W/cm2 UV irradiation (FIG. 9E) to obtain a final biphasic sheet (FIG. 9F).

Cell Stimulation Setup.

Using a Dremel tool, the inner edges of the two central wells of a six well cell culture plate (Costar 3516, Corning, N.Y., Fisher Scientific) were removed to open space for placement of an electrical stimulator. Two sets of holes were drilled across the tops of the four remaining wells. Teflon coated stainless steel wires (792400, A-M Systems, Inc.) with bared middle sections were placed through the holes to enable stimulation across each well and secured with hot glue. A 20×20 mm square of pretreated, biphasic polymer was inserted into each well and secured by pressing the wires into a high conductivity material valley at each end of the square. A 3V, 20 Hz square wave pulse generator circuit was designed and tested in our lab, and replicated by Micro Circuits Diversified, Inc. (Statesville, N.C.). The circuit was enclosed in a plastic sleeve to protect components from the humid environment. Positive and ground wires were connected to the circuit. Well plates and lids were sterilized via ethylene oxide prior to cell culture.

In Vitro Stimulation.

Cells were seeded into 6 well plates with 300,000 cells per well (B35, neuronal morphology). Seeded cells were plated onto tissue culture polystyrene with no sample (control) or biphasic material. After 12 hours to allow attachment, circuits were activated and cells were imaged at 12 hour intervals for 3 days. For single day stimulation, the circuits were deactivated after 24 hours of stimulation. For three day stimulation, the circuits were deactivated at the end of three days stimulation. Samples were imaged via Olympus inverted microscope using Open Lab software. Cells were counted based on region of valley occupied to supply a measure of cell spreading during the division process across the region's electric field.

Biphasic Tube Preparation.

Figure 5:
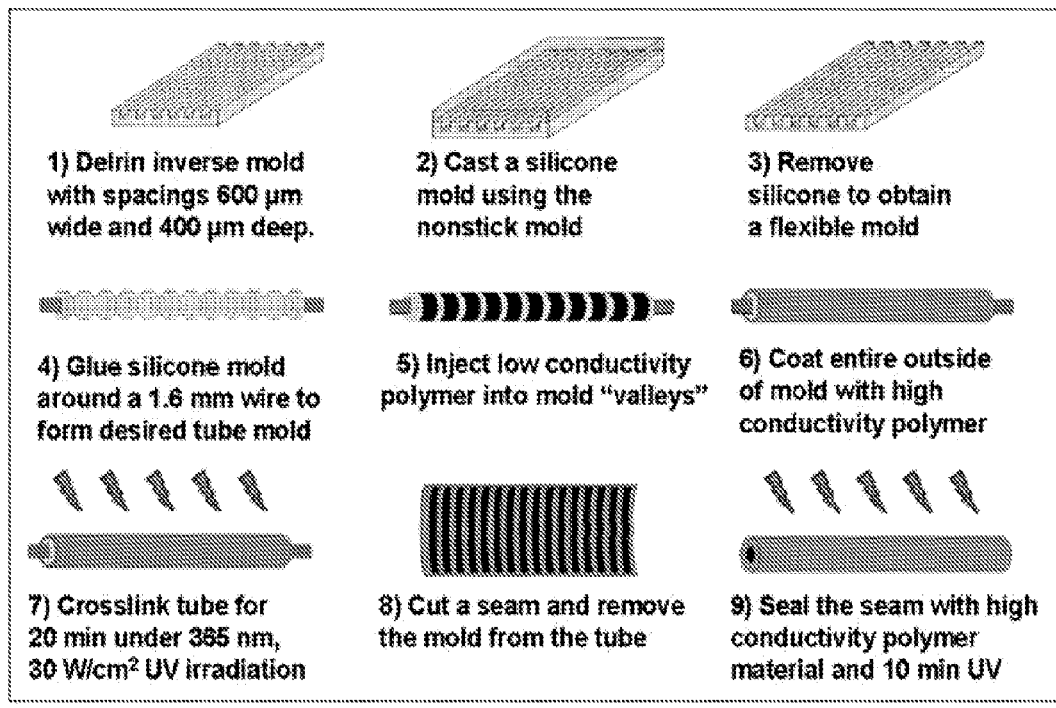
FIG. 5 graphically illustrates the preparation of a tube comprising the biphasic material of the present invention.

Similar to the biphasic sheets, preparation of a tubular mold began with a Delrin inverse mold with spacings 600 μm wide and 400 μm deep. (FIG. 5, step 1) Using Sylgard 184 Silicone Elastomer Kit (Dow Corning, Midland, Md.), silicone molds were cast using the Delrin mold to obtain thin flexible sheets with the desired spacings which could be used to create tubular molds. (FIG. 5, steps 2 and 3) The silicone mold was glued around a 30 G wire to form the desired tube mold. (FIG. 5, step 4) Low conductivity polymer was injected into the valleys of the mold (FIG. 5, step 5) and the entire outside of the tube was coated with high conductivity polymer (FIG. 5, step 6). Tubes were crosslinked for 1 minute under 365 nm, 30 W/cm2 UV irradiation with constant rotation. A second coating of high conductivity polymer was applied and the tubes were again crosslinked one minute with constant rotation followed by 4, 5 minute quarter turns of the tube under constant UV irradiation. (FIG. 5, step 7) A seam was cut longitudinally along the tube to remove it from the mold (FIG. 5, step 8) and the seam was sealed using high conductivity polymer and 10 min UV irradiation (365 nm, 30 W/cm2) (FIG. 5, step 9).

Results $^1$H-NMR Characterization of PGS and PGSA.

PGS was assessed via $^1$H NMR to confirm consistency with previously reported $^1$H NMR. (FIG. 10A) PGSA prepared from acrylated PGS prepolymer was assessed $^1$H NMR and compared to PGS prepolymer results, as well as, previously reported $^1$H NMR. (FIGS. 10B to 10E). PGS prepolymer was consistent with previously reported 1:1 sebacic acid to glycerol ratio. PGSA acrylation was designed to produce 25, 30, 35, and 40% acrylated prepolymer. Actual vinyl peaks (5.9, 6.1, and 6.4 ppm) were found to have an average integration of 0.23, 0.25, 0.33 and 0.36, respectively. (FIG. 10). Sebacic acid integrations (1.2, 1.5, and 2.2 ppm) were 11.43, 10.81, 11, and 10.87 with calculated relative sebacic acid integrations of 0.9525, 0.9008, 0.91, 0.9058, respective to 25, 30, 35, and 40% designed prepolymers. (FIG. 10) Final calculated acrylations were then 24.1, 27.7, 36.2, and 39.4% acrylated PGSA. These values are reasonable with consideration to $^1$H NMR error in integration being up to 10%. With error in mind these values can be reasonably referred to as 25, 30, 35, and 40% acrylated PGSA. Consistency with batches was verified using $^1$H NMR for all prepared PGSA. PGSA within calculated range for designed acrylation was used for further experimental analysis.

Structural Characterization of Crosslinked PGS and PGSA.

Figure 11A:
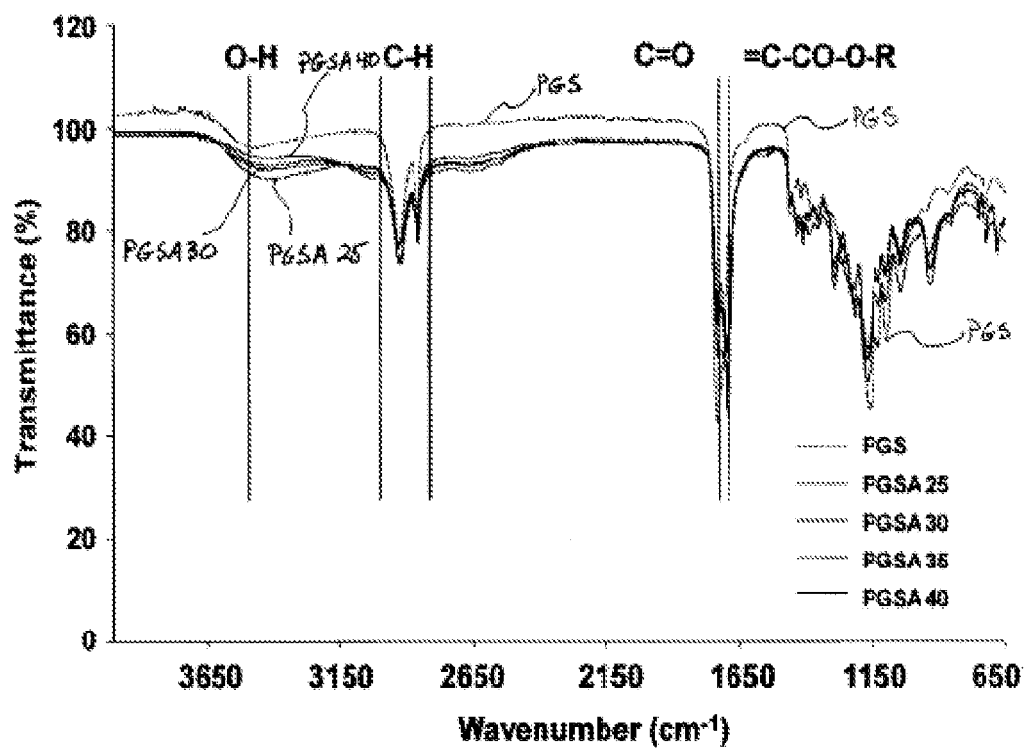
Figure 11B:
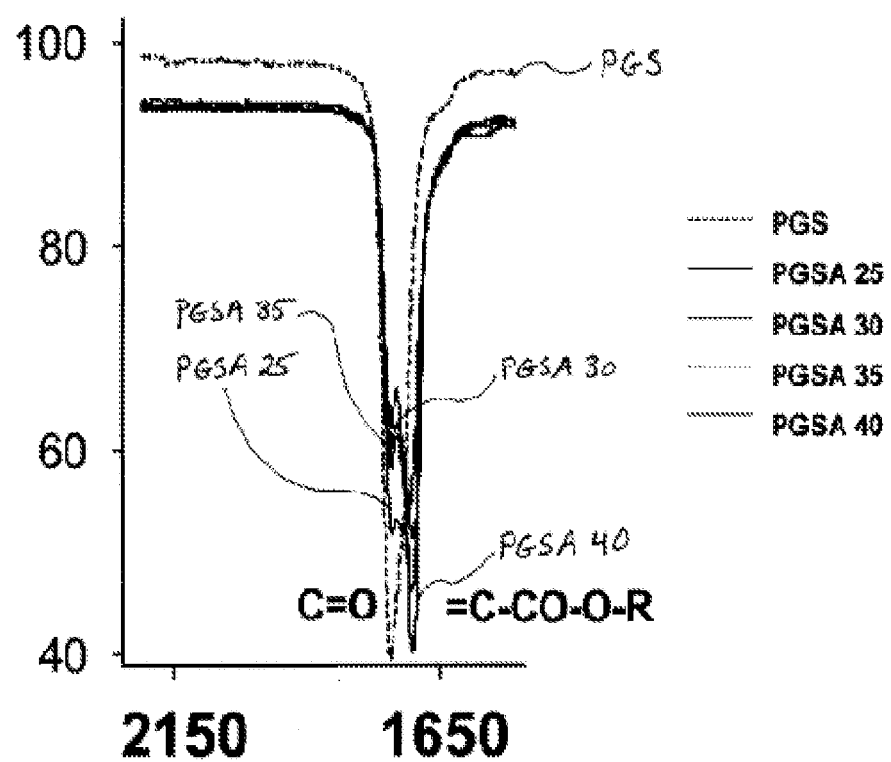

ATR-FTIR was used to confirm incorporation of acrylation of PGS by comparison of UV-crosslinked PGSA and thermally cured PGS. (FIGS. 11A and 11B). For PGS, the C=O bond was observed at 1700, stretch observed from 2850 to 2920 was attributed to C—H, and the O—H stretch was observed around 3300. (FIGS. 11A and 11B). For PGSA, the C=C bonds of the acrylate have typical resonations at 1125-1225, 1250-1325, and 1700-1750 cm$^{-1}$. The spectra for PGSA were the same as PGS with the addition of an acrylate stretch at 1693 cm$^{-1}$.

Thin film XRD was used to evaluate structural changes of the PGS post acrylation by comparing thermally cured PGS and UV-cured PGSA. Comparison along 2θ revealed intensity differences in peaks at 7.6, 19.5, 32, 37, 39 and 45.5°. At 7.6°, there is no significant difference between the acrylated polymers. However, there is a 0.9 times decrease in the intensity of acrylated vs. nonacrylated PGS at 7.6°. Similarly at 19.5°, there is no significant difference between acrylated polymers but there is a 1.7 times increase of intensity form acrylated to nonacrylated PGS intensities which is significant. At 37°, there is no significant difference between 35 and 40% acrylation. However, there are significant differences between all other samples. Intensity increases from PGS to PGSA 25 by 0.4 times, from PGS to PGSA 30 by 0.8 times, from PGS to PGSA 35 by 2.35 times, and from PGS to PGSA 40 by 2.5 times. At 39°, there are no significant differences between the acrylated PGS but there is a 2.5 times increase from nonacrylated to acrylated PGS. At 45.5°, intensity comparison reveals significant increases from PGS to PGSA 25 of 3.875 times, from PGS to PGSA 30 of 3.375 times, from PGS to PGSA 35 of 6.625 times, from PGS to PGSA 40 of 4.23 times. (FIG. 12).

Glass transition temperatures ($T_g$) were assessed based on the midpoint inflection in the slope on the melt curves for PGS and PGSA with 25, 30, 35, and 40% acrylation. $T_g$ was selected as the critical outcome since it indicates a range for the rubber state of the polymer. DSC results showed PGS had a $T_g$ of −25.7±0.32° C. (mean±SEM) after crosslinking at 120° C. (FIG. 13). PGSA with 25% acrylation had a $T_g$ of −20.1±0.15° C. (mean±SEM). (FIG. 13) PGSA with 30% acrylation had a $T_g$ of −23.2±0.43° C. (mean±SEM). PGSA with 35% acrylation had a $T_g$ of −25.4±0.30° C. (mean±SEM). PGSA with 40% acrylation had a $T_g$ of −26.24±0.43° C. (mean±SEM). (FIG. 13). No significant difference was observed between 0, 35, and 40% acrylations. Significant differences were observed between 25%, 30%, and 0, 35, and 40% acrylations ($p<0.0001$). (FIG. 13).

Mechanical Characterization of Crosslinked PGS and PGSA.

Tensile testing was performed to assess the mechanical properties of thermally crosslinked PGS and UV-crosslinked PGSA with 25, 30, 35, and 40% acrylation. Samples were assessed after crosslinking and after treatment for removal of unreacted agents. The elastic modulus of PGSA 25% was statistically significant with means 2 times greater than that of PGS. (FIG. 14). The elastic moduli of PGSA with 30 and 35 acrylation had no significant difference from one another ($p<0.05$) but were 6 and 3 times greater than PGS and PGSA with 25% acrylation, respectively. A significant difference was observed between the 0 and 25% acrylation group, the 30 and 35% acrylation group and the 40% acrylation group ($p<0.05$). (FIG. 14). PGS was capable of stretching up to an average of 5 cm prior to breaking. (FIG. 15). There was a significant difference ($p<0.0001$) between the extension of PGS and PGSA 25%, with PGS stretching 3.4 times longer than that of PGSA 25% acrylation. (FIG. 15). There was no significant difference in elongation to break between 30, 35, and 40% acrylated PGSA. PGSA 25% stretched 1.5 times further than 30, 35, and 40% acrylated PGSA but the difference was not statistically significant ($p<0.05$). (FIG. 15). PGS samples supported a maximum load of 1.4 N on average. (FIG. 16). In comparison, the max load of PGS was 4.2 times greater than 25 and 30% acrylated PGSA. There was no significant difference between the max loads of 25 and 30% acrylation ($p<0.05$). (FIG. 16). There was no significant difference between the max loads of 35 and 40% acrylation. PGSA 25, 35 and 40% acrylation had max loads which were 1.2 times greater than 30% PGSA. (FIG. 16)

Samples treated for removal of unreacted agents were assessed after 3-1 hour washes of ethanol, followed by 3-1 hour washes of PBS per published protocol referred to as treatment 1 (T1). Tensile testing assessed the UV-crosslinked PGSA with 25, 30, 35, and 40% acrylation. There were significant increases in elastic moduli with increasing acrylation for all samples ($p<0.05$). The elastic moduli of 30% acrylation was 6.4 times greater than 25% acrylation. The elastic moduli of 35% acrylation was 1.3 times greater than 30% acrylation. The elastic moduli of 40% acrylation was 1.6 times greater than 35% acrylation. (FIG. 14). Extension at break decreased with increasing acrylation for all samples. The extension was 2.4 times less for 30% acrylation than for 25% acrylation and demonstrated statistical significance (p<0.05). The extension for 35% acrylation was 1.72 times less than for 0 and 30% acrylation and the difference was statistically significant (p<0.05). The extension for 40% was 1.1 times less than for 35% acrylation but the difference was not statistically significant. (FIG. 15). For tensile strength, PGS (0% acrylation) was statistically significantly different (p<0.05) from all acrylations of PGSA. There was no significant difference (p<0.0001) between tensile strengths for 25, 30, and the 35 and 40% acrylation group. (FIG. 16).

Crosslinked PGS and PGSA polymers were mechanically tested after cleaning with treatment 2 (T2), which consisted of gradated ethanol washes to remove unreacted reagents. Treatment 2 demonstrated a significant increase in stiffness compared to T1. Compared to untreated materials, PGS post-T2 had no significant difference; whereas PGSA was significantly stiffer after T2 than untreated with lower acrylations and became increasingly elastic with increased acrylation following treatment 2. (FIG. 14). For elongation to break, there was no significant difference between the PGS samples, regardless of treatment. PGSA samples demonstrated increased elongation to break for lower acrylations which decreased with increasing acrylation for T1. However, there was no significant difference in elongation to break when comparing untreated and T2 PGSA samples. (FIG. 15). Tensile strength evaluation showed no significant difference for untreated vs T2. There was a significant decrease in tensile strength for T1, compared to untreated and T2. For PGSA, 25% acrylated polymer with T2 was significantly higher than T1 and T2. However, there was no significant difference between 35% and 40% PGSA, following T2 or no treatment. (FIG. 16).

It is to be noted that based on T1 results, 35 and 40% acrylated PGSA indicated satisfaction of the target mechanical properties. Following treatment 2, target mechanical properties were satisfied by only 40% acrylated PGSA. Further, since increased tensile strength was desirable, 40% acrylated PGSA with T2 has been selected as the optimal polymer and treatment for this application.

Degradation properties were evaluated based on mass remaining and swelling properties by weighing samples and measuring sample diameters for 20 weeks. There was no significant difference in degradation between the different acrylations for mass remaining Mass remaining dropped to 96% over the first 24 hours, and then decreased linearly at 0.32% per day for 14 weeks. After 14 weeks, the remaining mass stabilized at 70% throughout the rest of the 20 weeks. (FIG. 17). The swelling data only demonstrated a significant difference between 25% and the higher acrylations. During the first 24 hours, there was an average of a 12% decrease in diameter across samples. After the first day, 25% maintained a linear increase in swelling of 0.46% per day up to 11 weeks followed by a slower increase of 0.17% per day until week 16 and a further slowed increase in swelling of 0.11% per day til the end of the 20 week study. For the higher acrylations, swelling increased at 0.18% per day up to 11 weeks to stabilize at ~100% for the remainder of the 20 weeks. (FIG. 18).

Cellular Compatibility.

BCA protein assays were performed using HEPM and B35 cell lines. For HEPM cell lines, there was no significant difference between 35 and 40% PGSA. There were significant differences between the non-plated cells and the plated cells. There was a 1.96 times increase in protein from non-plated controls to plated controls, a 1.52 times increase in protein from non-plated controls to cells on 35% PGSA, and a 1.32 times increase in protein from non-plated controls to cells on 40% PGSA. There was also a significant difference between plated cells and PGSA. The protein decreased by 15% from plated cells to 35% acrylated PGS and decreased by 22% from plated cells to 40% acrylated PGS. (FIG. 19). For B35 cell lines, there was no significant difference between 35 and 40% PGSA. There were significant differences between non-plated and plated cells. There was a 5.6 times increase in protein from non-plated controls to plated controls, a 2.78 times increase in protein from non-plated controls to cells on 35% PGSA, and a 2.58 times increase in protein from non-plated controls to cells on 40% PGSA. There was also a significant difference between plated cells and PGSA. The protein decreased by 43% from plated cells to 35% acrylated PGS and decreased by 46% from plated cells to 40% acrylated PGS. (FIG. 20).

Electrical Conductivity.

When 35% PGSA polymer is doped with soluble PPy, it was found that the conductivity of the PGSA increased in a non-linear fashion as the percentage of PPy dopant was increased. (FIG. 21). Electrical conductivity data were performed on PGSA 35 doped with 0, 0.001, 0.005, and 0.05% soluble PPy. There was a significant difference between all samples, p<0.001, α=0.05. PGSA 35 with 0.001% PPy's conductivity was 5.4 times greater than undoped PGSA 35. The conductivity for PGSA 35 doped with 0.005% PPy was 2.5 times greater than that of PGSA 35 with 0.001% PPy and 13.5 times greater than undoped PGSA 35. The conductivity of PGSA 35 doped with 0.05% PPy was 1.23 times greater than that of PGSA 35 with 0.005% PPy, 3.07 times greater than that of PGSA 35 with 0.001% PPy, and 16.56 times greater than undoped PGSA.

In Vitro Cellular Stimulation Via Biphasic Sheets.

Figure 9:
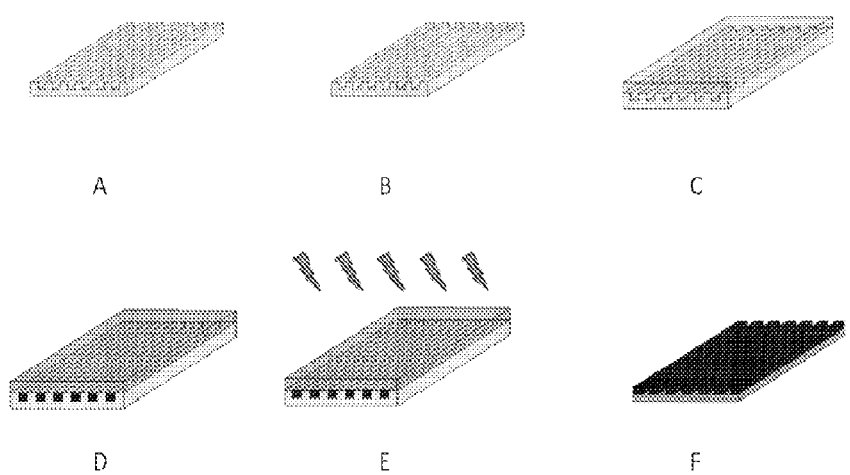
FIG. 9 schematically illustrates the preparation of a biphasic sheet. Preparation of a sheet mold involves (A) providing a Delrin inverse mold with spacings 600 μm wide and 400 μm deep; (B-C) using Sylgard 184 Silicone Elastomer Kit (Dow Corning, Midland, Md.), with silicone molds cast using the Delrin mold to obtain thin flexible sheets with the desired spacings which could be used to create tubular molds in the future; (D) providing low conductivity polymer into the valleys of the mold and having a top coated with high conductivity polymer; (E) crosslinking the sheets for 20 minutes under 365 nm, 30 W/cm2 UV irradiation; and (F) obtaining the final biphasic sheet.
Figure 10A:
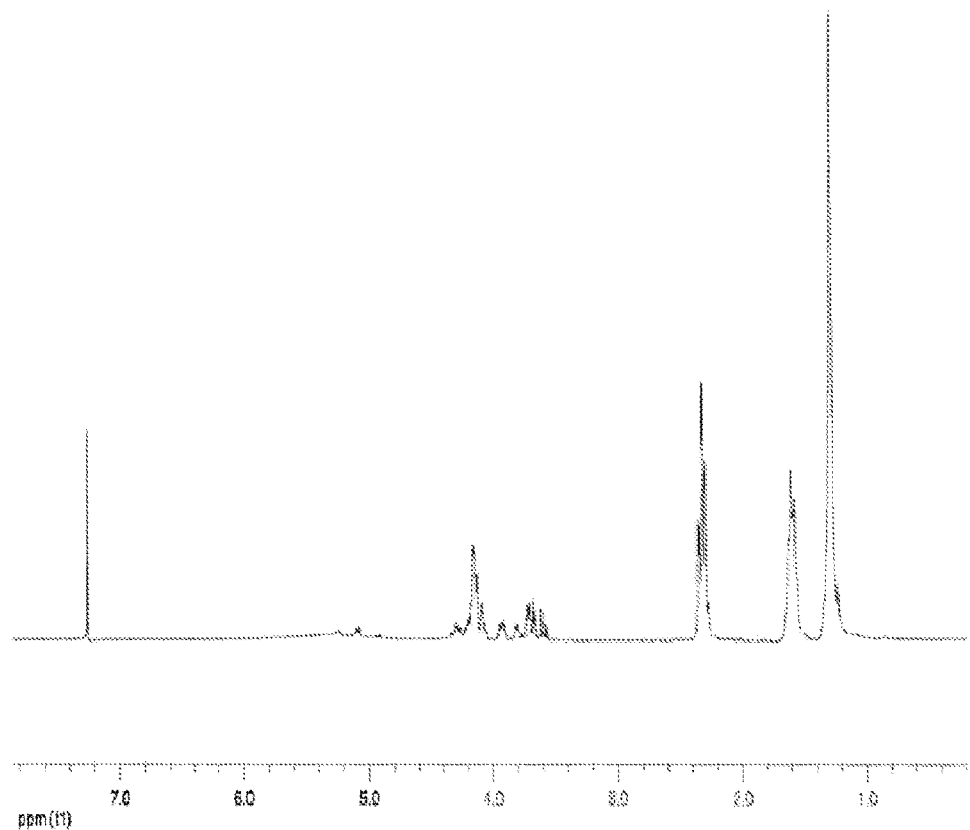
Figure 10B:
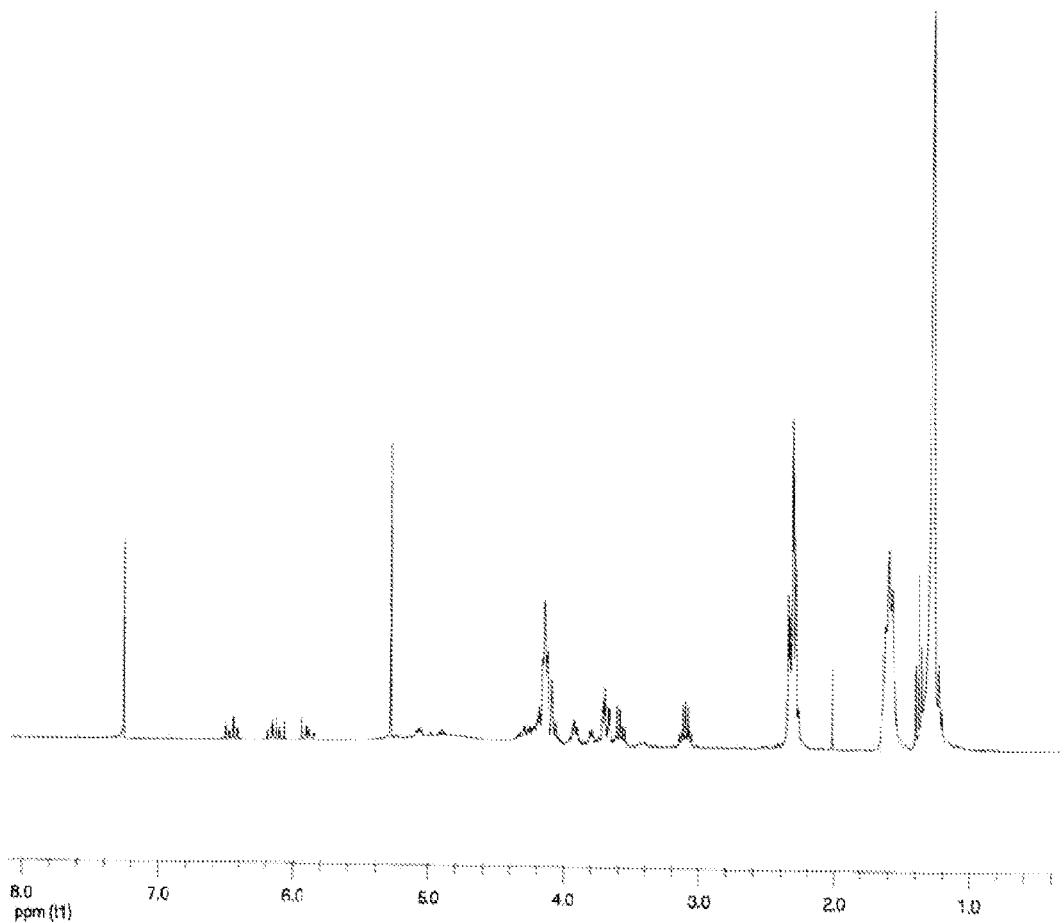
Figure 10C:
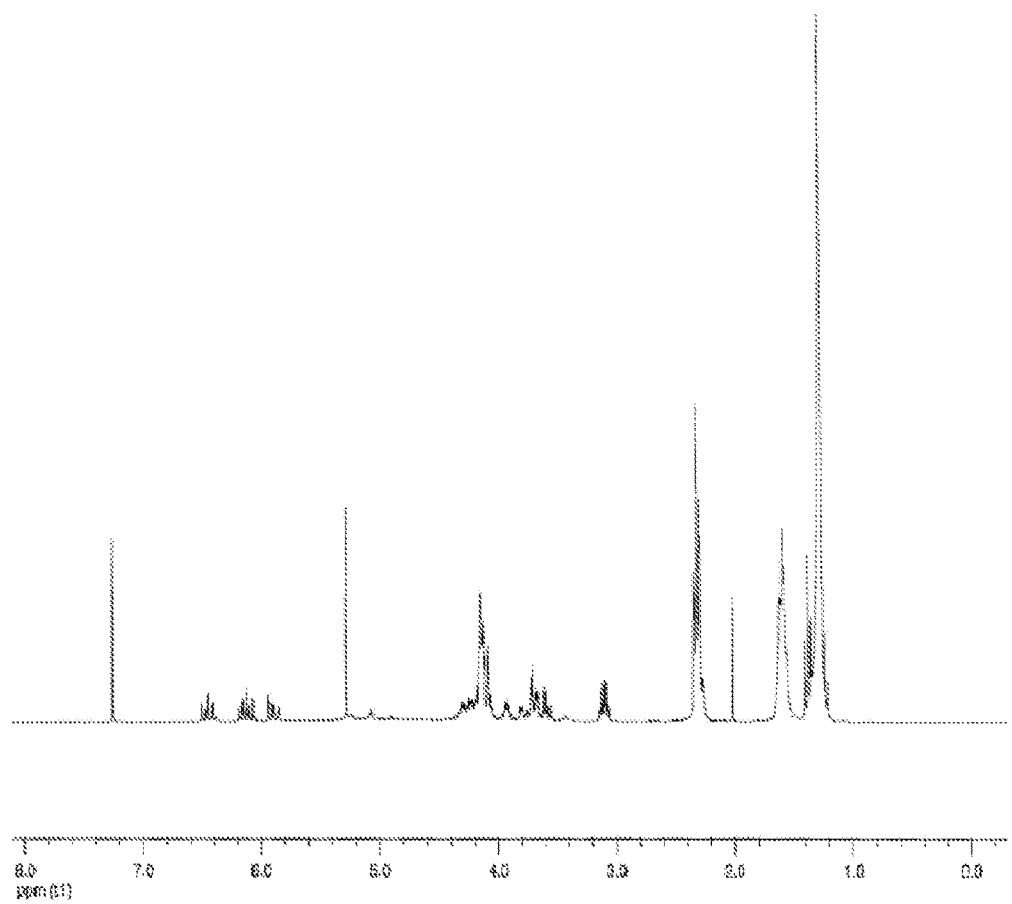
Figure 10D:
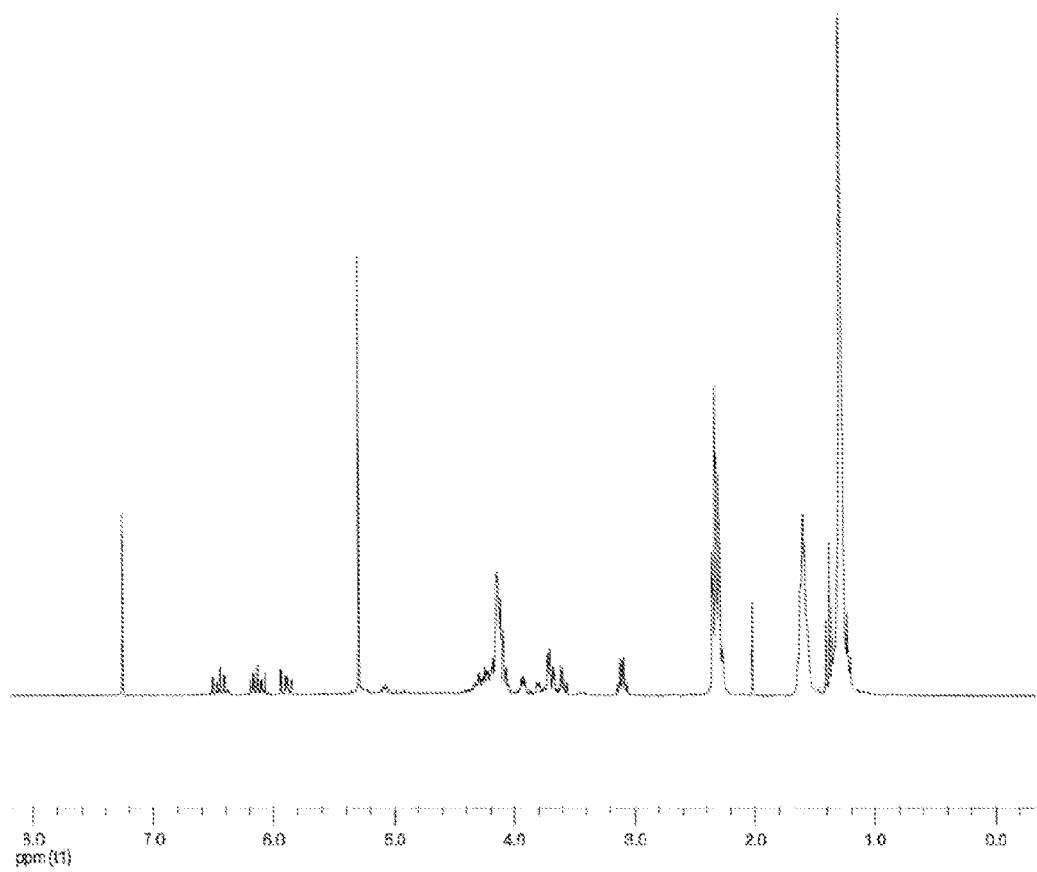
Figure 10E:
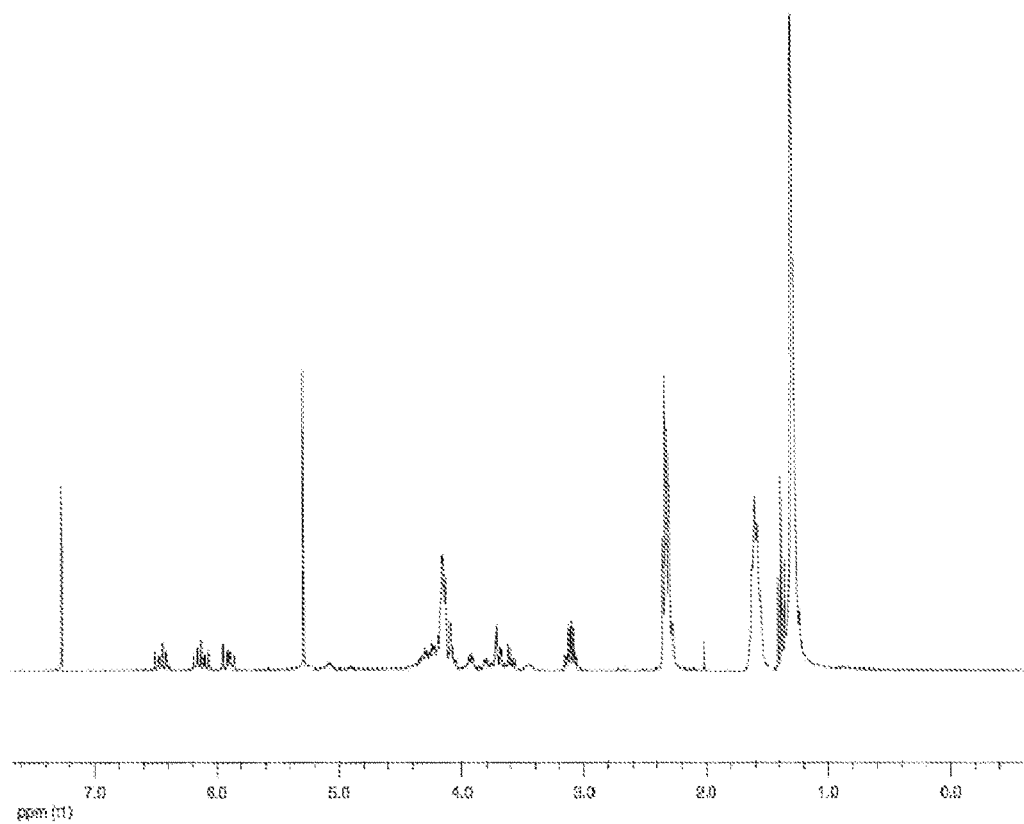

Using the procedure outlined in FIG. 9, biphasic sheets were prepared. Two treatment types were applied prior to cell studies. For the first treatment, polymers were treated three times with 1 hour of 70% EtOH, followed by three, one hour rinses of PBS. For the second treatment, polymers were treated using 15 minute rinses of EtOH solutions gradated up from 30, 40, 50, and 60% to 50%, 30%, and three rinses of PBS. Cellular growth was compared over time on the polymers with both treatments types and with either no stimulation, 1 day of stimulation, or 3 days of stimulation at 3 V, 20 Hz through the biphasic sheets. (FIG. 22).

Formation of Biphasic Tube.

Using the developed materials and the method shown in FIG. 4, the tube was prepared as indicated having, in cross section, the continuous hole through the tube. (FIGS. 23A and B). Additionally, in transverse view, the separate phases or segments of the tube were depicted (FIG. 23B). The tube shown was 5 inches long and suitable for cutting to fit a specific patient's needs. For implantation, the proximal end of the nerve was sutured into one end and the distal end was sutured into the opposite end. A silver wire loop was affixed to each end to connect to wires from an electrical stimulator. The distal end was grounded and the proximal end was supplied with a square wave with 3 V, 20 Hz.

Discussion

Validation of PGSA Material Properties.

In this approach, the goal is to mimic the mechanical properties of tissue surrounding the nerve while repeating observed electric fields near the wound site to promote neurite outgrowth. Present nerve guides comprised of PLGA, collagens, or PVA fall short of native nerve's mechanical properties either due to insufficient elasticity or loss of mechanical properties due to early degradation. Based on mechanical and degradative property matching to native nerve tissue, PGSA was selected as an alternative to presently marketed nerve guide materials. NMR and ATR-FTIR were used to characterize the PGS and PGSA and were used to confirm the specified 0, 25, 30, 35, and 40% acrylations of PGSA. Significant changes in mechanical properties were observed between polymers before and after treatment for cell culture, as well as [between treatment conditions for cell culture]. The factor of two decrease in tensile strength coupled with the decrease in elastic modulus contributed to an increase in elongation to break post treatment. These data suggested that treatment 1 damaged the acrylated polymer crosslinks, such that, removal of stiff strengthening bonds enabled increased flexibility and decreased polymer strength. Distinction of damaged polymeric bonds was unable to be made via XRD due to wide d-spacing ranges for 2θ peaks. Glass transition temperatures decreased 1 to 2° C. per 5% acrylation but did not distinguish between higher acrylations (35 and 40%). Degradation data demonstrated that the mass and swelling did not differ with respect to extent of acrylation. Further, as the polymer lost mass, samples continued to swell. This indicated that degradation occurred due to a combined effect of surface erosion and swelling, which is in contrast to previous work which suggested only surface erosion.

Cellular Interactions with PGSA and PGSA/PPy Composites.

To promote neurite outgrowth, it was crucial to evaluate cellular growth on the developed materials in terms of attachment, alignment, and potential for molecular gradients. For some polymers, neuron growth/attachment has been limited or prevented due to the absence of added attachment proteins (e.g. fibronectin, fibrin, laminin, collagen, thrombin, heparin, poly-L lactide, and factor XIII) and/or peptides (e.g. IKVAV and RGD). Using the BCA assay, both fibroblasts (HEPM) and neuronal (B35) cells demonstrated the ability to attach to PGSA with additional attachment proteins or peptides.

In addition to protein attachment, micro- and nano-textured patterns have been utilized as an aid for cellular alignment. In seeming contrast, the ridges in this study were perpendicular to the desired direction of nerve outgrowth to alternate polymer phases. While alignment with cells has been facilitated using topography, linear cell growth has chiefly occurred due to synergistic effects of Schwann cells and/or attached surface proteins. Further, neurites have demonstrated bridging across micropatterned grooves. We observed the neurites appear to extend through the soft material to cells in neighboring valleys, indicating dominance of the charged surfaces influencing directionality more than topography. This observation is in agreement with previous work which demonstrated that electric fields of physiological strength tend to dominate and override other directional cues. Topography did not demonstrate a restriction to cell extension in this study.

Multimolecular gradients of growth factors (nerve growth factor (NGF), glial derived neurotrophic factor (GDNF), brain derived neurotrophic factor (BDNF), N-cadherin, ciliary neurotrophic factor (CTNF), and fibroblast growth factor (FGF)) have been evaluated for nerve guidance and repair from either surface binding or encapsulation for delayed release. The slow swelling nature observed for the PGSA materials demonstrated potential for a simple method for gradient growth factor release from within the conduit construct. Regions of the conduit containing PPy for high conductivity may be used to simultaneously release growth factors, creating repeated gradients of growth factors along the path for neurite outgrowth. Together these observations indicated that PGSA alone demonstrated good cellular adhesion, potential for simple gradient growth factor release and charged substrates enabling directed neurite growth independently of topography.

Electrical Stimulation.

The biphasic structure of the sheets in this study was designed to create repeated electric field gradients by alternating high and low electrically conductive materials connected to an external electrical stimulator. Previous studies have demonstrated chemically enhanced and decreased currents have created biologically significant linear cell migration responses in vivo. Additionally, electrical stimulation from the proximal to distal ends of transected nerves has demonstrated promise. To isolate effectors, adhesive properties and substrate materials have been shown to effect cellular response to electric fields in vitro. Net surface charge has been shown to play a key role in response.

Additionally, using treatment 1, evident surface cracks were observed at 20× magnification, resulting in uneven imaging surfaces and subsequent imaging challenges. Cell growth was not hindered and cells demonstrated increased growth and migration across the high conductivity materials toward low conductivity material with increased stimulation time.

Conclusions.

The purpose of this study was to develop a bioresorbable tube capable of producing repeated electric field gradients with an applied stimulus to be used for assessment of nerve outgrowth. The concept is that application of a voltage drop across a biphasic tube comprised of alternating high and low conductivity polymers (in approximately 600 μm segments) would generate repeated electric fields within the tube to enhance nerve growth through the tube. The devices disclosed comprising PGSA demonstrated the targeted mechanical and electrical properties necessary and needed for nerve repair. Indeed to overcome key limitations of present FDA approved guidance conduits (early degradation, rapid loss of mechanical properties, and increasing stiffness causing nerve compression), PGSA was selected as the base material due to its target strength, flexibility, and degradation performance with a 20 minute crosslinking time. Indeed, rapid crosslinking time was expected to simplify the preparation of a biphasic structure. Moreover, cell growth was demonstrated on the polymeric materials. Results demonstrated 40% acrylated PGSA satisfied target mechanical properties. Moreover, undoped PGSA met requirements for low conductivity and 0.05% PPy in PGSA met the high conductivity parameters. Finally, conduits were prepared using the designed materials and were composed of high and low conductivity materials.

Example 3

Prospective Development and Evaluation of an Additional Segmented Conduction Conduit Results from one hour of AC electrical stimulation of nerves proximal to the site of injury demonstrate axon regeneration rate increase over three times compared to the untreated rate of regeneration. The observation in the axon extension process following electrical stimulation is a decreased delay time for axon elongation and increased axon sprouts. These repair actions over a limited time range motivate evaluation of extended stimulation. However, extended stimulation time yielded no improvement. Reflection on newt limb and bovine corneal studies implies that the limiting factor may be distance of effectiveness of single point electrical stimulation (measured as 600 μm), rather than time length of stimulation. This observation provides further biological support for incremental electrical field stimulation. To answer the question: "Is the critical gap size for nerve repair limited by the lack of incremental electrical simulation points?", a segmented electrical backbone may be created to enable repeated stimulation along a conduit for axon repair.

Identification of desired mechanical and electrical parameters is necessary prior to construction a segmented electrical conduit. Experimental data from fresh rat sciatic nerve measured natural mechanical properties of Young's modulus between 0.4-0.7 mPa and tensile strength between 1.1-1.7 mPa. Peripheral nerve repair in human patients occurs over a three month to one year time span. Further, the stipulation of incremental electrical stimulation can be satisfied with alternated high and low electrically conductive materials. FIGS. 3A and 3B illustrate high conductive materials with lengths of 600 μm based on the measured effective distance of electric field gradients and low conductive material lengths of 10-40 μm based on the size of inducing epithelial cell bodies.

The maximum conductivity required is calculated using Ohm's law and experimental data. Ohm's law states $J=\sigma E$, where $J$=current density, $\sigma$=conductivity of the medium/material, and $E$=the electric field. Using experimental average values for the current density and electric field, $J=50$ μA/cm$^2$ and $E=40$ mV/mm. Thus, upon rearrangement of Ohm's law and calculation, the target conductivity for the higher conductivity material is $1.25\times10^{-4}$ S/cm. The boundary for the lower conductivity needs to be significantly less than the high conductivity while minimizing resistance (to limit hearing due to high resistance). The target for the lower conductivity material is ten times less than the high conductivity, $1.25\times10^{-5}$ S/cm. Additionally, the property has a degradation rate on the order of about 3-12 months. Together the mechanical, degradative, and conductive properties identified provide the parameters for development of the segmented conducting conduit.

Since mechanical and degradative properties are essential to the support structure of the final device, the first step in conduit development is to tailor the basic material properties. Criteria for degradation (3-12 months) and low conductivity material are essential to materials selection. Inspection of FIG. 2 indicates that no individual polymer meets the desired material parameters outright. As a result, mechanical properties will be tailored by varying the ratios of multiple polymers to form a composite which fits the criteria. PCL, PEUU, and poly(caprolactone) fumarate (PCLF) may meet the degradative qualifications. PCL is readily available off-the-shelf, whereas PEUU and PCLF require synthesis and characterization processes. To achieve the degradation goal using the simplest material process possible, PCL will be applied as a component of the composite material. While PCL has desirable degradative properties, the tensile strength and elastic modulus are much higher than the desired material parameters for nerve repair. Incorporating a biodegradable elastomer such as poly(1,8-octanediol) citrate (POC) or PGS would decrease both the elastic modulus and tensile strength. PGS will be included rather than POC since PGS has demonstrated positive cellular response while POC's acidity has resulted in cell toxicity. Among the options for conductive polymers found in FIG. 2, chitosan stands out as the only natural polymer with conductivity in the range indicated for low conductivity material. Since the synthetic conducting polymers have demonstrated cell compatibility issues, minimal incorporation is desirable. Combination of PCL, PGS, and chitosan may contribute the degradative, mechanical, and conductive properties needed to meet the material specifications.

Following materials selection, the next step is polymer synthesis. While chitosan and PCL are available from Fisher, PGS is not available off-the-shelf. PGS prepolymer is formed by melting sebacic acid under nitrogen and adding glycerol dropwise to the solution. (See FIG. 24). Following 4 hours of heating under vacuum pressure, PGS prepolymer will be ready to be crosslinked (See FIG. 24). PGS will be partially crosslinked in a vacuum oven at 20 psi and 150° C. but crosslinkage will be stopped at 13 hours just before PGS can no longer be manipulated. The partial crosslinking process will decreased required crosslinking time after polymer blending while maintaining PGS in a liquid form suitable for incorporating polymer solutions. PGS may be characterized using gel permeation chromatography (GPC) to measure the molecular weights and reaction efficiency, Fourier transform infrared spectroscopy (FTIR) to observe peaks at 1747 cm$^{-1}$, 2686 cm$^{-1}$, and 3461 cm$^{-1}$ (from ester carbonyl, hydroxyl groups in carboxyl, and ester formation, respectively) which are not present in the monomers, and DSC to determine the melting points and glass transition temperatures.

To prepare samples for mechanical and degradative evaluation, PCL (80,000 kDa Fisher) and chitosan (low molecular weight, 50-90 kDa, from Sigma with 96% deacetylation) will be dissolved in glacial acetic acid. The PCL and chitosan solutions will then be stirred together and added dropwise to a melted solution of partially crosslinked PGS, while stirring. (See FIG. 25). The PGS/PCL/chitosan solution will be doped with 75 weight % NaCl crystals to generate pores between 10-60 μm in the final material, which will enable nutrient diffusion but prevent fibroblast and macrophage intrusion. The doped PGS/PCL/chitosan solution will be poured into a glass dish to create a sheet 0.3-0.7 mm thick. The solution will be set in a chemical hood overnight to allow evaporation of acetic acid. The chitosan will be crosslinked via a UV lamp exposure for 10-15 minutes. PCL and PGS will be crosslinked by placing the solution in a vacuum oven at 120° C. for 3-4 hours.

Following crosslinking, samples will be cut into dog bone samples using ASTM D-638-IV. The material will be soaked 1-2 days in PBS (pH 7.4) prior to mechanical testing. This is expected to demonstrate minimal swelling and to leach out NaCl or sugar crystals having porous scaffolds. Mechanical testing will be performed using an Instron mechanical tester to evaluate the elastic modulus and tensile strength. If mechanical properties are outside the ranges set forth above, concentrations of PGS, PCL, and chitosan will be adjusted to achieve properties within the range. Since a 7:3 ratio of PCL:chitosan has previously achieved tensile strength in the optimum range, it is expected that an appropriate ratio will be approximately 1:6:3 or 1.5:6:2.5 for PGS:PCL:chitosan. Additionally, samples will be soaked for two weeks in PBS (pH 7.4) and evaluated for mechanical properties to confirm no change in mechanical properties over time. Preparation of three lots with ten samples per lot will be used to confirm mechanical and degradative properties. Each lot will be halved to yield 5 samples for pre-soak and 5 samples for evaluation after two weeks of degradation. The experiment may be outlined in a series of steps: (1) Material/solution preparation; (2) sheet polymerization procuring 3 samples; and (3) mechanical testing (for pre-soak and two week degradation) utilizing 5 pre-soak samples and 5 degradation samples. In total, there would be approximately 30 samples (10×3=30 samples). The expected outcome of the aforementioned method would be to achieve material properties in a sheet form corresponding to target mechanical properties as set forth above.

Preparation of segmented conductive sheets will be prepared to demonstrate proof-of-concept for the segmented conducting tubular scaffolds, since sheets are easier to make initially. The experiment may be outlined in a series of steps: (1) prepare gold nanorods; (2) prepare high and low conductivity solutions; (3) prepare a two step synthesis of conducting segmented sheets to procure 3 samples; and (4) evaluate mechanical and conductive properties (for pre-soak and two week degradation) utilizing 5 pre-soak and 5 degradation samples. In total, there would be approximately 30 samples (10×3=30 samples). The expected outcome of the aforementioned method would be to create segmented conducting sheets with conduction with capacity to produce electric fields between about 20-60 mV/mm. The first step of this experiment is to generate high and low conductivity materials for the two segment types. The material developed in the first experiment will be used as the low conductivity solution. High conductivity solutions will be produced by doping a small volume of low conductivity solution with 0.5-3% of either PPy (Wako Pure Chemical Industries, Ltd.) or gold nanorods (synthesis required). Dispersion of gold nanorods within polymers will be confirmed via transmission electron microscopy (TEM).

Gold nanorod production begins with synthesizing seeds which are added to three steps of growth solutions to extend the spherical seeds into long, thin rods (FIGS. 26A and 26B). Growth of the particles between steps is indicated by color changes, which can be evaluated using a spectrophotometer. After 16 hours of ageing, rods are purified by removal of the supernatant, followed by washing with deionized water and centrifugation to remove excess stabilizing agents (FIG. 26C). Conductivity is maximized for rods with maximal length and minimal diameter. Gold nanorods will be prepared using cetyltrimethylammonium bromide (CTAB, Fisher) stabilized 5.6±0.6 nm diameter seeds to maximize average nanorod lengths (564±63 nm) and aspect ratios (length divided by diameter of rod, 22.6±2.4), while minimizing the distribution of aspect ratios.

Assembly of segmented conducting sheets will occur after high and low conductivity solutions are produced. Using a rectangular glass mold (FIG. 27) with a vertical grid insert (to create openings for the short segments), the high conductivity solution will be poured into the mold for a 0.3-0.7 mm depth. The chitosan will be UV crosslinked for 10-15 minutes followed by crosslinking for 1-1.5 hours at 120° C. under vacuum to allow the polymer to stabilize in structure without complete crosslinking. Following partial polymerization, the vertical grid insert will be removed and low conductivity solution will be injected into the spaces created by the grid. PCL and PGS will be crosslinked by placing the solution in a vacuum oven at 120° C. for 3-4 hours to complete polymerization. Degree of crosslinking will be assessed for by DSC for high and low conductivity solutions and the polymerized sheet. Comparison of crosslinking extent for solutions versus the sheet will serve as an indicator for varying the heat exposure time.

Evaluation of segmented conducting sheets includes mechanical and electrical evaluation before and after degradation. As performed in the first experiment above, scaffolds will be soaked 1-2 days for hydration and removal of crystals to establish a porous structure. Following initial soaking, scaffolds will be removed from molds and cut into dog bone shaped samples using an ASTM D-638-IV stamp. Samples will be evaluated using an Instron mechanical tester to assess elastic moduli and tensile strengths. Mechanical changes following degradation will be evaluated following sample soaking for two weeks in phosphate buffered saline. Particular attention to fracture under tension along interfaces between high and low conductivity will be noted. If interfaces result in lines of fracture in greater than 30% of samples, a thin (0.5 mm) layer of PCL with 75 weight % of salt or sugar crystals will be added to the top of the structure following partial crosslinking of the high conductivity material. The modified sheet will be heat crosslinked to provide a stable reinforcement layer in future structures. Mechanical properties will be verified by reproducing three sheets of polymers with no significant difference in responses before and after short term degradation.

After stabilizing the mechanical structure, electrical properties will be evaluated after the 1-2 days pre-soak and two weeks degradation in PBS. Conductivity of polymer segments will be evaluated using an electrodiagnostics device to measure impedance. A traditional multimeter is not necessarily an option due to the low values of conductivity to be measured. To measure the conduction rates, two oscilloscopes (for multiple outputs) will be connected to an iox1 data acquisition system (DAQ). A power supply (also connected to the DAQ) will be used to apply a 0.1-0.2 ms, 3 V stimulation to one end of the conducting sheet. Contacts for attaching oscilloscope leads will be inserted with the aid of a light microscope for placement of probes into the small high conducting segments prior to final polymerization. Following polymerization, the material will be stimulated from one end of a sheet or conduit. The DAQ will acquire the stimulation time (pulse distance) and amplitude (voltage), as well as, the electrical response of the material with accompanying time from the power supply and oscilloscopes. Data will be exported to a PC (or other computer) for analysis of conduction rate between segments. Imaging of the probe inserts via the light microscope will enable the distance between the points of recorded outputs to be measured. Electrical properties will be statistically verified by reproducing three sheets of polymers with no significant difference in responses before and after short term degradation. The electrical conductivities calculated from the literature are without a specified range and are intended to serve as guidelines rather than required outcomes. Conductivities within two orders of magnitude of the stated target will be acceptable with the understanding that there should be at least one order of magnitude difference between high and low conductivities. Based on literature measurements from newt studies, the flexible electric field strength range is between about 20-60 mV/mm Conduits achieving high conductivity in the range of about 20-60 mV/mm with measured millisecond delays between segments will meet conductivity expectations.

Conduits may be formed using an optically transparent glass mold (about 2 mm thickness) constructed as a cylinder within a tube (FIG. 28). The inner cylinder will generate the hollow portion of the conduit. The outer tube will be thin to allow UV transmission for crosslinking the polymers. The outer cylinder diameter will be about 1.5 mm. Since the literature has shown conduits are optimally about 0.3 mm thick for nutrient diffusion, the inner diameter of the outer tube will be about 1.8 mm. The tube mold will be about 2 cm in length inside with one end open for polymer injection and a cap on the base to close the tube. The inner cylinder will attach to the cap on the base with a screw to allow separation of the base from the inner cylinder. High and low conductivity polymer solutions will be alternatively injected and partially crosslinked for 15-20 minutes. This will allow the polymers to have strong bonding at polymer interfaces while maintaining distinctly high and low conductivity segments. Use of two syringe pumps will allow controlled injected quantities without having to switch syringes between injections. Additionally, the syringe pump precision enables mall quantities to be injected to meet a 20-40 µm spacing parameter for the high conductivity segments. Following injections, the entire conduit will be UV crosslinked an additional 15-30 minutes. Based on results from the second experiment set forth above, if interfaces between segments demonstrate mechanical weakness, the external surface of the tube will be roll coated with about a 0.5 mm layer of PCLF with 75 weight % crystals for porosity. The outer layer will be crosslinked with 8-10 minutes. Crosslink times are based on times used for PCLF crosslinking in a glass mold or uncovered. Crosslink percentage will be evaluated using a DSC to confirm the suitability of crosslinking time.

Post construction, the conduits will be evaluated in the same manner as for the previously constructed sheets. Using a light microscope to identify the high conductivity segments, impedance will be measured using an electrodiagnostic device. Conduction rates will be assessed using oscilloscope measurements as previous described. Mechanical properties will be characterized using the Instron mechanical tester for samples before and after short term degradation in PBS as previously described. Samples undamaged by testing techniques will be used for multiple tests. For example, conduction and conductivity rate assessments will be performed on the same samples. Insertion of probes for conduction may affect mechanical testing results so separate samples will be prepared without dyes and probes. Approximately three conduits will be evaluated for each experiment. The third experiment may be outlined as follows: (1) preparation of materials and solutions; (2) multistep synthesis of segmented conducting conduits; (3) evaluation of mechanical and conductive properties for pre-soak and two week degradation utilizing six pre-soak samples and 6 degradation samples. The expected outcome of the foregoing study is to establish a consistent protocol for segmented conduit preparation, using 12 samples, with materials which meet the mechanical and conductive ranges necessary as set forth above. This third experiment will demonstrate feasibility of conduit construction and confirm that the generated conduits meet and maintain mechanical and conductive properties.

In conclusion, the aim is to create repeated electric field gradients, segmented conducting conduits that will be developed and evaluated based on mechanical and electrical properties. Specifically, PGS/PCL/chitosan will be formed into flat sheets to tailor mechanical and degradative properties. Moreover, either PPy or gold nanorods will be used to dope polymer materials to create high and low conducting materials. Sheet materials comprised of repeated biphasic conducting materials will be assessed then for mechanical and electrical properties. Additionally, compositions of high and low conducting materials will be used to create repeated biphasic conducting conduits which will be mechanically and electrically tested as nerve conduits.

Example 4

Prospective Evaluation of Cell Response and Stimulated Growth Response Relative to Segment Spacing and Stimulus Time.

In vitro studies enable new devices to be evaluated using established cell culture and relevant outcome measures prior to using animal models. Since neurons and Schwann cells comprise the key cells in the peripheral nervous system, evaluation of their response to the construct and stimulation constraint as a guideline for in vivo work is key. Macro level cellular responses such as cellular attachment, cellular activity, and neurite extension rates will give insight to the overall response to the material and the applied electrical stimulus. Using in vitro studies, influences of voltage types, stimulation patterns, and spacing between peak conductivity on neurite outgrowth will be evaluated.

Further optimization of conduit parameters can be assessed by connecting select in vitro results to the electrical stimulation via mathematical modeling. The segmented conducting model resembles the structure of internodes and nodes of Ranvier in myelinated nerve. The nodes of Ranvier may be modeled with accompanying internodes using a multi-compartment model to represent nodes with capacitors and leakage currents from resistors in parallel with internodes composed of parallel capacitors and resistors. Physiologically, the nodes change ionic concentration in response to stimulation from action potentials. Since properties assumed by resistors and capacitors are valid for static rather than active devices, use of basic circuit components are inappropriate for modeling the nodes. Further, the fact that the nodes and internodes are hollow casings around the axon causes their basic physical parameters to be violated. While the conducting segmented conduit is not an active device (subject to ionic and protein changes), the physical parameters prevent use of a simplified electronics based model. To assess the effect of stimulation on the in vitro outcomes, the electric field at any given point could be calculated and compared for its effect on select in vitro outcomes. The electric field calculation is nontrivial but can be accomplished through the use of Maxwell's equations with appropriate boundary conditions selected. The resulting electric field at a selected point will be compared to in vitro outcomes to correlate the effects of electrical stimulation with in vitro responses.

In vitro Conduit Assessment. Experiment 1:

Although PGS, PCL, chitosan, gold nanorods and low fractions of PPy have previously demonstrated (separately) either positive cell or minimally inhibitory cellular response, the material combination should be evaluated for cellular response prior to further experimentation. Since the main cells of interest in fiber repair are Schwann cells and neurons, conduits will be seeded with both cell types separately and combined on scaffolds. Conduits will be prepared using techniques established above. Using Schwann cell line S42 (ATCC CRL-2942) and primary rat neurons, samples will be divided into groups as demonstrated in FIG. 29. Prior to cell seeding, conduits will be pulsed with 50% ethanol, and flushed overnight with PBS (pH 7.4). Each conduit will have one end capped with a 0.22 µm pore film to prevent injected neurons from drifting out of the tube. Neurons ($5 \times 10^8$ per conduit) will be suspended in saline solution and injected into the conduit from the open end. The open end will be capped by a second 0.22 µm pore film to contain neurons within, prevent Schwann cell entry, and maintain nutrient flow. Neuron filled conduits will be placed singly into individual wells of a 6 well plate and covered with media. Schwann cells will be seeded onto conduits by injecting $5 \times 10^5$ cells per conduit into each well and rocking the plate on a shaker table for four hours while maintained at 5% $CO_2$, 37° C. Seeded conduits will remain in 6 well plates covered in cell culture media, and maintained at 5% $CO_2$, 37° C.

Each conduit will be assessed for cell viability and activity for neurons and Schwann cells at 3 and 5 days after seeding. Accordingly, each conduit will be halved along the horizontal and vertical midsections and assessed as indicated in FIG. 30. Since the thickness and materials of the conduit are expected to result in an opaque material, fluorescent assays have been selected to enable quantification via reflectance spectroscopy. The conduit quarters for Schwann cell evaluation will be placed inverted (that is, the outside of the conduit will be facing up) in a 24 well plate. The conduit quarters for neuron assessment will be placed with the inner conduit portion facing up in a 24 well plate. The TECAN plate reader will be used to quantify the fluorescence via reflectance or transmission spectroscopy, as needed.

To assess cell viability, the live/dead cell assay (Molecular Probes) will be performed on seeded conduits at 3 and 5 days. The live/dead cell assay indicates live cells with green fluorescence (via Calcein AM) cells and dead cells via red fluorescence (through use of Ethidium homodimer-1). Each conduit quarter will be covered by reagents for one hour. After reagent removal, the TECAN plate reader will measure the reflective fluorescence. Samples will be assessed as demonstrated in FIG. 29.

The MTS assay reagent (Promega) produces a purple, water soluble formazan product in the presence of active mitochondrial enzymes. Conduit segments as shown in FIG. 30 will be placed in 24 well plates as shown in FIG. 29 at 3 and 5 days after cell seeding. Media will be removed from conduit quarters and pipette into wells of a 96 well plate to be analyzed with the TECAN plate reader at an absorbance of 490 nm. The experimental conduits with cocultured Schwann cells and neurons will be compared to conduits with only neurons or Schwann cells to observe the expected enhanced activity from coculture and to distinguish contributions of the combined effects from the separate cell type activities. Assessing the conduit with no cells serves as a negative control to indicate the conduit's response to the reagents. Positive controls serve as indicators for substrates with known positive cell responses. Expected results include an additive effect for the cocultured conduits as compared to the single cell type cultures. Comparison of the controls to coculture seeded conduits should indicate if there is a negative material response or needed adjustment for culture conditions. Significant decrease in intensity (cellular activity) will indicate a potentially cytotoxic response or the need to modify culture conditions. To maintain in vitro cultures, it may be necessary to absorb laminin to the surface of the conduit.

Experiment 2:

After confirming positive cellular response to the materials, stimulation type will be assessed. Successful stimulation results have been demonstrated using 3 V, 20 Hz AC stimulation proximal to the site of injury. However, the stimulation parameters used correspond to functional myelinated motor fiber signalling rather than physiological properties found in regenerative nerve repair (DC electric field of peak 40 mV/mm). Conduits will be seeded (inside with neurons, outside with Schwann cells) 24 hours prior to stimulation to allow cellular attachment. To compare the effect for the AC vs. DC stimulation parameters on neurite outgrowth, seeded conduits will be stimulated for 1 hour using groups as demonstrated in FIG. 31.

Stimulation will be applied with a positive lead on one end of the conduit and a negative lead for grounding the other end of the conduit. Conduits will be housed in six well plates and completely covered in media. Neurite outgrowth will be measured via reflective fluorescence microscopy following calcein AM staining after 24 hours and 48 hours of stimulation. AC and DC stimulation will be performed in triplicate. The data will be statistically compared using the t-test. A biologically significant difference in neurite outgrowth will determine the type of stimulation to be used for future experiments. Comparison of neurite outgrowth form three locations per scaffold will reveal if there are differences between the effects utilizing AC vs. DC stimulation parameters on axonal outgrowth. Stimulation that induces maximal neurite outgrowth will be the future mode of stimulation.

Experiment 3:

After resolving the mode of stimulation, the time of stimulation must be optimized. Conduits will be seeded (inside with neurons, outside with Schwann cells) 24 hours prior to stimulation to allow cellular attachment. Using AC or DC stimulation as determined by Experiment 2, conduits will be stimulated as per the methodology outlined in FIG. 32. Initially, one sample from each group will be tested at a time. If samples indicate that overstimulation induces apoptosis or inhibits neurite outgrowth, patterns will be modified to reduce stimulation frequency. Final samples will be replicated in triplicate. Data will be statistically compared using a one way ANOVA with Kruskal Wallis post hoc assessment. A data comparison will demonstrate if there is a difference in the influence of stimulation patterns on neurite outgrowth. The optimal stimulation pattern will be selected based on which method produces maximal neurite outgrowth.

Experiment 4:

To investigate the influence of stimulation from repeated segments on neurite outgrowth, the length of low conductivity segments will be varied. Conduits will be seeded (inside with neurons, outside with Schwann cells) 24 hours prior to stimulation to allow cellular attachment. Using AC or DC stimulation as determined by Experiment 2 and the stimulation pattern as determined in Experiment 3, conduits will be stimulated as indicated in FIG. 33.

After three and five days, neurite outgrowth will be measured for all samples. Samples will be done in triplicate. Data will be statistically analyzed using a one-way ANOVA with Kruskal Wallis post hoc assessment. Comparison of the foregoing data will demonstrate if there is a difference in the influence of segmented stimulation on neurite outgrowth. Segment length will then be optimized based on the spacing parameter that induces maximal neurite outgrowth.

Mathematical Modeling.

The modeling approach begins with consideration of the structural and electrical properties of the device. In this situation, there is a hollow cylinder comprised of two types of alternately stacked segments. The two types of rings create an even cylinder so each has the same inner and outer diameters. The rings differ in length, resistance, and capacitance. That is, segment 1 has length (l1), resistance (r1), and capacitance (c1) at each occurrence in the tube. These properties follow for segment 2 only with different values. To set up electric field gradients, long segments (represented by segment 1) have a higher resistance and thus a lower conductivity than the short segments (represented by segment 2). The exact values for each of these variables can be supplied by experimental results above and from observed values in rat sciatic nerve. To simplify the problem, the tube will be assumed to be a solid structure (i.e., non-porous) surrounded and filled by dielectric media (saline and body fluid) of the same resistive and capacitive properties. Since the nerve outgrowth and maturity are assumed to be affected by the electrical stimulus, the key outcome measured from the electrical model is the electric field at a given point within the tube. No environmental electrical contributions have been demonstrated in literature from Schwann cells or extending neuritis. Therefore, this model does not include cellular contributions.

To represent the fields that exist in the system, Maxwell's equations are employed. The equations are general and can be applied to any given system using appropriate boundaries. Using these static equations, the electric and magnetic fields initially describe a field at a specific point in time, thus assuming a constant field. Inclusion of a time domain for changing field parameters is accomplished by multiplying $e^{\pm i\omega t}$ by the changing electric and magnetic fields, where i represents $(-1)^{1/2}$, $\omega$ is the frequency, and t is the time.

$$\nabla \cdot E = \frac{1}{\varepsilon_o}\rho \text{(Gauss's Law)}. \qquad 1$$

Where, $\nabla \cdot E$=divergence of the electromagnetic force; $\in_0$=permittivity of free space; $\rho$=charge density Gauss's law demonstrates that the divergence (the extent to which the vector E spreads out) of the electromagnetic field is equal to the charge density divided by the permittivity constant for the material. The permittivity constant is a measure of the material's ability to permit or transmit an electric field. Permittivity of free space represents the ability of a vacuum to transmit an electric field. The permittivity constant changes depending on the material evaluated and is represented by $$K = \frac{\epsilon}{\epsilon_p},$$

where $\in$ is the permittivity of the material and K is the dielectric constant. As a result, Gauss's Law becomes $\nabla \cdot E = K_p$. Permittivity and dielectric constants are important to note since the system being modeled is a polymer with two permittivity constants that will be placed in a media with a separate permittivity constant.

2. $\nabla \cdot B = 0$ (no name)

Where, $\nabla \cdot B$=divergence of the magnetic field.

Maxwell's second equation says that extent of spread of the magnetic field is zero in all directions. In other words, the magnetic field does not spread away from the source which generates it.

$$\nabla \times E = -\frac{dB}{dt}\text{(Faraday's Law)}. \qquad 3$$

Where, $\nabla \times E$=the curl of the electric field, $\frac{dB}{dt}$ = the change of the magnetic field with respect to time.

The curl of a vector reflects the rotation response of the changing vector. Frequently, curl is explained by the right hand rule. To find the curl, point your right hand in the direction of the vector of interest. Wrap your fingers in the direction of the second vector. For example, x×y or x curled around y is indicated in FIG. 34A. The rotation is clockwise around the z-axis. The direction of the curl (positive or negative) is determined by whether your thumb is pointed up or down relative to the axis. For example, in FIG. 34A, x×y results in the right hand thumb pointed up along the positive z-axis. The sign for the curl is then positive. In FIG. 34B, x×y results in the thumb pointing down along the negative z-axis, leaving the curl with a negative sign.

Faraday's law states that a magnetic field changing over time induces an electric field that curls around the charge. Further, the induced electric field curls in the opposite direction as would be induced by the changing electric field.

$$\nabla \times B = \mu_o J + \mu_o \varepsilon_o \frac{dE}{dt} \text{(Ampere's Law with Maxwell's correction)}. \qquad 4$$

Where, $\nabla \times B$=the curl of the magnetic field; J=volume current density;

$\mu_0$ = permeability of free space; $\varepsilon_o$ = permittivity of free space;

$\frac{dE}{dt}$ = the change of the electric field with respect to time.

Permeability is the equivalent constant for magnetic fields that permittivity is to electric fields. In essence, permeability is the extent to which a material is permeated by a magnetic field. Maxwell's fourth law explains that the current density in a volume and the change in the corresponding electric field over time induce a magnetic field, which curls around the current density and changing electric field in the same direction as induced by the current flow and the electric field. If the electric field is constant, then the second term is zero and the curl of the induced magnetic field is only influenced by the current density. As scalars, the permeability and permittivity constants are material factors which contribute to the magnitude of the resulting magnetic field curl but not the direction.

The aforementioned four general equations will be reduced to one equation by exploiting knowledge of the segmented nerve conduit system. The general equations will then be used with boundary conditions assuming linear media. Linear media implies that regardless of the direction of applied electrical field, the material would respond the same way. Homogenous materials are considered to behave linearly. Incorporation of nanoparticles in a random distribution allows the assumption of linear materials. An added stipulation of maintaining a low doping percentage of nanoparticles such that the nanoparticles can be assumed to be loosely distributed is required and met in this system. General boundary conditions for electrodynamics in linear media are expressed in terms of the electric and magnetic fields.

$$\in_1 E_1 \perp - \in_2 E_2 \perp = \sigma_f, \qquad \text{(i)}$$

where $\in_1$ and $\in_2$ are the permittivity constants for the two different materials, $E_1 \perp$ and $E_2 \perp$ are the electric fields perpendicular to the boundary, and $\sigma_f$ is the free charge density. This implies that the difference in the electric fields across the boundary is equal to the free charge density.

$$B_1 \perp - B_2 \perp = 0, \qquad \text{(ii)}$$

where $B_1 \perp$ and $B_2 \perp$ are the magnetic fields perpendicular to the boundary. This implies that the magnetic fields perpendicular to the boundary do not change across the boundary.

$$E_{1\parallel} - E_{2\parallel} = 0, \qquad \text{(iii)}$$

where $E_{1\parallel}$ and $E_{2\parallel}$ are the electric fields parallel to the boundary. This implies that the electric fields parallel to the boundary do not change across the boundary.

$$\left(\frac{1}{\mu_1}\right)B_{1\parallel} - \left(\frac{1}{\mu_2}\right)B_{2\parallel} = K_f \times \hat{n}, \quad \text{(iv)}$$

where $\mu_1$ and $\mu_2$ are permeabilities of the tow materials on their respective sides of the boundary, $B_{1\parallel}$ and $B_{2\parallel}$ are the magnetic fields parallel to the boundary, $K_f$ is the free current density, and $\hat{n}$ is the unit vector perpendicular to the interface. This implies that the free current density created by the electrical stimulation across the boundary is equal to the difference in the two parallel magnetic fields divided by the respective permeabilities of the two materials. The free current density is a quantity that can be measured or calculated from the oscilloscope measurements set forth above. Briefly, the measured current divided by the pulse rate from one end of the conduit to the outer is equal to the free current density.

For this application, boundary conditions will be identified between high and low conductivity segments and between the conduit wall and cell culture media. Critical measurements include the electric or magnetic field (one can be used to calculate the other), permittivity, and permeability. Permittivity will be found by measuring the charge of the material between two plates with an electrometer. Permeability and magnetic fields can be measured by a superconducting quantum interface device (SQUID). Together, the boundary conditions and the reduced Maxwell's equations will be solved computationally using the C programming language and Microsoft Visual C++ compiler with second order finite differencing to find the value of the electric field at a given point and time along or within the tube. The general order for the computation model begins with modeling the fluid within the tube. The general order for the computational model begins with modeling the fluid within the tube. The general order for the computational model begins with modeling the fluid within the tube, followed by a single segment of the tube, and then multiple segments of the tube. The electric field calculation will be calculated in the form of potential stimulation at a point. The potential at specific points within the conduit will be related linearly to the axonal outgrowth, direction, and maturity, in terms of length, direction of growth (angle and directness), and percent of myelination.

In conclusion, the aim is to maximize and simulate the electric field influence on neurite outgrowth by utilizing segmented conducting conduits which will be seeded and assessed in vitro. Specifically, biocompatibility, stimulation type and duration, and electric field gradient length will be evaluated in vitro via neuron and Schwann cell seeded conduits to maximize neurite outgrowth. Moreover, a mathematical model will be developed using the provided material's parameters, Maxwell's equations and the C programming language to simulate electrical effects on neurite outgrowth.

Example 5

Prospective Assessment of the Segmented Composite Conduction Conduits In Vivo Via the Rat Sciatic Nerve Model in Terms of Histologic, Electrophysiologic and Molecular Indicators.

Evaluation of a repair technique in an induced wound environment provides the most direct evidence for efficiency. The rat sciatic nerve model will be used to evaluation the segmented conducting conduits in vivo due to frequent use in research and surgical feasibility. Common evaluation techniques are grouped into three categories: functionality, electrophysiology, and histology. As external measures of nerve repair which eliminate behavioural complications in evaluation, toe out angle (TOA) and nociceptive functions will be evaluated. Since electrical function is key to confirmation of nerve repair, compound muscle action potential (CMAP) will be performed on rats in situ as an end point assessment. Nerve fiber count, N-ratio, and retrograde labelling of growth cones have previously demonstrated differences in nerve repair between experimental constructs. However, retrograde labelling strains tissue throughout the axon prior to explantation, restricting use of other staining options. To maximize assessment options, nerve fiber count and N-ratio will be the only histological techniques applied. To enhance understanding of connections between functional and observable macroscale effects and the micro and nanoscale responses, molecular and genetic regulation mechanisms which are known effectors of nerve injury and regeneration will be investigated. The presence of MAP1B and ROCK will be measured to monitor the responses of microtubules and actin to stimulation. Performance of RT-PCR for GAP-43, BDNF, and $\alpha_{II}$-tubulin will quantify gene expression for these known promoters of axon regeneration. RT-PCR of ATF-3 expression will identify or quantify, respectively, the number or relative extent of injured nerves.

From the in vitro study results, the optimal stimulation mode and duration, as well as length for low conducting segments will be used for in vivo evaluation. The effectiveness of the optimized scaffold and stimulation parameters will be assessed using the rat sciatic nerve transection model. To observe the response of cells in vivo to the stimulating conduits, no cells will be seeded prior to implantation. Each conduit will be open on both ends and filled with neutral buffered saline prior to wound closure as performed with surgical protocol existing approved conduits. Evaluation groups are listed in FIG. 35. Based on ANOVA power calculations ($\alpha$=0.05, power=0.8) with previously published experimental data comparing multiple treatment methods for sciatic nerve, 12 Sprague-Dawley rats (200-250 g) will be used for each group. The number of animals used for the study is outlined FIG. 36.

Injury will be created and scaffolds will be inserted according to the sciatic nerve model. Sciatic nerve defects 20 mm in length will be created via surgical removal and repaired with nerve conduits. Proximal and distal stumps will be secured via 10-0 silk sutures into the conduits to leave a 20 mm gap for repair. Conduits will be inserted with two polyurethane insulated stainless steel wires (Cooner A 5632) that will be stripped of insulation for 2-3 mm and twisted to form a small loop to secure one on the proximal and distal ends of the conduit, respectively for stimulation and grounding. Muscle and skin will be closed post conduit insertion. Each rat will receive one implant in the right leg which will be removed at either four or eight weeks. Conduit removal times are selected based on results from published experiments which indicate four weeks as an early time point to observe axon extension prior to complete repair and eight weeks as an upper boundary for repair in rats. At 10 weeks post injury, rats experience a natural nerve repair enhancement that is not duplicated in humans, which makes a 10 week time point too late for observations relevant to human repair. Animals will be observed daily and weight checked once per week to make sure they remain healthy.

Functional tests will be conducted prior to injury, 1 day post injury, and at 2, 4, and 8 weeks post injury. Examination of motor and sensory nerve function will be evaluated via TOA and heat sensory tests. TOA experiments will be conducted by placing a rat on an elevated Plexiglass runway with a mirror at a 45° angle below the platform and a darkened cage at the end as an animal attractant. A digital camera will be positioned beneath the platform perpendicular to the center of the walkway. The images will be transferred to a computer. The TOA is defined as the angle between the progression direction and a reference line at the sole of the foot starting at the midline and extending to the tip of the third digit. The increased experimental measures for this experiment will enable functional progression to be observed over the course of the study. Sensory nerve response will be assessed via the time and response of subjection of the injured rat paw to electrical stimulus of 0.18 mA (optimally) up to 1 mA to observe paw withdrawal. While sensory repair is minimally achieved (if at all) in long gap nerve repair, evaluation of possible repair will be conducted since effects of electrical stimulation have demonstrated sensory improvements.

Following functional tests at four and eight weeks, rats will be anesthetized for compound muscle action potential (CMAP) electrical evaluation. Although the conduit performs as a stimulus at the proximal end of the nerve, separate stimulating electrodes will be applied proximal to the injury/graft/conduit with measuring electrodes in the gastrocnemium, tibial, or plantar muscles. Using separate electrodes for CMAP permits consistency in stimulation for all samples. Time delay between signals, voltage amplitudes, and temperature will be recorded using oscilloscopes, a DAQ, and thermocouple. Measuring temperature during CMAP is crucial because an increase in 10° C. doubles in conduction velocity. Temperature will be controlled by warm or cool saline irrigation of the tissue, if necessary.

After CMAP recording, each rat will be asphyxiated via $CO_2$ and the conduit will be divided into thirds longitudinally and latitudinally for evaluation of proximal, middle, and distal segments via histology, Western blot, and RT-PCR. Samples from each group will be evaluated via histology for nerve fiber count and N-ratio (total number of myelinated fibers/total cable area). Western blot and RT-PCR will be performed on groups with highest and lowest functional and histological outcomes. A distinct contrast is expected between untreated and stimulated conduits. If a 10% repair difference is detected between the autografts and stimulated conduits, the Western blots and RT-PCR will instead be performed between the two repair techniques to discern molecularly regulated effects between the repair mechanisms. Protein levels from ROCK (Cell Signaling Technologies), RhoA (Cell Signaling Technologies), NGF (Cell Signaling Technologies), GSK3β (Cell Signaling Technologies), and MAP1B will be used together with macro level cell function, such as, axon outgrowth and direction to follow the two contrasting molecular pathways which promote and inhibit axon outgrowth. Additionally, RT-PCR will be used to assess expression of GAP-43, BDNF, and $\alpha_{II}$-tubulin. These gene effects are selected to enable correlation with regeneration and pathfinding (GAP-43), electrical sensitivity and regeneration (BDNF), and axon outgrowth and reconstruction of tubulin ($\alpha_{II}$-tubulin).

Functional and electrical tests will be performed in triplicate for each time point per animal. Statistical evaluation will be performed by ANOVA with Kruskal-Wallis post hoc assessment. This experiment will provide in vivo results to assess nerve repair response to segmented stimulation. The results will serve as an effectiveness indicator for future application to human patients.

In conclusion, the aim is to assess in vivo responses by utilizing segmented conducting conduits assessed in a rat sciatic nerve model. Specifically, conduits having optimized parameters will be compared to autografted, untreated, and nonstimulated conduit controls for functional, electrical, and morphological and molecular responses.

Example 6

An Additional Method of Preparing and Utilizing a PPy Formulation that is Soluble in a Variety of Solvents.

Polypyrrole may be synthesized in accordance with the present invention as follows: A 0.15 M $(Na)^+(DEHS)^-$ was first prepared in deionized water, the salt solution was heated and stirred to provide complete dissolution of the salt, and then the solution was chilled for at least about 15 minutes to 4° C. Pyrrole was then distilled according to procedures known to the person having ordinary skill in the art. Next, freshly distilled pyrrole (0.4 mol) was added dropwise into the $(Na)^+(DEHS)^-$ solution and stirred for at least 30 minutes and the solutions was cooled. A 0.4 M solution of Ammonium Persulfate (APS) was then prepared in deionized water and was allowed to cool for 30 minutes.

The cooled APS solution was then added dropwise into the $(Na)^+(DEHS)^-$/pyrrole solution by buret under vigorous magnetic stirring. The color of the solution is then observed to distinctly change from clear to dark blue or black. The reaction then continued and is kept under a cold environment with constant stirring for 16 to 24 hours.

The resulting reaction product was then washed with deionized water until the filtrate becomes neutral. Methanol should not be used to wash the PPy product as it dissolves the PPy. At least about 2 L of deionized water should be used to remove all foam or suds formation. To remove the PPy from the filter paper, one must first be sure the filter paper is wet from the water rinse. If the paper is dried overnight, it should first be rinsed with water. If possible, the PPy on paper should not be dried outright, to prevent particle aggregation.

After a brief water rinse, the filter with filtrate is placed into chloroform and stirred for approximately 15 minutes. The solution is then poured into a small glass dish and the chloroform is allowed to evaporate from the solution in a chemical hood. The process of chloroform addition and solvation, followed by pouring into a dish for evaporation, is repeated until the solution in the flask is clear. The PPy-DEHS is then recovered from both the reaction mixture outright and the filtrate.

Additionally, the solubility of the PPy-DEHS polymer salt was determined in a number of different solvents. Indeed, the PPy and PGSA, for example, have different solubility profiles. Therefore, determining formulations of PPy that are soluble in a wide range of solvents is advantageous. For example, both PPy-DEHS and PGSA are soluble in ethanol. Moreover, without being limited to any one theory of the invention, it is believed that the product of the present reaction forms a complex of PPy, APS, and DEHS (and also may include $H_2O$). Moreover, it was found that by increasing the equivalents of APS with respect to pyrrole, the yield of PPy also increased accordingly. Indeed, for 0.75:1 APS:Py, there is 71.1% yield of PPy; for 1:1 APS:Py, there is a 68.6% yield of PPy; and for 1.25:1 APS:Py, there is a 88.2% yield of PPy. In addition to yield, the equivalents of APS to Py, in the formation of the PPy of the present formulation, the ratio also has an effect on the solubility profile of the PPy salt.

Indeed, regarding the PPy of the present formulation, its solubility was determined, by mass, in chloroform, acetic acid, isopropanol, acetone, dichloromethane (DCM), dH$_2$O, methanol, dimethylsulfoxide (DMSO) and ethanol (Table 1).

TABLE 1

Solubility of PPy of the present formulation in a variety of solvents.

| Solvent | True Solubility (wt %) of APS:Py Formulations | | |
|---|---|---|---|
| | 0.75:1 | 1:1 | 1.25:1 |
| Chloroform | 5.9 | 4.3 | 11.1 |
| Acetic Acid | 9.1 | 4.0 | 3.5 |
| Isopropanol | 1.4 | 3.1 | 2.9 |
| Acetone | 1.0 | 3.0 | 4.7 |
| DCM | 3.6 | 2.5 | 2.4 |
| dH2O | 5.2 | 0.9 | 3.1 |
| Methanol | 5.8 | 2.7 | 2.5 |
| DMSO | 12.1 | 4.1 | 8.9 |
| Ethanol | 16.9 | 4.5 | — |

Upon preparation and recovery of the PPy, the PPy was then added with 0.1% Pluronic to chloroform (1.3 mg PPy/mL chloroform). The resulting solution was horn sonicated for 30 minutes at 35% intensity, 2 s on, 2 s off. PGSA was then be prepared and placed into a 2:1 solution with ethanol. The resulting solution could then be stirred well and ethanol may be heat evaporated from the solution at 100° C. for 2 hours. PPy solution was then added to PGSA at 0.05, 0.01, 0.005 and 0.001%. The solution was then vortexed and horn sonicated for 30 minutes. The solution was then poured onto the mold and UV crosslinked (as previously provided) to form structures as desired and disclosed herein.

Example 7

A Method for Preparing a Water Soluble PPy Formulation.

A water-soluble formulation of PPy may be prepared in accordance with the present invention utilizing, for example, the PPy prepared in Example 7. The method for preparing water soluble PPy may be as follows: Initially, PPy (20 mg) may be dissolved in toluene (20 mL). Next, water (20 mL) may be placed in an 80 mL or 200 mL beaker. To the beaker, the toluene/PPy suspension may be added. The resulting mixture phase separates so that the polymer/toluene solution is on top of the water. The mixture is then sonicated in a water bath until all of the toluene is dissolved over approximately 8 hours. The aqueous suspension is then filtered through a 0.2 micron Teflon or nylon filter to yield the water soluble PPy.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Furthermore, the transitional terms "comprising", "consisting essentially of" and "consisting of" when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All devices and methods for preparing the same that embody the present invention can, in alternate embodiments, be more specifically defined by any of the transitional terms "comprising", "consisting essentially of" and "consisting of".

REFERENCES

1. Evans G R D. Peripheral nerve injury: A review and approach to tissue engineered constructs. Anatomical Record 2001; 263(4):396-404.
2. Meek M F, Coert J H. US Food and Drug Administration/Conformit Europe-approved absorbable nerve conduits for clinical repair of peripheral and cranial nerves. Ann Plast Surg 2008 January; 60(1):110-116.
3. Sondell M, Lundborg G, Kanje M. Regeneration of the rat sciatic nerve into allografts made acellular through chemical extraction. Brain Res 1998 Jun. 8; 795(1-2):44-54.
4. Merle M, Dellon A L, Campbell J N, Chang P S. Complications from silicon-polymer intubulation of nerves. Microsurgery 1989; 10(2):130-133.
5. Meek M F, Coert J H. Clinical use of nerve conduits in peripheral-nerve repair: review of the literature. J Reconstr Microsurg 2002 February; 18(2):97-109.
6. Stryker. Stryker Neuromatrix. 2009 [cited 2009; Available from: http://www.stryker.com/en-us/products/Trauma/PeripheralNerveRepair/NeuroMatrix/index.htm
7. Integra. NeuraGen Nerve Guide. 2009 [cited 2009: Available from: http://www.integra-ls.com/products/?product=88
8. Stryker. Stryker Neuroflex. 2009 [cited 2009; Available from: http://www.stryker.com/en-us/products/Trauma/PeripheralNerveRepair/Neuroflex/index.htm
9. Polyganics. Neurolac. 2009 [cited 2009; Available from: http://www.polyganics.nl/index.php?id=19
10. Synovis Micro Companies Alliance 1. GEM Neurotube. 2009 [cited 2009; Available from: http://www.synovismicro.com/gem_neurotube.php
11. Integra. NeuraWrap Nerve Protector. 2009 [cited 2009; Available from: http://www.integra-ls.com/products/?product=198
12. SaluMedica. SaluBridge Physician Information. 2009 [cited 2009 May 21, 2009]; Available from: http://www.salumedica.com/salubridgeinfodoc.htm
13. FitzGerald M J T. Neuroanatomy: Basic and Clinical. Philadelphia: W.B. Saunders Company, Ltd., 1996.
14. Young P A, Young P H. Basic Clinical Neuroanatomy. Philadelphia: Lippincott Williams, and Wilkins, 1997.
15. MacKinnon S E, Dellon A L. Surgery of the Peripheral Nerve. Thieme Medical Publishers New York, 1988.
16. Medscape: Diseases of the Peripheral Nervous System. Web MD Inc., ACP Medicine, 2004.

17. Stoll G, Muller H W. Nerve injury, axonal degeneration and neural regeneration: basic insights. Brain Pathol 1999 April; 9(2):313-325.
18. Gordon T. The role of neurotrophic factors in nerve regeneration. Neurosurg Focus 2009; 26(2):E3.
19. Wood M D, Moore A M, Hunter D A, Tuffaha S, Borschel G H, Mackinnon S E, et al. Affinity-based release of glial-derived neurotrophic factor from fibrin matrices enhances sciatic nerve regeneration. Acta Biomater 2009 May; 5(4):959-968.
20. Hayashi A, Moradzadeh A, Tong A, Wei C, Tuffaha S H, Hunter D A, et al. Treatment modality affects allograft-derived Schwann cell phenotype and myelinating capacity. Exp Neurol 2008 August; 212(2):324-336.
21. Lee A C, Yu V M, Lowe J B, 3$^{rd}$, Brenner M J, Hunter D A, Mackinnon S E, et al. Controlled release of nerve growth factor enhances sciatic nerve regeneration. Exp Neurol 2003 November; 184(1):295-303.
22. Deister C, Schmidt C E. Optimizing neurotrophic factor combinations for neurite outgrowth. J Neural Eng 2006 June; 3(2):172-179.
23. Ahmed I, Liu H Y, Mamiya P C, Ponery A S, Babu A N, Weik T, et al. Three-dimensional nanofibrillar surfaces covalently modified with tenascin-C-derived peptides enhance neuronal growth in vitro. J Biomed Mater Res A 2006 Mar. 15; 76(4):851-860.
24 Zhang L, Ma Z, Smith G M, Wen X, Pressman Y, Wood P M, et al. GDNF-enhanced axonal regeneration and myelination following spinal cord injury is mediated by primary effects on neurons. Glia 2009 Jan. 23.
25. Zhang X, MacDiarmid A G, Manohar S K. Chemical synthesis of PEDOT nanofibers. Chem Commun (Camb) 2005 Nov. 14(42):5328-5330.
26. Kim Y T, Haftel V K, Kumar S. Bellamkonda R V. The role of aligned polymer fiber-based constructs in the bridging of long peripheral nerve gaps. Biomaterials 2008 July; 29(21):3117-3127.
27. Yang F, Murugan R, Wang S, Ramakrishna S. Electrospinning of nano/microscale poly(L-lactic acid) aligned fibers and their potential in neural tissue engineering. Biomaterials 2005 May; 26(15):2603-2610.
28. Wen X, Tresco P A. Effect of filament diameter and extracellular matrix molecule precoating on neurite outgrowth and Schwann cell behavior on multifilament entubulation bridging device in vitro. J Biomed Mater Res A 2006 Mar. 1; 76(3):626-637.
29. Corey J M, Lin D Y, Mycek K B, Chen Q, Samuel S, Feldman E L, et al. Aligned electrospun nanofibers specify the direction of dorsal root ganglia neurite growth. J Biomed Mater Res A 2007 Dec. 1; 83(3):636-645.
30. Fan Y W, Cui F Z, Chen L N, Zhai Y, Xu Q Y, Lee I S. Adhesion of neural cell son silicon wafer with nano-topographic surface. Applied Surface Science 2002; 187(3-4):313-318.
31. Schmalenberg K E, Uhrich K E. Micropatterned polymer substrates control alignment of proliferating Schwann cells to direct neuronal regeneration. Biomaterials 2005 April; 26(12):1423-1430.
32. Bruder J M, Lee A P, Hoffman-Kim D. Biomimetic materials replicating Schwann cell topography enhance neuronal adhesion and neurite alignment in vitro. J Biomater Sci Polym Ed 2007; 18(8):967-982.
33. Borschel G H, Kia K F, Kuzon W M, Jr., Dennis R G. Mechanical properties of acellular peripheral nerve. J Surg Res 2003 October; 114(2):133-139.
34. Rydevik B L, Kwan M K, Myers R R, Brown R A, Triggs K J, Woo S L Y, et al. AN INVITRO MECHANICAL AND HISTOLOGICAL STUDY OF ACUTE STRETCHING ON RABBIT TIBIAL NERVE. Journal of Orthopaedic Research 1990; 8(5):694-701.
35. Guan J, Stankus J J, Wagner W R. Biodegradable elastomeric scaffolds with basic fibroblast growth factor release. Journal of Controlled Release 2007; 120(1-2):70-78.
36. Guan Y Q, Tao H M, Li Y C, Wang W W, Li Z B, Peng C L. Preparation and activity of a nanometer anti-microbial polyurethane. Journal of Wuhan University of Technology-Materials Science Edition 2009; 24(4):540-545.
37. Wang S, Wan A C, Xu X, Gao S, Mao H Q, Leong K W, et al. A new nerve guide conduit material composed of a biodegradable poly(phosphoester). Biomaterials 2001 May; 22(10):1157-1169.
38. Wang W, Itoh S, Matsuda A, Ichinose S, Shinomiya K, Hata Y, et al. Influences of mechanical properties and permeability on chitosan nano/microfiber mesh tubes as a scaffold for nerve regeneration. J Biomed Mater Res A 2008 February; 84(2):557-566.
39. Ciardelli G, Rechichi A, Cerrai P, Tricoli M, Barbani N, Giusti P. Segmented polyurethanes for medical applications: Synthesis, characterization and in vitro enzymatic degradation studies. Macromolecular Symposia 2004; 218:261-271.
40. Evans A J, Thompson B C, Wallace G G, Millard R, O'Leary S J, Clark G M, et al. Promoting neurite outgrowth from spiral ganglion neuron explants using polypyrrole/BDNF-coated electrodes. J Biomed Mater Res A 2009 October; 91(1):241-250.
41. Cho Y, Shi R, Ivanisevic A, Ben Borgens R. A mesoporous silica nanosphere-based drug delivery system using an electrically conducting polymer. Nanotechnology 2009 Jul. 8; 20(27):275102.
42. Guimard N K, Gomez N, Schmidt C E. Conducting polymers in biomedical engineering. Progress in Polymer Science 2007; 32:876-921.
43. Thompson B C, Richardson R T, Moulton S E, Evans A J, O'Leary S, Clark G M, et al. Conducting polymers, dual neurotrophins and pulsed electrical stimulation—Dramatic effects on neurite outgrowth. J Control Release 2009 Sep. 27.
44. Cullen D K, A R P, Doorish J F, Smith D H, Pfister B J. Developing a tissue-engineered neural-electrical relay using encapsulated neuronal constructs on conducting polymer fibers. J Neural Eng 2008 December; 5(40:374-384.
45. Cui X, Lee V A, Raphael Y, Wiler J A, Hetke J F, Anderson D J, et al. Surface modification of neural recording electrodes with conducting polymer/biomolecule blends. J Biomed Mater Res 2001 August; 56(2): 261-272.
46. Murphy C J, Jana N R. Controlling the aspect ratio of inorganic nanorods and nanowires. Adv Mater 2002 January; 14(1):80-82.
47. Li J, Ma P C, Chow W S, To C K, Tang B Z, Kim J K. Correlations between percolation threshold, dispersion state, and aspect ratio of carbon nanotubes. Advanced Functional Materials 2007; 17(16):3207-3215.
48. Bauhofer W, Kovacs J Z. A review and analysis of electrical percolation in carbon nanotube polymer composites. Composites Science and Technology 2009; 69(10):1486-1498.
49. Hernandez J J, Garcia-Gutierrez M C, Nogales A, Rueda D R, Kwiatkowska M, Szymczyk A, et al. Influence of preparation procedure on the conductivity and transparency of SWCNT-polymer nanocomposites. Composites Science and Technology 2009; 69(11-12):1867-1872.
50. Caswell K K, Bender C M, Murphy C J. Seedless, surfactantless wet chemical synthesis of silver nanowires. Nano Lett 2003 May; 3(5):667-669.
51. Gole A, Murphy C J. Seed-mediated synthesis of gold nanorods: Role of the size and nature of the seed. Chem Mat 2004 September; 16(19):3633-3640.
52. De S, Higgins T M, Lyons P E, Doherty E M, Nirmalraj P N, Blau W J, et al. Silver Nanowire Networks as Flexible, Transparent, Conducting Films: Extremely High DC to Optical Conductivity Ratios. ACS Nano 2009 July; 3(7):1767-1774.
53. Kostarelos K. The long and short of carbon nanotube toxicity. Nature Biotechnology 2008; 26(7):774-776.
54. Lam C W, James J T, McCluskey R, Arepalli S, Hunter R L. A review of carbon nanotube toxicity and assessment of potential occupational and environmental health risks. Critical Reviews in Toxicology 2006; 36(3):189-217.
55 Zhang X P, Sun B Q, Friend R H, Guo H C, Nau D, Giessen H. Metallic photonic crystals based on solution-processable gold nanoparticles. Nano Lett 2006 April; 6(4):651-655.
56. Kalbacova M, Kalbac M, Dunsch L, Kataura H, Hempel U. The study of the interaction of human mesenchymal stem cells and monocytes/macrophages with single-walled carbon nanotube films. Phys Status Solidi B-Basic Solid State Phys 2006 November; 243(13):3514-3518.
57. Kalbacova M, Kalbac M, Dunsch L, Kromka A, Vanecek M, Rezek B, et al. The effect of SWCNT and nanodiamond films on human osteoblast cells. Phys Status Solidi B-Basic Solid State Phys 2007; 244(11):4356-4359.
58. Hu H, Ni Y C, Montana V, Haddon R C, Parpura V. Chemically functionalized carbon nanotubes as substrates for neuronal growth. Nano Lett 2004; 4(3):507-511.
59. Wang L M, Li Y F, Zhou L J, Liu Y, Meng L, Zhang K, et al. Characterization of gold nanorods in vivo by integrated analytical techniques: their uptake, retention, and chemical forms. Anal Bioanal Chem February; 396(3):1105-1114.
60. Chen X, Schluesener H J. Nanosilver: A nanoproduct in medical application. Toxicol Lett 2008 January; 176(1):1-12.
61. Carlson C, Hussain S M, Schrand A M, Braydich-Stolle L K, Hess K L, Jones R L, et al. Unique Cellular Interaction of Silver Nanoparticles: Size-Dependent Generation of Reactive Oxygen Species. J Phys Chem B 2008; 112(43):13608-13619.
62. AshaRani P V, Hande M P, Valiyaveettil S. Anti-proliferative activity of silver nanoparticles. BMC Cell Biol 2009 September; 10:14.
63. Alkilany A M, Nagaria P K, Hexyl C R, Shaw T J, Murphy C J, Wyatt M D. Cellular Uptake and Cytotoxicity of Gold Nanorods: Molecular Origin of Cytotoxicity and Surface Effects. Small 2009 March; 5(6):701-708.
64. Bashar S A. Study of Indium Tin Oxide (ITO) for Novel Optoelectronic Devices. King's College London: University of London; 1998.
65. Mitsumoto H, Tsuzaka K. Neurotrophic factors and neuromuscular disease: I. General comments, the neurotrophin family, and neuropoietic cytokines. Muscle Nerve 1999 August; 22(8):983-999.
66. Jones D M, Tucker B A, Rahimtula M, Mearow K M. The synergistic effects of NGF and IGF-1 on neurite growth in adult sensory neurons: convergence on the PI 3-kinase signaling pathway. J Neurochem 2003 September; 86(5):1116-1128.
67. Sakiyama-Elbert S E, Hubbell J A. Controlled release of nerve growth factor from a heparin-containing fibrin-based cell ingrowth matrix. J Control Release 2000 Oct. 3; 69(1):149-158.
68. Webber C A, Xu Y, Vanneste K J, Martinez J A, Verge V M, Zochodne D W. Guiding adult Mammalian sensory axons during regeneration. J Neuropathol Exp Neurol 2008 March; 67(3):212-222.
69. Xu X, Yee W C, Hwang P Y, Yu H, Wan A C, Gao, et al. Peripheral nerve regeneration with sustained release of poly(phosphoester) microencapsulated nerve growth factor within nerve guide conduits. Biomaterials 2003 June; 24(13):2405-2412.
70. Boyd J G, Gordon T. A dose-dependent facilitation and inhibition of peripheral nerve regeneration by brain-derived neurotrophic factor. Eur J Neurosci 2002 February; 15(4):613-626.
71. Batchelor P E, Porritt M J, Martinello P, Parish C L, Liberatore G T, Donnan G A, et al. Macrophages and Microglia Produce Local Trophic Gradients That Stimulate Axonal Sprouting Toward but Not beyond the Wound Edge. Mol Cell Neurosci 2002 November; 21(3):436-453.
72. Batchelor P E, Wills T E, Hewa A P, Porritt M J, Howells D W. Stimulation of axonal sprouting by trophic factors immobilized within the wound core. Brain Res 2008 May 13; 1209:49-56.
73. Barras F M, Pasche P, Bouche N, Aebischer P, Zurn A D. Glial cell line-derived neurotrophic factor released by synthetic guidance channels promotes facial nerve regeneration in the rat. J Neurosci Res 2002 Dec. 15; 70(6):746-755.
74. Ohta M, Suzuki Y, Chou H, Ishikawa N, Suzuki S, Tanihara M, et al. Novel heparin/alginate gel combines with basic fibroblast growth factor promotes nerve regeneration in rat sciatic nerve. J Biomed Mater Res A 2004 Dec. 15; 71(4):661-668.
75. Winseck A K, Caldero J, Ciutat D, Prevette D, Scott S A, Wang G, et al. In vivo analysis of Schwann cell programmed cell death in the embryonic chick: regulation by axons and glial growth factor. J Neurosci 2002 Jun. 1; 22(11):4509-4521.
76. Bryan D J, Holway A H, Wang K K, Silva A E, Trantolo D J, Wise D, et al. Influence of glial growth factor and Schwann cells in a bioresorbable guidance channel on peripheral nerve regeneration. Tissue Eng 2000 April; 6(2):129-138.
77. Zurn A D, Winkel L, Menoud A, Djabali K, Aebischer P. Combined effects of GDNF, BDNF, and CNTF on motoneuron differentiation in vitro. J Neurosci Res 1996 Apr. 15; 44(2):133-141.
78. Bailey S B, Eicheler M E, Villadiego A, Rich K M. The influence of fibronectin and laminin during Schwann cell migration and peripheral nerve regeneration through silicon chambers. J Neurocytol 1993 March; 22(3):176-184.
79. Woolley A L, Hollowell J P, Rich K M. First place—Resident Basic Science Award 1990. Fibronectin-laminin combination enhances peripheral nerve regeneration across long haps. Otolaryngol Head Neck Surg 1990 October; 103(4):509-518.
80. Dertinger S K, Jiang X, Li Z, Murthy V N, Whitesides G M. Gradients of substrate-bound laminin orient axonal specification of neurons. Proc Natl Acad Sci USA 2002 Oct. 1; 99(20):12542-12547.

81. Li G N, Liu J, Hoffman-Kim D. Multi-molecular gradients of permissive and inhibitory cues direct neurite outgrowth. Ann Biomed Eng 2008 June; 36(6):889-904.
82. Sta Iglesia D D, Cragoe E J, Jr., Vanable J W, Jr. Electric field strength and epithelization in the newt (*Notophthalmus viridescens*). J Exp Zool 1996 Jan. 1; 274(1):56-62.
83. Sta Iglesia D D, Vanalbe J W, Jr. Endogenous lateral electric fields around bovine corneal lesions are necessary for and can enhance normal rates of wound healing. Wound Repair Regen 1998 November-December; 6(6): 531-542.
84. Song B, Zhao M, Forrester J, McCaig C. Nerve regeneration and wound healing are stimulated and directed by an endogenous electrical field in vivo. Journal of Cell Science 2004; 117(20):4681-4690.
85. Chiang M, Robinson K R, Vanable J W, Jr. Electrical fields in the vicinity of epithelial wounds in the isolated bovine eye. Exp Eye Res 1992 June; 54(6):999-1003.
86. Huang J, Hu X, Lu L, Ye Z, Zhang Q, Luo Z. Electrical regulation of Schwann cells using conductive polypyrrole/chitosan polymers. J Biomed Mater Res A 2009 Jun. 17.
87. Supronowicz P R, Ajayan P M, Ullmann K R, Arulanandam B P, Metzger D W, Bizios R. Novel current-conducting composite substrates for exposing osteoblasts to alternating current stimulation. J Biomed Mater Res 2002 Mar. 5; 59(30:499-506.
88. Borgens R B, Vanable J W, Jr. Jaffe L F. Bioelectricity and regeneration: large currents leave the stumps of regenerating newt limbs. Proc Natl Acad Sci USA 1977 October; 74(10):4528-4532.
89. Al-Majed A A, Neumann C M, Brushart T M, Gordon T. Brief electrical stimulation promotes the speed and accuracy of motor axonal regeneration. J Neurosci 2000 Apr. 1; 20(7):2602-2608.
90. Marsh G, Beams H W. IN VITRO CONTROL OF GROWING CHICK NERVE FIBERS BY APPLIED ELECTRIC CURRENTS. Journal of Cellular and Comparative Physiology 1946; 27:139-157.
91. Macias M Y, Battocletti J H, Sutton C H, Pintar F A, Maiman D J. Directed and enhanced neurite growth with pulsed magnetic field stimulation. Bioelectromagnetics 2000 May; 21(4):272-286.
92. Zhao M, Dick A, Forrester J V, McCaig C D. Electric field-directed cell motility involves up-regulated expression and asymmetric redistribution of the epidermal growth factor receptors and is enhanced by fibronectin and laminin Molecular Biology of the Cell 1999; 10(4): 1259-1276.
93. Rajnicek A M, Robinson K R, McCaig C D. The direction of neurite growth in a weak DC electric field depends on the substratum: Contributions of adhesivity and net surface charge. Dev Biol 1998 November; 203 (2):412-423.
94. McCaig C D, Sangster L, Stewart R. Neurotrophins enhance electric field-directed growth cone guidance and directed nerve branching. Dev Dyn 2000 March; 217(3): 299-308.
95. Evans P J, Bain J R, Mackinnon S E, Makino A P, Hunter D A. Selective reinnervation: a comparison of recovery following microsuture and conduit nerve repair. Brain Res 1991 Sep. 20; 559(2):315-321.
96. Wang S, Cai Q, Hou J, Bei J, Zhang T, Yang J, et al. Acceleration effect of basic fibroblast growth factor on the regeneration of peripheral nerve through a 15-mm gap. J Biomed Mater Res A 2003 Sep. 1; 66(3):522-531.
97. Vleggeert-Lankamp C L. The role of evaluation methods in the assessment of peripheral nerve regeneration through synthetic conduits: a systematic review. Laboratory investigation. J Neurosurg 2007 December; 107(6): 1168-1189.
98. Chamberlain L J, Yannas I V, Hsu H P, Strichartz G R, Sepctor M. Near-terminus axonal structure and function following rat sciatic nerve regeneration through a collagen-GAG matrix in a ten-millimeter gap. J Neurosci Res 2000 Jun. 1; 610(5):66-677.
99. Fine E G, Decosterd I, Papaloizos M, Zurn A D, Aebischer P. GDNF and NGF released by synthetic guidance channels support sciatic nerve regeneration across a long gap. Eur J Neurosci 2002 February; 15(4):589-601.
100. Udina E, Furey M, Busch S, Silver J, Gordon T, Fouad K. Electrical stimulation of intact peripheral sensory axons in rats promotes outgrowth of their central projections. Exp Neurol 2008 March; 210(1):238-247.
101. Al-Majed A A, Brushart T M, Gordon T. Electrical accelerates and increases expression of BDNF and trkB Mrna in regenerating rat femoral motoneurons. Eur J Neurosci 2000 December; 12(12):4381-4390.
102. Al-Majed A A, Tam S L, Gordon T. Electrical stimulation accelerates and enhances expression of regeneration-associated genes in regenerating rat femoral motoneurons. Cell Mol Neurobiol 2004 June; 24(3):379-402.
103. Zhang J, Lineaweaver W C, Oswald T, Chen Z, Zhang F. Ciliary neurotrophic factor for acceleration of peripheral nerve regeneration: an experimental study. J Reconstr Microsurg 2004 May; 20(4):323-327.
104. Varejao A S, Melo-Pinto P, Meek M F, Filipe V M, Bulas-Cruz J. Methods for the experimental functional assessment of rat sciatic nerve regeneration. Neurol Res 2004 March; 26(2):186-194.
105. Varejao A S, Cabrita A M, Geuna S, Melo-Pinto P, Filipe V M, Gramsbergen A, et al. Toe out angle: a functional index for the evaluation of sciatic nerve recovery in the rat model. Exp Neurol 2003 October; 183(20: 695-699.
106. Song Y X, Muramatsu K, Kurokawa Y, Kuriyama R, Sakamoto S, Kaneko K, et al. Functional recovery of rat hind-limb allografts. J Reconstr Microsurg 2005 October; 21(7):471-476.
107. Bain J R, Mackinnon S E, Hunter D A. Functional evaluation of complete sciatic, peroneal, and posterior tibial nerve lesions in the rat. Plast Reconstr Surg 1989 January; 83(1):129-138.
108. Luis A L, Rodrigues J M, Lobato J V, Lopes M A, Amado S, Veloso A P, et al. Evaluation of two biodegradable nerve guides for the reconstruction of the rat sciatic nerve. Biomed Mater Eng 2007; 17(1):39-52.
109. Gonzalez-Billault C, Jimenez-Mateos E M, Caceres A, Diaz-Nido J, Wandosell F, Avila J. Microtube-associated protein 1B function during normal development, regeneration, and pathological conditions in the nervous system. J Neurobiol 2004 January; 58(1):48-59.
110. Pigino G, Paglini G, Ulloa L, Avila J, Caceres A. Analysis of the expression, distribution and function of cyclin dependent kinase 5 (cdk5) in developing cerebellar macroneurons. J Cell Sci 1997 January; 110 (Pt 2):257-270.
111. Franzen R, Tanner S L, Dashiell S M, Rottkamp C A, Hammer J A, Quarles R H. Microtubule-associated protein 1B: a neuronal binding partner for myelin-associated glycoprotein. J Cell Biol 2001 Dec. 10; 155(6):893-898.

112. Riederer B M, Moya F, Calvert R. Phosphorylated MAP1b, alias MAP5 and MAP1x, is involved in axonal growth and neuronal mitosis. Neuroreport 1993 June; 4(6):771-774.
113. Bouquet C, Ravaille-Veron M, Propst F, Nothias F. MAP1B coordinates microtubule and actin filament remodeling in adult mouse Schwann cell tips and DRG neuron growth cones. Mol Cell Neurosci 2007 October; 36(2):235-247.
114. Garcia-Perez J, Avila J, Diaz-Nido J. Implication of cyclin-dependent kinases and glycogen synthase kinase 2 in the phosphorylation of microtubule-associated protein 1B in developing neuronal cells. J Neurosci Res 1998 May 15; 52(4):445-452.
115. Goold R G, Gordon-Weeks P R. The MAP kinase pathway is upstream of the activation of GSK3beta that enables it to phosphorylate MAP1B and contributes to the stimulation of axon growth. Mol Cell Neurosci 2005 March; 28(3):524-534.
116. Goold R G, Gordon-Weeks P R. Glycogen synthase kinase 3beta and the regulation of axon growth. Biochem Soc Trans 2004 November; 32(Pt 5):809-811.
117. Goold R G, Gordon-Weeks P R. NGF activates the phosphorylation of MAP1B by GSK3beta through the TrkA receptor and not the p75(NTR) receptor. J Neurochem 2003 November; 87(4):935-946.
118. Cheng C, Webber C A, Wang J, Xu Y, Martinez J A, Liu W Q, et al. Activated RHOA and peripheral axon regeneration. Exp Neurol 2008 August; 212(2):358-369.
119. Gallo G. RhoA-kinase coordinates F-actin organization and myosin II activity during semaphoring-3A-induced axon retraction. J Cell Sci 2006 Aug. 15; 119(Pt 16):3413-3423.
120. Loudon R P, Silver L D, Yee H F, Jr., Gallo G. RhoA-kinase and myosin II are required for the maintenance of growth cone polarity and guidance by nerve growth factor. J Neurobiol 2006 July; 66(8):847-867.
121. Melendez-Vasquez C V, Einheber S, Salzer J L. Rho kinase regulates Schwann cell myelination and formation of associated axonal domains. J Neurosci 2004 Apr. 21; 24(16):3953-3963.
122. Sherman D L, Brophy P J. Mechanisms of axon ensheathment and myelin growth. Nat Rev Neurosci 2005 September; 6(9):683-690.
123. Sharma N, Marzo S J, Jones K J, Foecking E M. Electrical stimulation and testosterone differentially enhance expression of regeneration-associated genes. Exp Neurol 2009 May 7.
124. Tsujino H, Kondo E, Fukuoka T, Dai Y, Tokunaga A, Miki K, et al. Activating transcription factor 3 (ATF3) induction by axotomy in sensory and motoneurons: A novel neuronal marker of nerve injury. Mol Cell Neurosci 2000 February; 15(2):170-182.
125. Geremia N M, Gordon T, Brushart T M, Al-Majed A A, Verge V M. Electrical stimulation promotes sensory neuron regeneration and growth-associated gene expression. Exp Neurol 2007 June; 205(2):347-359.
126. McIntyre C C, Richardson A G, Grill W M. Modeling the excitability of mammalian nerve fibers: influence of afterpotentials on the recovery cycle. J Neurophysiol 2002 February; 87(2):995-1006.
127. Shanthaveerappa T R, Bourne G H. Histological and histochemical studies of the choroid of the eye and its relations to the pia-arachnoid mater of the central nervous system and perineural epithelium of the peripheral nervous system. Acta Anat (Basel) 1965; 61(3):379-398.
128. Jana N R, Gearheart L, Murphy C J. Wet chemical synthesis of high aspect ratio cylindrical gold nanorods. J Phys Chem B 2001 May; 105(19):4065-4067.
129. Johnson E O, Soucacos P N. Nerve repair: experimental and clinical evaluation of biodegradable artificial nerve guides. Injury 2008 September; 39 Suppl 3:S30-36.
130. Hudson T W, Evans G R, Schmidt C E. Engineering strategies for peripheral nerve repair. Orthop Clin North Am 2000 July; 31(3):485-498.
131. Wang S, Yaszemski M J, Knight A M, Gruetzmacher J A, Currier B L, Yaszemski M J. Synthesis and characterizations of biodegradable and crosslinkable poly(epsilon-caprolactone fumarate), poly(ethylene glycol) fumarate), and their amphiphilic copolymer. Biomaterials 2006 February; 27(6):832-841.
132. Wang S, Yaszemski M J, Knight A M, Gruetzmacher J A, Windebank A J, Lu L. Photo-crosslinked poly(epsilon-caprolactone fumarate) networks for guided peripheral nerve regeneration: material properties and preliminary biological evaluations. Acta Biomater 2009 June; 5(5): 1531-1542.
133. Hadlock T, Sundback C, Hunter D, Cheney M, Vacanti J P. A polymer foam conduit seeded with Schwann cells promotes guided peripheral nerve regeneration. Tissue Engineering 2000; 6(20):119-127.
134. Chang C J, Hsu S H, Yen H J, Chang H, Hsu S K. Effects of unidirectional permeability in asymmetric poly (DL-lactic acid-co-glycolic acid) conduits on peripheral nerve regeneration: An in vitro and in vivo study. J Biomed Mater Res Part B 2007 October; 83B(1):206-215.
135. Hollowell J P, Villadiego A, Rich K M. Sciatic nerve regeneration across gaps within silicone chambers: long-term effects of NGF and consideration of axonal branching. Exp Neurol 1990 October; 110(1):45-51.
136. Lietz M, Dreesmann L, Hoss M, Oberhoffner S, Schlosshauer B. Neuro tissue engineering of glial nerve guides and the impact of different cell types. Biomaterials 2006 March; 27(8):1425-1436.
137. Song J, Cheng Q, Kopta S, Stevens R C. Modulating artificial membrane morphology: pH-induced chromatic transition and nanostructural transformation of a bolaamphiphilic conjugated polymer from blue helical ribbons to red nanofibers. J Am Chem Soc 2001 Apr. 11; 123(14): 3205-3213.
138. Kehoe S, Zhang X F, Boyd D. FDA approved guidance conduits and wraps for peripheral nerve injury: A review of materials and efficacy. Injury-Int J Care Inj May; 43(5):553-572.
139. Pomerantseva I, Krebs N, Hart A, Neville C M, Huang A Y, Sundback C A. Degradation behavior of poly(glycerol sebacate). J Biomed Mater Res Part A 2009 December; 91A(4):1038-1047.
140. Wang Y D, Ameer G A, Sheppard B J, Langer R. A tough biodegradable elastomer. Nature Biotechnology 2002 June; 20(6):602-606.
141. Nijst C L E, Bruggeman J P, Karp J M, Ferreira L, Zumbuehl A, Bettinger C J, et al. Synthesis and characterization of photocurable elastomers from poly(glycerol-co-sebacate). Biomacromolecules 2007 October; 8(10): 3067-3073.
142. Gerecht S, Townsend S A, Pressler H, Zhu H, Nijst C L E, Bruggeman J P, et al. A porous photocurable elastomer for cell encapsulation and culture. Biomaterials 2007 November; 28(32):4826-4835.
143. Svennersten K, Bolin M H, Jager E W H, Berggren M, Richter-Dahlfors A. Electrochemical modulation of epi- 144. Luo X L, Weaver C L, Zhou D D, Greenberg R, Cui X Y T. Highly stable carbon nanotube doped poly(3,4-ethylenedioxythiophene) for chronic neural stimulation. Biomaterials August; 32(24):5551-5557.

145. Abidian M R, Martin D C. Experimental and theoretical characterization of implantable neural microelectrodes modified with conducting polymer nanotubes. Biomaterials 2008 March; 29(9):1273-1283.

146. Edwards S L, Church J S, Werkmeister J A, Ramshaw J A M. Tubular micro-scale multiwalled carbon nanotube-based scaffolds for tissue engineering. Biomaterials 2009 March; 30(9):1725-1731.

147. Shi G X, Rouabhia M, Wang Z X, Dao L H, Zhang Z. A novel electrically conductive and biodegradable composite made of polypyrrole nanoparticles and polylactide. Biomaterials 2004 June; 25(13):2477-2488.

148. George P M, Lyckman A W, LaVan D A, Hegde A, Leung Y, Avasare R, et al. Fabrication and biocompatibility of polypyrrole implants suitable for neural prosthetics. Biomaterials 2005 June; 26(17):3511-3519.

149. Ifkovits J L, Devlin J J, Eng G, Martens T P, Vunjak-Novakovic G, Burdick J A. Biodegradable Fibrous Scaffolds with Tunable Properties Formed from Photo-Cross-Linkable Poly(glycerol sebacate). ACS Appl Mater Interfaces 2009 September; 1(9):1878-1886.

150. Liu Q Y, Tian M, Ding T, Shi R, Feng Y X, Zhang L Q, et al. Preparation and characterization of a thermoplastic poly(glycerol sebacate) elastomer by two-step method. J Appl Polym Sci 2007 February; 103(3):1412-1419.

151. Evans G R. Challenges to nerve regeneration. Semin Surg Oncol 2000 October-November; 19(3):312-318.

152. Chamberlain L J, Yannas I V, Hsu H P, Strichartz G R, Spector M. Near-terminus axonal structure and function following rat sciatic nerve regeneration through a collagen-GAG matrix in a ten-millimeter gap. J Neurosci Res 2000 Jun. 1; 60(5):666-677.

153. Zhang D H, Kandadai M A, Cech J, Roth S, Curran S A. Poly(L-lactide) (PLLA)/multiwalled carbon nanotube (MWCNT) composite: Characterization and biocompatibility evaluation. J Phys Chem B 2006; 110(26):12910-12915.

154. Schense J C, Bloch J, Aebischer P, Hubbell J A. Enzymatic incorporation of bioactive peptides into fibrin matrices enhances neurite extension. Nature Biotechnology 2000 April; 18(4):415-419.

155. Chen Y S, Hsieh C L, Tsai C C, Chen T H, Cheng W C, Hu C L, et al. Peripheral nerve regeneration using silicone rubber chambers filled with collagen, laminin and fibronectin. Biomaterials 2000 August; 21(15):1541-1547.

156. Evans G R D, Brandt K, Katz S, Chauvin P, Otto L, Bogle M, et al. Bioactive poly(L-lactic acid) conduits seeded with Schwann cells for peripheral nerve regeneration. Biomaterials 2002 February; 23(3):841-848.

157. Goldner J S, Bruder J M, Li G, Gazzola D, Hoffman-Kim D. Neurite bridging across micropatterned grooves. Biomaterials 2006 January; 27(3):460-472.

158. Abrams G A, Goodman S L, Nealey P F, Franco M, Murphy C J. Nanoscale topography of the basement membrane underlying the corneal epithelium of the rhesus macaque. Cell Tissue Res 2000 January; 299(1):39-46.

159. Miller C, Jeftinija S, Mallapragada S. Micropatterned Schwann cell-seeded biodegradable polymer substrates significantly enhance neurite alignment and outgrowth. Tissue Engineering 2001 December; 7(6):705-715.

160. Zhao M, AgiusFernandez A, Forrester J V, McCaig C D. Orientation and directed migration of cultured corneal epithelial cells in small electric fields are serum dependent. Journal of Cell Science 1996 June; 109:1405-1414.

161. Zhao M, McCaig C D, AgiusFernandez A, Forrester J V, ArakiSasaki K. Human corneal epithelial cells reorient and migrate cathodally in a small applied electric field. Current Eye Research 1997; 16(10):973-984.

162. Baron-Van Evercooren A, Kleinman H K, Ohno S, Marangos P, Schwartz J P, Dubois-Dalcq M E. Nerve growth factor laminin and fibronective promote neurite growth in human fetal sensory ganglia cultures. Journal of Neuroscience Research 1982; 8(2-3):179-194.

163. Cheng H, Hoffer B, Stromberg I, Russell D, Olson L. The effect of glial-cell line-derived neurotrophic factor in fibrin glue on developing dopamine neurons. Exp Brain Res 1995 May; 104(2):199-206.

164. Edelman E R, Mathiowitz E, Langer R, Klagsbrun M. Controlled and modulated release of basic fibroblast growth factor. Biomaterials 1991 September; 12(7):619-626.

What is claimed is:

1. A biphasic material, comprising at least two first segments and at least two second segments, the first segments comprising a doped conductive polymer having a first polymer component doped with a non-metal component which increases the conductivity of the first polymer component, and the second segments comprising a second conductive polymer component, wherein the at least two first segments are disposed in contact with the at least two second segments, in alternating fashion, to provide the biphasic material with repeating alternating first and second polymer components.

2. The biphasic material of claim 1, wherein the first polymer component comprises a bioabsorbable polymer.

3. The biphasic material of claim 1, wherein the first polymer component comprises poly glycerol sebacate, an esterified polyglycerol sebacate, glycolic acid, polydiolcitrate, poly(ester-urethane)urea, polycaprolactone, hydroxyapatite, hyaluronic acid, alginate, collagen, elastin, vimentin, laminin, fibrin, melanin, gum arabic, polycaprolactonefumarate, poly(octane diol) citrate, lactic acid, or combinations thereof.

4. The biphasic material of claim 3, wherein the esterified polyglycerol sebacate is acrylated polyglycerol sebacate.

5. The biphasic material of claim 1, wherein the second polymer component comprises a bioabsorbable polymer.

6. The biphasic material of claim 1, wherein the second polymer component comprises poly glycerol sebacate, an esterified polyglycerol sebacate, glycolic acid, polydiolcitrate, poly(ester-urethane)urea, polycaprolactone, hydroxyapatite, alginate, hyaluronic acid, collagen, elastin, vimentin, laminin, fibrin, melanin, gum arabic, polycaprolactonefumarate, poly(octane diol) citrate, lactic acid, or combinations thereof.

7. The biphasic material of claim 6, wherein the esterified polyglycerol sebacate is acrylated polyglycerol sebacate.

8. The biphasic material of claim 1, wherein the non-metal component comprises polypyrrole, polyaniline, poly(3,4-ethylenedioxythiophene), polyacetylene carbon nanotubes, a silicate, or combinations thereof.

9. The biphasic material of claim 1, wherein the non-metal component has a conductivity in the range of 5-200 S/cm.

10. The biphasic material of claim 1, wherein the first polymer component and second polymer component are configured to support differing electric field gradients, respectively, therein.

11. The biphasic material of claim 1, wherein the doped conductive polymer has a conductivity of $10^{-6}$-$10^{-4}$ S/cm.

12. The biphasic material of claim 1, wherein the second polymer component has a conductivity less than $1.25 \times 10^{-5}$ S/cm.

13. The biphasic material of claim 1, wherein the first segments have the mechanical properties of native human nerve tissue.

14. The biphasic material of claim 13, wherein the first polymer has one or more of an elastic modulus of 0.4-0.7 mPa and a tensile strength of 0.21-1.49 N.

15. The biphasic material of claim 13, wherein the second segments have the mechanical properties of native human nerve tissue.

16. The biphasic material of claim 15, wherein the second polymer has one or more of an elastic modulus of 0.4-0.7 mPa and a tensile strength of 0.21-1.49 N.

17. A method of repairing a damaged nerve, comprising:
 a. providing a tube having a hollow lumen with opposing proximal and distal open ends, the tube comprising the biphasic material of claim 1, wherein the tube is configured to support a plurality of electric field gradients along its length and permit the ingrowth of nerve tissue within the lumen; and
 b. securing a proximal stump of the damaged nerve within the proximal end of the tube and, securing a distal stump of the damaged nerve within the distal end of the tube such that proximal and distal stump of the damaged nerve are in electrical communication with the tube.

18. The method according to claim 17, further comprising seeding the tube with one or more of Schwann cells, neuronal cells, stem cells, and fibroblasts.

19. The biphasic material according to claim 1, comprising one or more of Schwann cells, neuronal cells, stem cells, and fibroblasts.

20. The biphasic material of claim 1, wherein the first polymer component is acrylated polyglycerol sebacate, the second polymer component is acrylated polyglycerol sebacate, and the non-metal component is polypyrrole.

21. An open-ended, hollow tube configured to support a plurality of electric field gradients along its length and having a lumen extending therethrough to permit the growth of nerve tissue therein, the tube comprising a plurality of first conductive tubular segments and a plurality of second conductive tubular segments adjoined along a common axis of the tube to provide the lumen along the common axis, the first conductive tubular segments comprising a first polymer component doped with a non-metal component which increases the conductivity of the first polymer component, and the second tubular segments comprising a second conductive polymer component.

22. The tube according to claim 21, wherein the tube is bioresorbable.

23. The tube according to claim 21, wherein the first polymer component comprises a bioabsorbable polymer.

24. The tube according to claim 21, wherein the first polymer component comprises poly glycerol sebacate, an esterified polyglycerol sebacate, glycolic acid, polydiolcitrate, poly(ester-urethane)urea, polycaprolactone, hydroxyapatite, alginate, collagen, elastin, vimentin, laminin, fibrin, melanin, hyaluronic acid, gum arabic, polycaprolactonefumarate, poly(octane diol) citrate, lactic acid, or combinations thereof.

25. The tube according to claim 24, wherein the esterified polyglycerol sebacate is acrylated polyglycerol sebacate.

26. The tube according to claim 21, wherein the second polymer component comprises a bioabsorbable polymer.

27. The tube according to claim 21, wherein the second polymer component comprises poly glycerol sebacate, an esterified polyglycerol sebacate, glycolic acid, polydiolcitrate, poly(ester-urethane)urea, polycaprolactone, hydroxyapatite, alginate, collagen, elastin, vimentin, laminin, hyaluronic acid, fibrin, melanin, gum arabic, polycaprolactonefumarate, poly(octane diol) citrate, lactic acid, or combinations thereof.

28. The tube according to claim 27, wherein the esterified polyglycerol sebacate is acrylated polyglycerol sebacate.

29. The tube according to claim 21, wherein the non-metal component comprises polypyrrole, polyaniline, poly(3,4-ethylenedioxythiophene), polyacetylene carbon nanotubes, a silicate, or combinations thereof.

30. The tube according to claim 21, wherein the non-metal component has a conductivity in the range of 5-200 S/cm.

31. The tube according to claim 21, wherein the second polymer components has a relatively lower conductivity than the first polymer component.

32. The tube according to claim 21, wherein the doped conductive polymer has a conductivity of $10^{-6}$-$10^{-4}$ S/cm.

33. The tube according to claim 21, wherein the second polymer component has a conductivity less than $1.25 \times 10^{-5}$ S/cm.

34. The tube according to claim 21, wherein the first tubular segments have the mechanical properties of native human nerve tissue.

35. The tube according to claim 34, wherein the first polymer has one or more of an elastic modulus of 0.4-0.7 mPa and a tensile strength of 0.21-1.49 N.

36. The tube according claim 34, wherein the second tubular segments have the mechanical properties of native human nerve tissue.

37. The tube according to claim 36, wherein the second polymer has one or more of an elastic modulus of 0.4-0.7 mPa and a tensile strength of 0.21-1.49 N.

38. The tube according to claim 21, wherein the length of each of the first tubular segments and the length of each of the second tubular segments are equal.

39. The tube according to claim 21, wherein the length of each of the first tubular segments and the length of each of the second tubular segments are not equal.

40. The tube according to claim 39, wherein the length of the first tubular segments is 10-1200 µm.

41. The tube according to claim 40, wherein the length of the first tubular segments is at least about 600 µm.

42. The tube according to claim 39, wherein the length of the second tubular segments are less than the first tubular segments.

43. The tube according to claim 39, wherein the length of the second tubular segments is 10-600 µm.

44. The tube according to claim 21, wherein the cylinder wall thickness of the plurality of first tubular segments is 0.1 mm to 1.0 cm.

45. The tube according to claim 21, wherein the cylinder wall thickness of the plurality of second tubular segments is 0.1 mm to 1.0 cm.

46. The tube according to claim 21, wherein each successive adjoined tubular segment has a smaller radius than a preceding tubular segment.

47. The tube of claim 46, wherein each tubular segment of the plurality of tubular segments has a cylinder wall thickness of 0.1 mm to 1.0 cm.

48. The tube according to claim 46, comprising one or more of Schwann cells, neuronal cells, stem cells, and fibroblasts.

49. A sheet comprising the biphasic material of claim 1.

50. The sheet of claim 49, comprising one or more of Schwann cells, neuronal cells, stem cells, and fibroblasts.

51. A strip comprising the biphasic material of claim 1.

52. The strip of claim 51, comprising one or more of Schwann cells, neuronal cells, stem cells, and fibroblasts.

53. The tube according to claim 21, wherein at least one of the first and second polymer components comprises an esterified polyglycerol sebacate polymer, the repeating structural unit of the esterified polyglycerol sebacate polymer having the formula

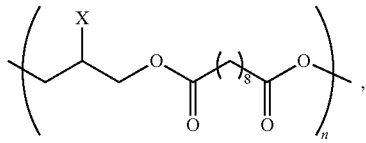

wherein X is an ester.

54. The tube according to claim 53, wherein the repeating structural unit of the esterified polyglycerol sebacate polymer has the formula

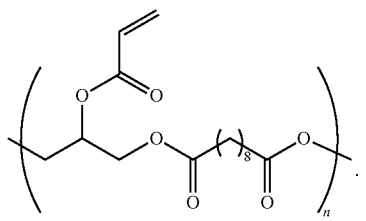

55. The tube according to claim 21, comprising one or more of Schwann cells, neuronal cells, stem cells, and fibroblasts.

56. The tube of claim 21, wherein the first conductive polymer component is acrylated polyglycerol sebacate, the second conductive polymer component is acrylated polyglycerol sebacate, and the non-metal component is polypyrrole.

57. A method of making a tube configured to support a plurality of electric field gradients along its length, comprising:
   a. providing a mold having a plurality of annular valleys disposed on an exterior surface of the mold in spaced apart relation along a longitudinal axis thereof;
   b. placing a first conductive polymer in the valleys;
   c. placing a high conductivity polymer over the first conductive polymer, the high conductivity polymer having a greater conductivity than that of the first conductive polymer;
   d. adhering the first conductive polymer and high conductivity polymer to one another; and
   e. removing the adhered first conductive polymer and high conductivity polymer from the mold to provide the tube configured to support a plurality of electric field gradients along its length.

58. The method according to claim 57, wherein at least one of the first conductive polymer and high conductivity polymer comprise a bioabsorbable material.

59. The method according to claim 57, wherein adhering the polymers comprises crosslinking the first conductive polymer and high conductivity polymer.

60. The method according to claim 57, wherein providing a mold comprises providing a cylindrical mold.

61. The method according to claim 57, further comprising forming pores within the first conductive polymer and high conductivity polymer.

62. The method according to claim 57, further comprising seeding the tube with one or more of Schwann cells, neuronal cells, stem cells, and fibroblasts.

63. The method of claim 57, wherein the low conductivity polymer component comprises acrylated polyglycerol sebacate and the high conductivity polymer component comprises acrylated polyglycerol sebacate and polypyrrole.

* * * * *